United States Patent
Sachdeva et al.

(10) Patent No.: US 10,172,838 B1
(45) Date of Patent: Jan. 8, 2019

(54) SELF-EMULSIFYING FORMULATION OF CARP-1 FUNCTIONAL MIMETICS

(71) Applicant: Florida A&M University, Tallahassee, FL (US)

(72) Inventors: Mandip Sachdeva, Tallahassee, FL (US); Ketankumar Patel, Tallahassee, FL (US); Arun Rishi, Detroit, MI (US)

(73) Assignee: Florida A&M University, Tallahassee, FL (US)

( * ) Notice: Subject to any disclaimer, the term of this patent is extended or adjusted under 35 U.S.C. 154(b) by 0 days.

(21) Appl. No.: 15/459,215

(22) Filed: Mar. 15, 2017

Related U.S. Application Data

(60) Provisional application No. 62/308,456, filed on Mar. 15, 2016.

(51) Int. Cl.
| | | |
|---|---|---|
| *A61K 31/433* | (2006.01) | |
| *A61K 31/4439* | (2006.01) | |
| *A61K 31/4709* | (2006.01) | |
| *A61K 47/16* | (2006.01) | |
| *A61K 47/44* | (2017.01) | |
| *A61K 9/00* | (2006.01) | |
| *A61K 9/107* | (2006.01) | |

(52) U.S. Cl.
CPC .......... *A61K 31/433* (2013.01); *A61K 9/0053* (2013.01); *A61K 9/1075* (2013.01); *A61K 31/4439* (2013.01); *A61K 31/4709* (2013.01); *A61K 47/16* (2013.01); *A61K 47/44* (2013.01)

(58) Field of Classification Search
CPC .............. A61K 31/433; A61K 31/4439; A61K 31/4709; A61K 9/0053; A61K 9/1075; A61K 47/16; A61K 47/44
USPC .......................................................... 514/278
See application file for complete search history.

(56) References Cited

U.S. PATENT DOCUMENTS

| | | | |
|---|---|---|---|
| 4,327,076 A | 4/1982 | Puglia et al. | |
| 6,004,566 A | 12/1999 | Friedman et al. | |
| 6,174,547 B1 | 1/2001 | Dong et al. | |
| 6,562,372 B1 | 5/2003 | Yokoi et al. | |
| 9,598,441 B2 * | 3/2017 | Rishi .................... | C07D 513/10 |
| 2005/0037073 A1 | 2/2005 | Schwarz | |
| 2014/0221412 A1 * | 8/2014 | Rishi .................... | C07D 513/10 514/278 |

OTHER PUBLICATIONS

Gupta et al. ISRN Pharmaceuticals p. 1-16, published online Dec. 26, 2013.*
Muthu et al. J Biomed Nanotechnol, (Sep. 2015); 11(9); p. 1608-1627.*
O'Toole, S.A. et al, Therapeutic targets in triple negative breast cancers. J Clin Pathol. 2013; 66:530-542.
Rishi, A.K. et al, Identification and characterization of a Cell-Cycle and Apoptosis Regulatory Protein [CARP]-1 as a novel mediator of apoptosis signaling by Retinoid CD437. J Biol Chem. 2003; 278:33422-33435.
Kim, J.H. et al., CCAR1, a key regulator of mediator complex recruitment to nuclear receptor transcription complexes. Molecular Cell. 2008; 31:510-519.
Rishi, A.K. et al., Cell cycle and apoptosis regulatory protein [CARP]-1 is involved in apoptosis signaling by epidermal growth factor receptor. J Biol Chem. 2006; 281:13188-98.
Muthu, M. et al., CARP-1/CCAR1:A biphasic regulator of cancer cell growth and apoptosis. Oncotarget. 2015; 6:6499-6510. doi: 10.18632/oncotarget.3376.
Puliyappadamba, V.T. et al., Antagonists of anaphase promoting complex [APC]-2-cell cycle and apoptosis regulatory protein (CARP)-1 interaction are novel regulators of cell growth and apoptosis. J Biol Chem. 2011; 286:38000-38017.
Muthu, M. et al., Identification and testing of novel CARP-1 functional mimetic compounds as inhibitors of non-small cell lung and triple-negative breast cancers. J. Biomed. Nanotechnol. 2015; 11:1608-1627.
Jamal, S. et al., CARP-1 functional mimetics are a novel class of small molecule inhibitors of malignant pleural mesothelioma cells. PLos One. 2014; 9:e89146.
Ashour, A.E. et al., CARP-1 functional mimetics: A novel class of small molecule inhibitors of medulloblastoma cell growth. PLoS One. 2013; 8:e66733.
Yin, S. et al., Anti-estrogen resistant breast cancers cells are sensitive to cisplatin plus TRAIL treatment. Oncology Reports. 2015; 33:1475-80.
Nahta, R. et al., Lapatinib induces apoptosis in trastuzumab-resistant breast cancer cells: effects on insulin-like growth factor I signaling. Mol Cancer Ther. 2007; 6:667-674.
Dexter, D.L. et al., Heterogeneity of tumor cells from a single mouse mammary tumor. Cancer Res. 1978; 38:3174-81.
Aslakson, C.J. et al., Selective events in the metastatic process defined by analysis of the sequential dissemination of subpopulations of a mouse mammary tumor. Cancer Res. 1992; 52:1399-1405.
Bursavich, M.G. et al., 5'-Phenyl-3'H-spiro[indoline-3,2'-[1,3,4]thiadiazol]-2-one inhibitors of ADAMTS-5 (Aggrecanase-2) Bioorg. Med. Chem. Lett. 2007; 17:5630-5633.
Liang, C.C. et al., In vitro scratch assay: a convenient and inexpensive method for analysis of cell migration in vitro. Nat Protoc. 2007; 2:329-33.

(Continued)

*Primary Examiner* — Yong L Chu
(74) *Attorney, Agent, or Firm* — Nilay J. Choksi; Paul Murty; Smith & Hopen, P.A.

(57) ABSTRACT

A solid self-micro/nano emulsifying formulation comprising CARP-1 functional mimetics (CFM; e.g., CFM-4.16 or CFM-4.17) for oral administration, and methods of fabrication and use thereof to treat cancer (e.g., breast cancer, triple negative breast cancer, resistant lung cancer, and non-resistant lung cancer) and reduce tumor volume. Solid self-micro/nano emulsifying formulation of CFM compounds was found to have significantly enhanced drug loading, aqueous solubility, and oral bioavailability of the formulation.

13 Claims, 50 Drawing Sheets

(56) References Cited

OTHER PUBLICATIONS

Zhang, L. et al., Transactivator of transcription tagged cell cycle and apoptosis regulatory protein-1 peptides suppress growth of human breast cancer cells in vitro and in vivo. Mol Cancer Ther. 2007; 6:1661-1672.
Zhang, W. et al., Enhanced cellular uptake and anti-proliferating effect of chitosan hydrochlorides modified genistein loaded NLC on human lens epithelial cells. Int J Pharm. 2014; 471:118-26.
Tian, B. et al., Novel surface-modified nanostructured lipid carriers with partially deacetylated water-soluble chitosan for efficient ocular delivery. J Pharm Sci. 2012; 101:1040-9.
Chougule, M.B. et al., Antitumor activity of Noscapine in combination with Doxorubicin in triple negative breast cancer. PLoS One. 2011; 6:e17733.
Lombardo, Y. et al., Mammosphere Formation Assay from Human Breast Cancer Tissues and Cell Lines. J. Vis. Exp. 2015; 97: e52671. doi:10.3791/52671.
Rosenzweig, S.A. et al., Acquired resistance to drugs targeting receptor tyrosine kinases. Biochem Pharmacal. 2011; 83:1041-8.
Garcia, R. et al., Constitutive activation of Stat3 by the Src and JAK tyrosine kinases participates in growth regulation of human breast carcinoma cells. Oncogene. 2001; 20:2499-513.
Gnoni, A. et al., Dasatinib: an anti-tumour agent via Src inhibition. Curr Drug Targets. 2011; 12:563-78.
Scagliotti, G. et al., Phase III multinational, randomized, double-blind, placebo-controlled study of Tivantinib (ARQ 197) plus erlotinib versus erlotinib alone in previously treated patients with locally advanced or metastatic nonsquamous non-small-cell lung cancer. J Clin Oncol. 2015; 33:2667-2674.
Wicha, M.S. et al., Cancer stem cells: an old idea—a paradigm shift. Cancer Res. 2006; 66:1883-90; Visvader JE, Lindeman GJ. Cancer stem cells in solid tumours: accumulating evidence and unresolved questions. Nat Rev Cancer. 2008; 8:755-68.
Hadjimichael, C. et al., Common stemness regulators of embryonic and cancer stem cells. World Journal of Stem Cells. 2015; 7:1150-1184.
Ho-Yen, C.M. et al., The clinical and functional significance of c-Met in breast cancer: a review. Breast Cancer Res. 2015; 17:52. doi: 10.1186/s13058-015-0547-6.
Gelsomino, F. et al., Targeting the MET gene for the treatment of non-small-cell lung cancer. Crit Rev Oncol Hematol. 2014; 89:284-99.
Crown, J. et al., Emerging targeted therapies in triple-negative breast cancer. Annals of Oncology. 2012; 23:56-65.
Kim, Y.J. et al., MET is a potential target for use in combination therapy with EGFR inhibition in triple-negative/basal-like breast cancer. Int J Cancer. May 15, 2014;134(10):2424-36.
Montero, J.C. et al., Inhibition of SRC family kinases and receptor tyrosine kinases by dasatinib: possible combinations in solid tumors. Clin Cancer Res. 2011; 17:5546-52.
Lue, H. et al., Src and STAT3 inhibitors synergize to promote tumor inhibition in renal cell carcinoma. Oncotarget. 2015; 6:44675-44687. doi: 10.18632/oncotarget.5971.
Hussain et al., Novel drug delivery system for lipophilic therapeutics of small molecule, peptide-based and protein drugs, Chirality, 2010,22 Suppl 1:E44-6.
Cheriyan et al., CARP-1 functional mimetics are novel inhibitors of drug-resistant triple negative breast cancers, Oncotarget, 2016, vol. 7, No. 45, pp. 73370-73388.
Andey et al., Lipid Nanocarriers of a Lipid-Conjugated Estrogenic Derivative Inhibit Tumor Growth and Enhance Cisplatin Activity against Triple-Negative Breast Cancer: Pharmacokinetic and Efficacy Evaluation, Molecular Pharmaceutics, 2015, vol. 12, pp. 1105-1120.
Patel et al., Evaluation of self-emulsified DIM-14 in dogs for oral bioavailability and in Nu/nu mice bearing stem cell lung tumor models for anticancer activity, J Control Release. Sep. 10, 2015; 213: 18-26.
Zanchetta et al., Self-Emulsifying Drug Delivery Systems (SEDDS) in Pharmaceutical Development, J. Advanced Chemical Engineering, 2015, vol. 5, Issue 3.
Andey et al., Formulation, Pharmacokinetic, and Efficacy Studies of Mannosylated Self-Emulsifying Solid Dispersions of Noscapine, 2016, PLoS ONE 11(1): e0146804.

* cited by examiner

| TNBC Cells\Drugs | MDA-MB-468 | MDA-MB-231 | CRL2335 | Hs-578T | BT-20 | HCC-1806 | HCC-1937 (BRCA1-Null) |
|---|---|---|---|---|---|---|---|
| CFM-4.16 (5μM, 6h) | 84 (0.081) | 63 (0.03) | 76 (0.01) | 55 (0.005) | 53 (0.0086) | 31 (0.010) | 44 (0.035) |
| ADR (5μM, 6h) | 99 (0.031) | 93 (0.033) | 90 (0.004) | 73 (0.005) | 78 (0.0129) | 89 (0.0091) | 98 (0.006) |
| CFM-4.16 +ADR | 36 (0.036) | 58 (0.023) | 61 (0.020) | 45 (0.005) | 34 (0.0084) | 21 (0.0036) | 28 (0.019) |
| Etoposide (17μM, 6h) | 68 (0.080) | 85 (0.025) | 94 (0.013) | ND | ND | ND | ND |
| Etoposide +CFM-4.16 | 57 (0.041) | 36 (0.024) | 52 (0.014) | ND | ND | ND | ND |

*FIG. 3C*

MDA-MB-468 (WT)

| | Control | CFM-4 | CFM-4.16 | Cisplatin | Adriamycin |
|---|---|---|---|---|---|
| 00 h | | | | | |
| 72 h | | | | | |

*FIG. 11B*

| MDA-MB-468 (Adriamycin-R; Clone 1) |||||
|---|---|---|---|---|
| | Control | CFM-4 | CFM-4.16 | Adriamycin |
| 00 h | | | | |
| 72 h | | | | |

*FIG. 11C*

| | Soft Agar Assay (4 Weeks) | | | |
|---|---|---|---|---|
| | Control (Untreated) | CFM-4 (10μM) | CFM-4.16 (10μM) | Adriamycin (10μM) |
| MDA-MB-468 | | | | |
| MDA-MB-468 (Adriamycin-R) Clone 1 | | | | |

*FIG. 11D*

MDA-MB-231 TNBC Cells

| | Control | CFM-4 (3μM) | CFM-5 (3μM) | CFM-4.16 (3μM) | CFM-4.17 (3μM) | Cisplatin (3.3μM) |
|---|---|---|---|---|---|---|
| 00 h | | | | | | |
| 96 h | | | | | | |

*FIG. 12A*

| MDA-MB-468 (Cisplatin-R; Clone 1) ||||
|---|---|---|---|---|
| | Control | CFM-4 | CFM-4.16 | Cisplatin |
| 00 h | | | | |
| 72 h | | | | |

*FIG. 12B*

SKBR-3 (WT) Cells

|  | Control | CFM-4 (3μM) | CFM-4.16 (1μM) | Herceptin (2μg/ml) |
|---|---|---|---|---|
| 00 h | | | | |
| 72 h | | | | |

SELF-EMULSIFYING FORMULATION OF CARP-1 FUNCTIONAL MIMETICS

CROSS-REFERENCE TO RELATED APPLICATIONS

This nonprovisional application claims priority to U.S. Provisional Patent Application No. 62/308,456, entitled "Self-Emulsifying Formulation of CARP-1 Functional Mimetics", filed Mar. 15, 2016 by the same inventors, the entirety of which is incorporated herein by reference.

BACKGROUND OF THE INVENTION

1. Field of the Invention

This invention relates, generally, to cancer therapeutics. More specifically, it relates to CARP-1 functional mimetics with enhanced bioavailability and solubility.

2. Brief Description of the Prior Art

The American Cancer Society estimates indicate approximately 246,000 new cases and 40,000 deaths in the United States resulting from breast cancers in females in 2016 [Siegel R L, Miller K D, Jemal A. Cancer Statistics, 2016. CA Cancer J Clin. 2016; 66:7-30]. Over the previous decade, the incidence rates and consequent mortality associated with the breast cancers decreased in part due to advances in diagnosis and therapeutic modalities. The development of therapeutics that target estrogen receptor (ER) function and estrogen biosynthesis, and the human epidermal growth factor receptor (EGFR) 2 (aka Her2) have benefited a vast majority of breast cancer patients. However, a significant percent of breast cancers lacks ER, progesterone receptor (PR), and Her2, and are often grouped as triple-negative breast cancers (TNBCs). Chemotherapy including an anthracycline, cisplatin and/or taxane-based regimen remains the current best standard of care for TNBCs. A recent study indicating existence of molecular subtypes among TNBCs underscores further stratification of this subgroup of hard-to-treat cancers, and emphasizes the unmet need for identification of better molecular-based therapies [Lehmann B D, Bauer J A, Chen X, Sanders M E, Chakravarthy A B, Shyr Y, Pietenpol J A. Identification of human triple-negative breast cancer subtypes and preclinical models for selection of targeted therapies. J Clin Invest. 2011; 121:2750-2767]. Although a number of cell growth and survival pathways are being actively pursued for targeting TNBCs [O'Toole S A, Beith J M, Miller E K A, West R, McLean A, Cazet A, Swarbrick A, Oakes S R. Therapeutic targets in triple negative breast cancers. J Clin Pathol. 2013; 66:530-542], better and effective strategies are urgently needed to overcome drug resistance and improve therapeutic outcomes.

Poor bioavailability of drugs has been a major limitation in the successful utilization of many therapeutically-effective molecules. As it happens, most of these molecules are lipophilic in nature and tend to be poorly absorbed in the aqueous medium that is present in the gastrointestinal (GI) tract. The problem of poor bioavailability is at times further compounded by a faster elimination rate, which further reduces the efficiency of such molecules being used as a drug target of choice.

Oral administration is regarded as the preferred route of drug intake, as it offers numerous advantages over other forms of administration, including convenience, ease of compliance, potential for availability to large patent population, and cost effectiveness. However, many compounds have extremely poor oral bioavailability, resulting in loss of otherwise-effective therapies or loss of the convention option of oral administration. For example, most anti-cancer compounds are administered intravenously because of poor oral bioavailability. In such scenarios, orally-bioavailable anticancer compounds would be extremely beneficial in cancer treatment, as the oral route has significantly higher patient compliance compared to intravenous injection. However, this is not possible with the conventional art due to lack of bioavailability.

Cell cycle and apoptosis regulator 1 (CCAR1/CARP-1) is a peri-nuclear phospho-protein, that regulates cell growth and apoptosis signaling in a variety of cancer cells [Rishi A K, Zhang L, Boyanapalli M, Wali A, Mohammad R M, Yu Y, Fontana J A, Hatfield J S, Dawson M I, Majumdar A P N, Reichert U. Identification and characterization of a Cell-Cycle and Apoptosis Regulatory Protein [CARP]-1 as a novel mediator of apoptosis signaling by Retinoid CD437. J Biol Chem. 2003; 278:33422-33435; Kim J H, Yang C K, Heo K, Roeder R G, An W, Stallcup M R. CCAR1, a key regulator of mediator complex recruitment to nuclear receptor transcription complexes. Molecular Cell. 2008; 31:510-519; Rishi A K, Zhang L, Yu Y, Jiang Y, Nautiyal J, Wali A, Fontana J A, Levi E, Majumdar A P N. Cell cycle and apoptosis regulatory protein [CARP]-1 is involved in apoptosis signaling by epidermal growth factor receptor. J Biol Chem. 2006; 281:13188-98; Muthu M, Cheriyan, V T, Rishi A K. CARP-1/CCAR1: A biphasic regulator of cancer cell growth and apoptosis. Oncotarget. 2015; 6:6499-6510. doi: 10.18632/oncotarget.3376]. In addition to transcriptional co-activation of the steroid family of nuclear receptors, CARP-1 regulates Doxorubicin/Adriamycin (ADR)-dependent DNA damage-induced apoptosis in a manner dependent as well as independent of co-activation of tumor suppressor p53 [Rishi A K, Zhang L, Boyanapalli M, Wali A, Mohammad R M, Yu Y, Fontana J A, Hatfield J S, Dawson M I, Majumdar A P N, Reichert U. Identification and characterization of a Cell-Cycle and Apoptosis Regulatory Protein [CARP]-1 as a novel mediator of apoptosis signaling by Retinoid CD437. J Biol Chem. 2003; 278:33422-33435; Kim J H, Yang C K, Heo K, Roeder R G, An W, Stallcup M R. CCAR1, a key regulator of mediator complex recruitment to nuclear receptor transcription complexes. Molecular Cell. 2008; 31:510-519]. Withdrawal of serum growth factors or blockage of EGFR results in elevated CARP-1 expression, cell cycle arrest, and apoptosis, while knockdown of CARP-1 resulted in resistance to apoptosis by ADR or EGFR tyrosine kinase inhibitors [Rishi A K, Zhang L, Boyanapalli M, Wali A, Mohammad R M, Yu Y, Fontana J A, Hatfield J S, Dawson M I, Majumdar A P N, Reichert U. Identification and characterization of a Cell-Cycle and Apoptosis Regulatory Protein [CARP]-1 as a novel mediator of apoptosis signaling by Retinoid CD437. J Biol Chem. 2003; 278:33422-33435; Kim J H, Yang C K, Heo K, Roeder R G, An W, Stallcup M R. CCAR1, a key regulator of mediator complex recruitment to nuclear receptor transcription complexes. Molecular Cell. 2008; 31:510-519; Rishi A K, Zhang L, Yu Y, Jiang Y, Nautiyal J, Wali A, Fontana J A, Levi E, Majumdar A P N. Cell cycle and apoptosis regulatory protein [CARP]-1 is involved in apoptosis signaling by epidermal growth factor receptor. J Biol Chem. 2006; 281: 13188-98].

In an attempt to elucidate molecular mechanisms of CARP-1 signaling, the current inventors performed yeast-two-hybrid assays and discovered that CARP-1 binds with cell cycle regulatory anaphase promoting complex/cyclosome (APC/C) E3 ligase subunit APC2 [Puliyappadamba V T, Wu W, Bevis D, Zhang L, Polin L, Kilkuskie R, Finley R L, Larsen S D, Levi E, Miller F R, Wali A, Rishi A K. Antagonists of anaphase promoting complex [APC]-2-cell cycle and apoptosis regulatory protein (CARP)-1 interaction are novel regulators of cell growth and apoptosis. J Biol Chem. 2011; 286:38000-38017]. APC/C is a multi-subunit ubiquitin E3 ligase protein that functions to regulate ubiquitin-dependent proteasomal turnover of a large number of cellular proteins including the cell cycle regulatory cyclin B1, CDC20, Cdh1, and SCF E3 ligase. APC/C has been well-known to play a distinct role in cell cycle transitions [Zachariae W, Nasmyth K. Whose end is destruction: cell division and the anaphase-promoting complex. Genes Dev. 1999; 13:2039-2058; Harper J W, Burton J L, Solomon M J. The anaphase-promoting complex: it's not just for mitosis any more. Genes Dev. 2002; 16:2179-206], and prior reports have shown that misregulation of APC/C and its substrates correlates with tumor progression [Lehman N L, Tibshirani R, Hsu J Y, Natkunam Y, Harris B T, West R B, Masek M A, Montgomery K, van de Rijn M, Jackson P K. Oncogenic Regulators and Substrates of the Anaphase Promoting Complex/Cyclosome Are Frequently Overexpressed in Malignant Tumors. Am J Pathol. 2007; 170:1793-1805].

The current inventors exploited the APC/C co-activation function of CARP-1 and identified a number of small molecule inhibitors (SMIs) of CARP-1 binding with APC2 [Puliyappadamba et al.]. These compounds, termed CARP-1 functional mimetics (CFMs), are a class of small molecule compounds that interfere with CARP-1 binding with APC/C subunit APC-2, and suppress growth of a variety of cancer cells by promoting apoptosis [Puliyappadamba et al.; Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1; Jamal S, Cheryan V T, Muthu M, Munie S, Levi E, Ashour A E, Pass H I, Wali A, Singh M, Rishi A K. CARP-1 functional mimetics are a novel class of small molecule inhibitors of malignant pleural mesothelioma cells. PLos One. 2014; 9:e89146; Ashour A E, Jamal S, Cheryan V T, Muthu M, Zoheir K M A, Alafeefy A M, Abd-allah AR, Levi E, Tarca A L, Polin L A, Rishi A K. CARP-1 functional mimetics: A novel class of small molecule inhibitors of medulloblastoma cell growth. PLoS One. 2013; 8:e66733]. CFMs belong to an emerging class of novel scaffolds that function in part by inhibiting protein-protein interaction between CARP-1/CCAR1 and the E3 ubiquitin ligase Anaphase promoting complex subunit APC-2 [Puliyappadamba et al.]. The lead compound CFM-4 binds with CARP-1/CCAR1, causes elevated levels of CARP-1, stimulates apoptosis in a number of cancer cell types [Puliyappadamba et al.; Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627; Jamal S, Cheryan V T, Muthu M, Munie S, Levi E, Ashour A E, Pass H I, Wali A, Singh M, Rishi A K. CARP-1 functional mimetics are a novel class of small molecule inhibitors of malignant pleural mesothelioma cells. PLos One. 2014; 9:e89146; Ashour A E, Jamal S, Cheryan V T, Muthu M, Zoheir K M A, Alafeefy A M, Abd-allah AR, Levi E, Tarca A L, Polin L A, Rishi A K. CARP-1 functional mimetics: A novel class of small molecule inhibitors of medulloblastoma cell growth. PLoS One. 2013; 8:e66733].

CFM compounds are extremely hydrophobic compounds and thus have very poor aqueous solubility and permeability across biological membranes. For oral absorption, a compound needs to be solubilized in gastric milieu and should permeate through the intestinal mucosa in order to achieve a therapeutic concentration in the blood. Generally, such water insoluble compounds are administered with anionic or non-ionic surfactant, PEG400, vegetable oils, etc. However, CFM compounds are only very slightly soluble in orally-biocompatible organic solvents (e.g., ethanol, PEG400, etc.) and common surfactants (e.g., polysorbate 80, SLS, etc.). As such, there are no known or available formulations of CFM or its analogs.

Attempts have been made to alleviate the foregoing problems. For example, U.S. Patent Application Publication No. 2005/0037073 describes the preparation of solid self-emulsifying dosage form for improved delivery of poorly soluble hydrophobic compounds. Additionally, the use of microcrystalline cellulose, inorganic silicates, silicon dioxide or calcium phosphate as oil sorbents have been described in, for example, U.S. Pat. Nos. 4,327,076 and 6,562,372. However, to obtain a free-flowing oil-containing composition for tableting, the '372 patent used emulsification, followed by spray-drying, without which, tablet formulations could not be prepared.

U.S. Pat. No. 6,174,547 teaches a liquid composition comprising a hydrophilic phase retained in an osmotic hydrogel matrix. The '547 patent is primarily focused on a two-phase emulsion, which is different from an emulsifiable composition. The composition set forth in the reference is not emulsifiable, since the composition is already emulsified in its liquid form. In this manner, the '547 patent cannot and does not address the complications associated with providing a homogeneous distribution within a tablet, which composition can be emulsified under certain conditions.

U.S. Pat. No. 6,004,566 discloses a topical emulsion cream. The emulsion is designed for transdermal delivery. The '566 patent is only relevant to emulsions; there is nothing in the reference which would provide one skilled in the art with instruction to form a capsule-based emulsifiable composition for oral administration.

Accordingly, what is needed is an improved delivery system to improve the solubility and oral bioavailability of CFM compounds. However, in view of the art considered as a whole at the time the present invention was made, it was not obvious to those of ordinary skill in the field of this invention how the shortcomings of the prior art could be overcome.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for an anti-cancer therapy is now met by a new, useful, and nonobvious invention.

In an embodiment, the current invention is a formulation comprising a therapeutically-effective amount of a CFM (e.g., CFM-4.16 and/or CFM 4.17) with enhanced oral bioavailability upon oral ingestion and enhanced solubility in an organic solvent (e.g., dimethyl acetamide). The formulation may be a solid self-micro/nano emulsifying formulation. The formulation may further include a pharmaceutically acceptable lipidic excipient (e.g., oil) and a surfactant admixed with the CFM. In a further embodiment, the surfactant can be present in an amount between about 0.1% and about 50% by weight, and the oil can be present in an amount between about 20% and about 80% by weight. In certain embodiments, the therapeutically effective amount of the CFM is about 40 mg/kg of body weight of a patient or subject to which the formulation is orally administered.

In a separate embodiment, the current invention is a method of treating cancer (e.g., breast cancer, triple negative breast cancer, resistant lung cancer, and non-resistant lung cancer) and/or reducing tumor volume in a patient or subject. The method comprises orally administering (e.g., every other day) a therapeutically effective amount of a formulation containing a CFM, as described above.

In yet other embodiments, the current invention can include any one or more—or even all—of the foregoing characteristics and features.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

For a fuller understanding of the invention, reference should be made to the following detailed description, taken in connection with the accompanying drawings, in which:

FIG. 3C depicts indicated TNBC cells treated with DMSO, CFM-4.16, ADR, etoposide, ADR plus CFM-4.16, or etoposide plus CFM-4.16, and percent cell viabilities were determined relative to DMSO-treated controls. *, In the case of Hs-578T cell, the CFM-4.16 dose was 100 nM; ( ), SEM. Overall, FIGS. 3A-3C show that CFM-4.16 inhibits TNBC cell growth and enhances ADR efficacy.

FIGS. 4A-4E show that CFM-4.16 inhibits drug-resistant TNBC cell growth in dose-dependent manner.

FIGS. 5A-5E show that CFM-4.16 stimulates apoptosis in parental and ADR-resistant TNBC cells in part by upregulating pro-apoptotic CARP-1 and activating SAPKs.

FIG. 11B shows that MDA-MB-468 (WT) TNBC cells were untreated (Control), treated with 3 µM of respective CFMs, 3.3 µM of cisplatin, or 1.0 µM of ADR for 72 h, and subjected to scratch assays. The cells growth in the scratch assay was recorded by photography. Representative photomicrographs of untreated and treated TNBC cells are shown.

FIG. 11C shows that MDA-MB-468 (Adriamycin-R; Clone 1) TNBC cells were untreated (Control), treated with 3 µM of respective CFMs, 3.3 µM of cisplatin, or 1.0 µM of ADR for 72 h, and subjected to scratch assays. The cells growth in the scratch assay was recorded by photography. Representative photomicrographs of untreated and treated TNBC cells are shown.

FIG. 11D shows that indicated TNBC cells were seeded in soft-agar and were untreated (Control), treated with 10 µM of CFM-4, CFM-4.16, or ADR for noted time. The number of colonies of cells was recorded by photography. Representative photomicrographs of untreated and treated TNBC cells are shown. Overall, FIGS. 11A-11D show that CFM-4.16 inhibits angiogenesis, parental and ADR-resistant TNBC cell motility, and growth in soft agar.

FIG. 12A shows that MDA-MB-231 TNBC cells were untreated (Control), treated with 3 µM of respective CFMs or 3.3 µM of cisplatin for noted times, and were subjected to scratch assays. The cells growth in the scratch assay was recorded by photography.

FIG. 12B shows that MDA-MB-468 TNBC cells were untreated (Control), treated with 3 µM of respective CFMs or 3.3 µM of cisplatin for noted times, and were subjected to scratch assays. The cells growth in the scratch assay was recorded by photography.

FIGS. 12A-12D show that CFM-4.16 inhibits parental and Cisplatin-resistant TNBC cell motility, and growth in soft agar.

FIG. 13A shows that SKBR-3 (WT) breast cancer cells were untreated (Control), treated with 3 µM of CFM-4, 1.0 µM of CFM-4.16, or 2 µg/ml Herceptin for noted times, and were subjected to scratch assays. The cells growth in the scratch assay was recorded by photography. Representative photomicrographs of untreated and treated breast cancer cells are shown.

FIG. 13C shows that indicated breast cancer cells were seeded in soft-agar and untreated (Control), treated with 10 µM of each of CFMs, or 4 µM of Herceptin for noted time. The number of colonies of cells in panel C was recorded by photography. Representative photomicrographs of untreated and treated breast cancer cells are shown. Overall, FIGS. 13A-13C shows that CFM-4.16 inhibits parental and Herceptin-resistant breast cancer cell motility, and growth in soft agar.

FIGS. 14A-14B show that drug-resistant TNBC cells have elevated expression of cancer stem cell genes, while CFM-4.16 in combination with ADR inhibits cancer stem cell gene expression.

FIGS. 15A-15C** show that CFM-4.16 inhibits growth of mammospheres derived from parental and drug-resistant TNBC cells, and enhances efficacy of ADR in parental and ADR-resistant tumor-derived, CSC-enriched cells.

FIG. 16C show that CFM-4.16 NLF plus Adriamycin treatments inhibit Oct4 expression, and induce CARP-1 expression and apoptosis in TNBC tumor xenografts. A representative tumor tissue from the placebo-treated (noted as Control) or CFM-4.16 NLF plus Adriamycin-treated animal was fixed in formalin, paraffin embedded, processed, and subjected to immuno-staining. Photomicrographs (400× magnification) are shown for apoptosis (by TUNEL assay), and levels CARP-1 and Oct4 proteins. Elevated apoptosis is indicated by increased brown staining or dark-brown spots in CFM-4.16 NLF plus Adriamycin panels stained with anti-CARP-1 antibodies or TUNEL, respectively. Overall, FIGS. 16A-16C depict formulation of surface modified CFM-4.16 NLF and evaluation of its pharmacokinetic parameters and inhibition of TNBC cell-derived xenografts.

DETAILED DESCRIPTION OF THE PREFERRED EMBODIMENT

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Figure 1:
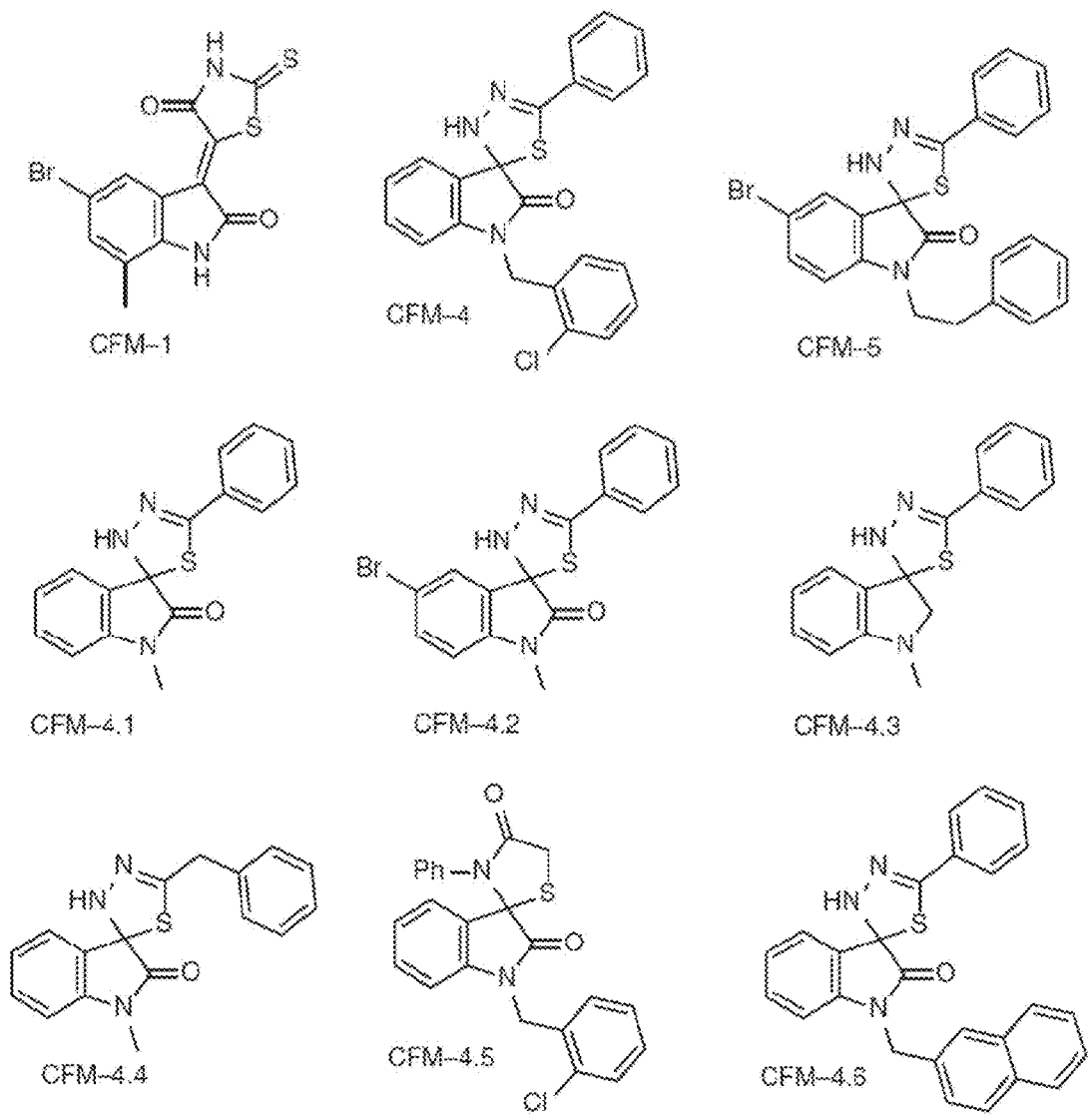
FIG. 1 depict various chemical structures of CFM compounds.

The present invention relates generally to a pharmaceutical composition comprising CARP-1 functional mimetics for oral administration. More specifically, the current invention relates to a solid self-micro/nano emulsifying formulation containing CFM, most preferably CFM-4.16 and/or CFM-4.17, and methods of preparation and use thereof. As noted, CFM is very poorly soluble in most of the biocompatible organic solvents. However, it was found herein that CFM is soluble in dimethyl acetamide (DMA). In particular, it was found that a solution of CFM-4.16 in DMA immediately got precipitated on the addition of water. The current solid self-emulsifying formulation results in effective oral delivery of CFM compounds (see FIG. 1), and in particular CFM-4.16 and CFM-4.17, which are two of the most active CFM compounds.

Optimized amounts of oil and surfactant can be added to prevent the precipitation of CFM-4.16 and to prepare a clear-to-translucent nano-sized globule containing CFM. In an embodiment, the formulation includes at least one physiologically or pharmaceutically acceptable surfactant in an amount between about 0.1% and about 50% by weight and oil in an amount between about 20% and about 80% by weight.

The method used herein to fabricate the current formulation involved solid self-emulsifying formulation technology, which does not involve use of any sophisticated equipment (e.g., high pressure homogenizer, rotary evaporator, table machine, etc.) or special packaging, and thus it offers an economically-efficient formulation/product. Solid self-micro/nano emulsifying formulation of CFM compounds has significantly enhanced drug loading, aqueous solubility, and oral bioavailability of the formulation. Any known solubility enhancing techniques may be used, for example micronization, nanosuspension, cyclodextrin complexation, polyethylene glycol (PEG)-based solid dispersion, salt formation, and solid dispersion, among other known techniques. However, lipid-based self-emulsifying formulation can offer several advantages over other technology, namely that lipids are generally regarded as safe excipients compared to synthetic polymeric excipients. There is also no need for specific equipment, and they allow for economical excipients and manufacturing, rapid solubilization, and enhanced permeability due to lipidic excipients.

Study 1

A solid self-emulsifying formulation, including CFM-4.16, was fabricated by a methodology that produced nano-globules of about 30-50 nm on dispersion to aqueous phase. The formulation was very stable and did not show any agglomeration or precipitation.

A dissolution study was carried out using USP Dissolution Apparatus 2—Paddle (37° C.) in 0.1 N HCl. The solid self-emulsifying formulation of CFM-4.16 gave a greater than about 98% of the drug released within 10 minutes of the dissolution study, suggesting the rapid and complete dissolution of CFM compounds.

Subsequently, an in vivo pharmacokinetic study was carried out in Sprague Dawley (SD) rats, and this study showed significant enhancement in oral bioavailability. For pharmacokinetic evaluation, a sold self-nanoemulsifying drug delivery system (SNEDD) including CFM-4.16 as active agent (40 mg/kg) was given by oral route to SD rats. Blood samples were withdrawn at regular time points, and plasma concentration of CFM-4.16 was analyzed using high-performance liquid chromatography (HPLC). Oral bioavailability of CFM-4.16 formulation was found to be significantly increased as compared to free drug. Table 1 denotes the oral pharmacokinetic parameters.

TABLE 1

Pharmacokinetic parameters of CFM solid self-emulsifying formulation.

|  | CFM Solution | CFM SNEDDS |
|---|---|---|
| AUC (μg · h/ml) | 2.82 ± 0.04 | 5.57 ± 1.2 |
| $T_{1/2}$ (h) | 1.34 ± 0.05 | 7.34 ± 1.6 |
| Absolute Bioavailability (%) | 6.36 | 15.86 |
| Relative Bioavailability (%) | — | 244.36 |

Figure 2A:
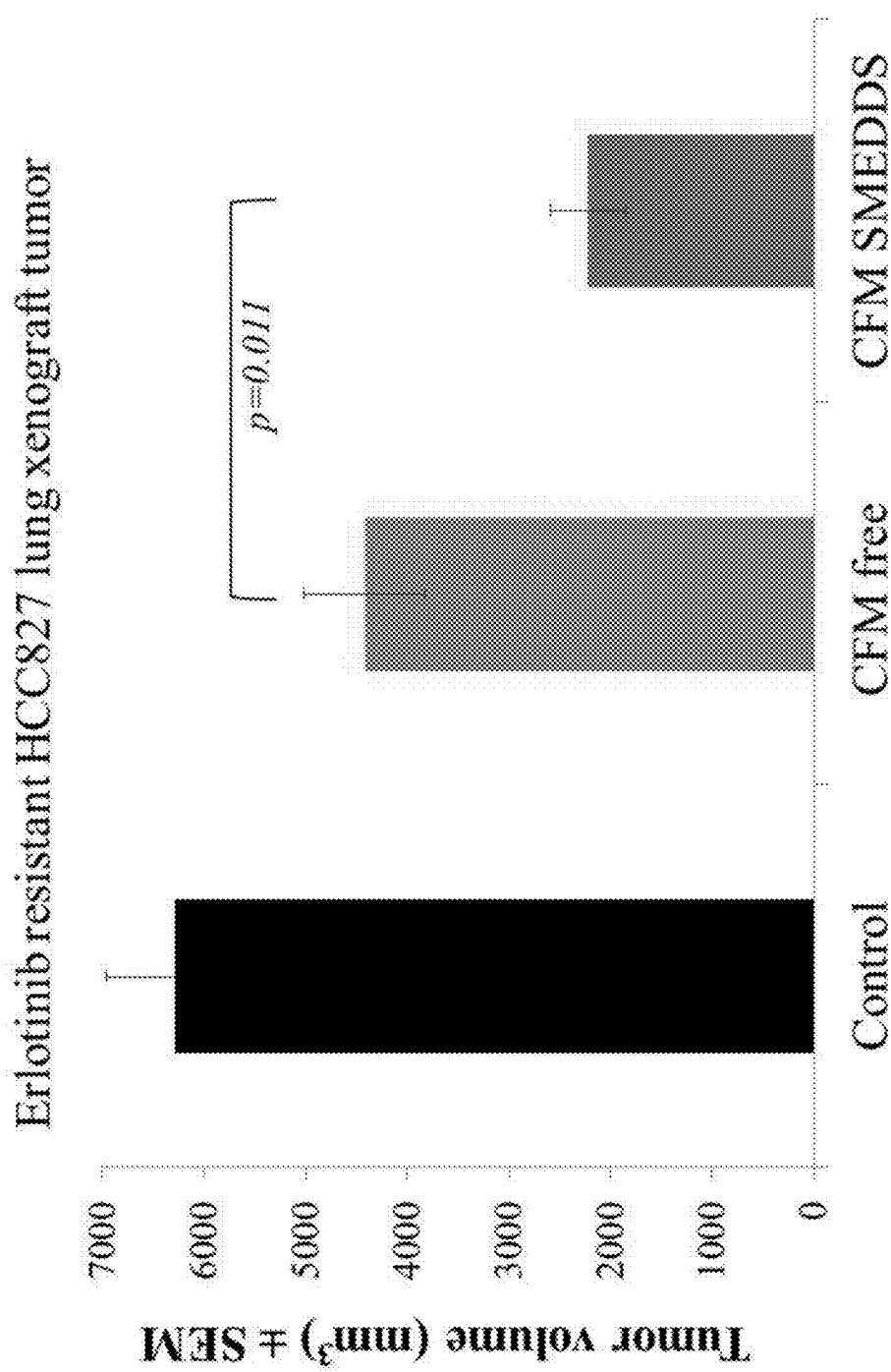
FIG. 2A is a graphical illustration depicting volume of lung tumor (Erlotinib-resistant HCC827 xenograft lung tumor) in tumor-bearing nude mice after CFM-4.16 free drug and CFM-4.16 solid self-emulsifying formulation.

An in vivo anticancer study in Erlotinib-resistant non-small cell lung cancer tumor-bearing nude mice showed significant responses with the novel CFM-4.16 formulation compared to free CFM-4.16 (see FIG. 2A). Specifically, a xenograft lung tumor model was developed by subcutaneously injecting Erlotinib resistant HCC827 cells to the right flank into nude mice. Oral treatment with free CFM-4.16 drug and with CFM-4.16 SMEDDS at 40 mg/kg body weight was started after the tumor volume reached around 100 mm³. Six doses of CFM treatment were given every alternate day for two (2) weeks, and tumor volume was measured at the end of three (3) weeks. As seen in FIG. 2A, the CFM-4.16 formulation showed significantly lower tumor volume compared to both the control group and the free drug group.

Figure 2B:
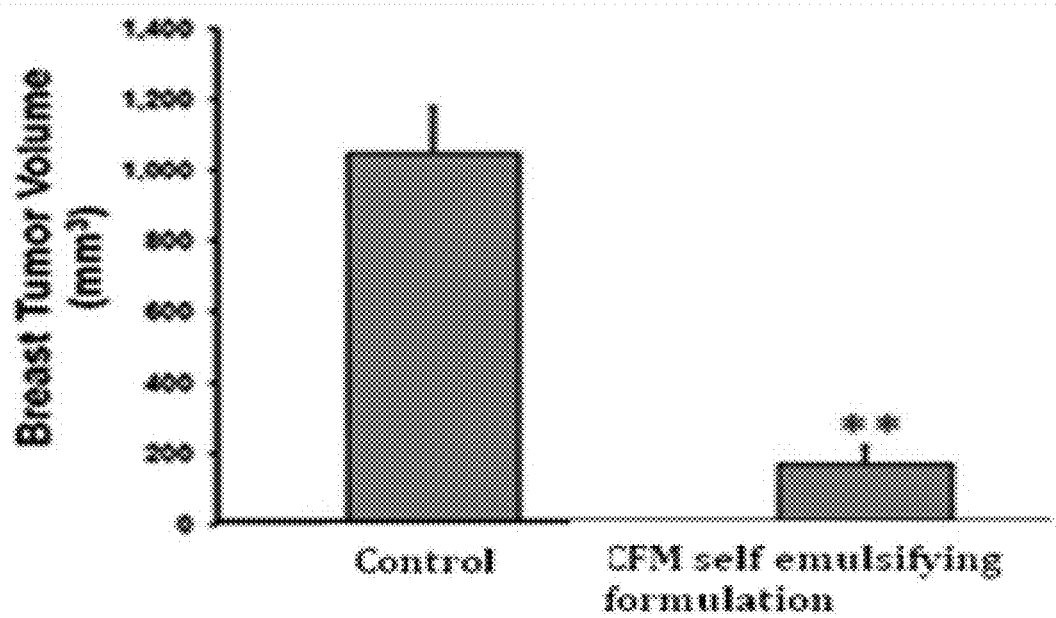
FIG. 2B is a graphical illustration depicting breast tumor volume in tumor-bearing nude mice after CFM-4.16 free drug and CFM-4.16 solid self-emulsifying formulation.
Figure 2C:
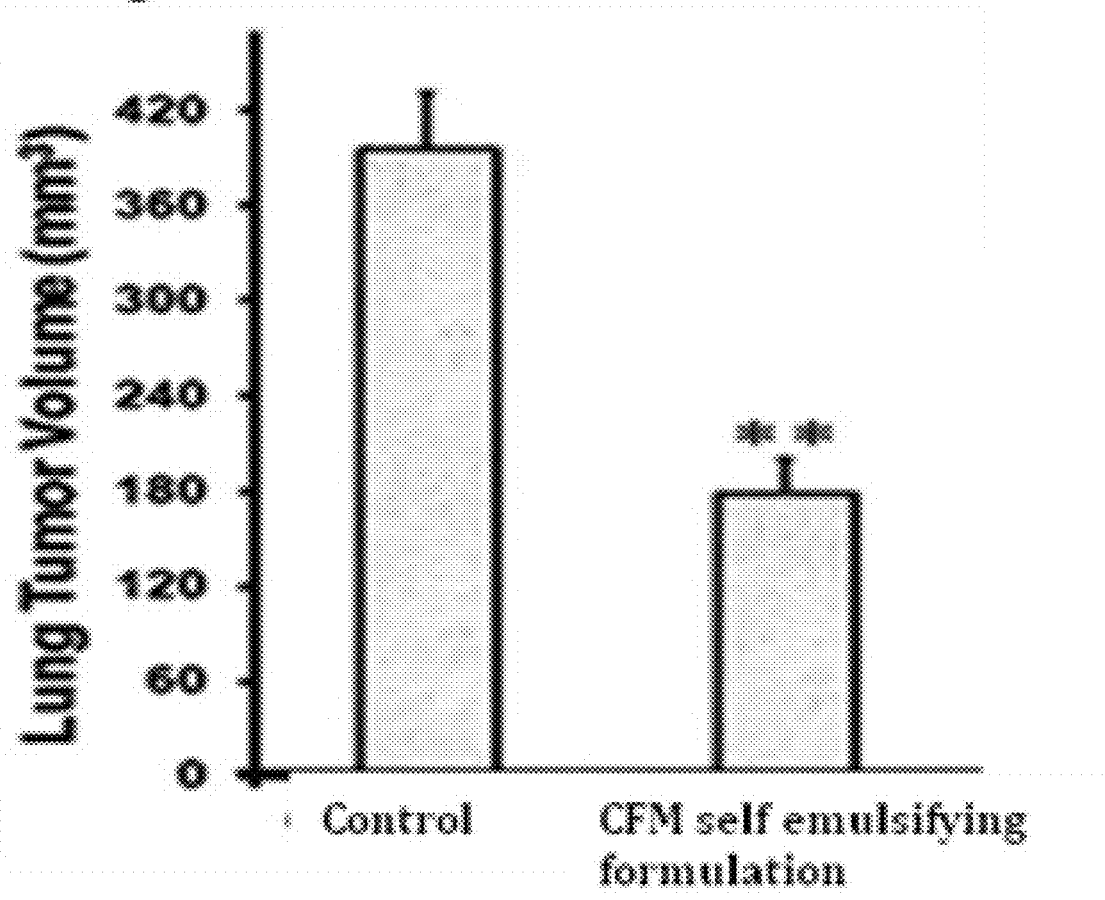
FIG. 2C is a graphical illustration depicting volume of lung tumor (A549 orthotopic xenograft lung tumor) in tumor-bearing nude mice after CFM-4.16 free drug and CFM-4.16 solid self-emulsifying formulation.

The efficacy of the current CFM-4.16 nanoparticles was also assessed against MDA-MB231 breast xenografts (see FIG. 2B) and also against lung A549 orthotopic tumors (see FIG. 2C). In each case, significant tumor regression was seen with the exemplary CFM delivery system, suggesting that the current nano-formulation was highly bioavailable and potent. Further, as seen, the current CFM compounds were found to be active at least against breast cancer, triple negative breast cancer, and resistant and non-resistant lung cancer, though other forms of cancer are contemplated herein as well.

Study 2

A more extensive study was conducted on the treatment of triple negative breast cancers (TNBCs) using CFM, and this study will be discussed herein. Doxorubicin and Cisplatin are frontline therapeutics for treatment of the TNBCs. Emergence of drug-resistance often contributes to failure of drugs and poor prognosis, and thus necessitates development of new and improved modalities to treat TNBCs. Chemotherapy-resistant TNBC cells were generated and characterized herein following their culture in chronic presence of Doxorubicin or Cisplatin. Their viabilities were tested to determine whether they were inhibited by a novel class of CFM compounds.

Analogs of parent compound CFM-4 were obtained through structure-activity based medicinal chemistry studies. CFM-4.16, a novel analog of CFM-4, caused superior inhibition of viability of TNBC cells when used in combination with doxorubicin. Doxorubicin and cisplatin inhibited viabilities of parental cells with GI50 dose of 0.02-0.1 µM and 1.65 µM, respectively. The GI50 dose of doxorubicin for doxorubicin-resistant TNBC cells was ≥10.0 µM. For Cisplatin-resistant cells, the GI50 dose of Cisplatin was ≥6-15.0 µM for MDA-MB-468 sublines and ≥150.0 µM for MDA-MB-231 sublines.

CFM-4.16 inhibited viability of chemotherapy-resistant TNBC cells, in part by inhibiting oncogenic cMet activation and expression, stimulating CARP-1 expression, caspase-8 cleavage and apoptosis. CFM-4.16 pretreatment enhanced anti-TNBC efficacies of inhibitors of cMet (Tevatinib) or cSrc (Dasatinib). CFM-4.16 suppressed growth of resistant TNBC cells in soft agar as well as in three-dimensional suspension cultures derived from enriched, stem-like cells. Finally, a nanolipid formulation of CFM-4.16 in combination with doxorubicin had superior efficacy in inhibiting TNBC xenograft growth. These findings collectively demonstrated the therapeutic potential of CFM-4.16 for parental and drug-resistant TNBCs.

I. Materials and Methods

A. Cells and Reagents

Routine culture and maintenance of human TNBC cell lines MDA-MB-468, MDA-MB-231, HCC1937, and Hs578T, the SKBR-3 human breast cancer (HBC) cells that lack estrogen receptor, have mutant p53, and overexpress Her-2, cervical cancer HeLa, and human malignant pleural mesothelioma (MPM) H2461 and H2373 was carried out essentially as described before [Puliyappadamba et al.; Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627]. Human TNBC CRL2335, BT-20, and HCC-1806 cells were purchased from ATCC, and were kindly provided by Drs. Julie Boerner, and Kaladhar Reddy Departments of Oncology and Pathology, respectively, Wayne State University, Detroit, Mich. The CRL2335, BT-20, and HCC-1806, were routinely cultured essentially as described before [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627; Yin S, Rishi A K, Reddy K B. Anti-estrogen resistant breast cancers cells are sensitive to cisplatin plus TRAIL treatment. Oncology Reports. 2015; 33:1475-80]. Herceptin-resistant SKBR-3 HBC cells were kindly provided by Dr. Rita Nahta, Emory University Cancer Center, Atlanta, Ga., and cultured essentially as described [Nahta R, Yuan, LXH, Du Y, Esteva F J. Lapatinib induces apoptosis in trastuzumab-resistant breast cancer cells: effects on insulin-like growth factor I signaling. Mol Cancer Ther. 2007; 6:667-674]. 4T1, a highly metastatic murine breast cancer cell line derived from a spontaneously arising BALB/c mammary tumor were obtained from the Karmanos Cancer Institute (KCI) and maintained essentially as described before [Dexter D L, Kowalski H M, Blazar B A, Fligiel Z, Vogel R, Heppner G H. Heterogeneity of tumor cells from a single mouse mammary tumor. Cancer Res. 1978; 38:3174-81; Aslakson C J, Miller F R. Selective events in the metastatic process defined by analysis of the sequential dissemination of subpopulations of a mouse mammary tumor. Cancer Res. 1992; 52:1399-1405]. The human umbilical vein endothelial cells (HUVECs) and the in vitro angiogenesis assay kit was purchased from Lonza Walkersville Inc., Walkersville, Md. and Chemicon International Inc., Temicula, Calif., respectively. The HUVECs were maintained in a specified media (EGM Bullet kit; Lonza Walkersville Inc.) per the manufacturer suggested guidelines. All the cell culture media were also supplemented with 10% FBS, 100 units/ml of penicillin, and 100 µg/ml of streptomycin, and the cells were maintained at 37° C. and 5% $CO_2$ [Puliyappadamba et al.; Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627; Jamal S, Cheryan V T, Muthu M, Munie S, Levi E, Ashour A E, Pass H I, Wali A, Singh M, Rishi A K. CARP-1 functional mimetics are a novel class of small molecule inhibitors of malignant pleural mesothelioma cells. PLos One. 2014; 9:e89146].

DMEM, RPMI-1640 medium, penicillin and streptomycin were purchased from Invitrogen Co. (Carlsbad, Calif.), and dimethyl sulfoxide (DMSO) was purchased from Fischer Scientific (Fair Lawn, N.J.). FBS was purchased from Denville Scientific Inc. (Metuchen, N.J.), and 3-4, 5-dimethyltiazol-2-yl-2.5-diphenyl-tetrazolium bromide (MTT), research grade Cisplatin, and Anti-β-actin mouse monoclonal antibody were purchased from Sigma-Aldrich (St. Louis, Mo.). Cisplatin was dissolved in phosphate buffered saline. Enhanced Chemiluminescence Reagent was purchased from Amersham Biosciences (Piscataway, N.J.) and the Protein Assay Kit was purchased from Bio-Rad Laboratories (Hercules, Calif.). CFM-4 was obtained from ChemDiv, San Diego, and was dissolved in DMSO at a stock concentration of 50 mM and stored at −20° C. Clinical grade Adriamycin (ADR), Cisplatin, and Herceptin were obtained from Karmanos Cancer Institute Pharmacy, Detroit, Mich. while the research grade ADR along with dual Src and Bcr-Abl inhibitor Dasatinib, and c-Met inhibitor Tevatinib were purchased from SelleckChem, Boston, Mass. and dissolved in manufacturer suggested solvent (water or DMSO) to obtain appropriate stocks that were stored at −20° C. until needed.

Generation and characterization of the anti-CARP-1/CCAR1 rabbit polyclonal antibodies have been described elsewhere [Rishi A K, Zhang L, Boyanapalli M, Wali A, Mohammad R M, Yu Y, Fontana J A, Hatfield J S, Dawson M I, Majumdar A P N, Reichert U. Identification and characterization of a Cell-Cycle and Apoptosis Regulatory Protein [CARP]-1 as a novel mediator of apoptosis signaling by Retinoid CD437. J Biol Chem. 2003; 278:33422-33435]. The mouse monoclonal antibodies for α-tubulin and βCatenin were obtained from Calbiochem and Millipore (Billerica, Mass.), respectively. Anti-cyclin B1, anti phospho-JNK (Threonine183/Tyrosine185) G9, caspase-8, and cleaved PARP mouse monoclonal antibodies, phospho-STAT3 (Y705), phospho-MKK4 (S257), total STAT3, Klf4, Sox2, anti-MET, c-myc, anti-JNK (56G8) rabbit monoclonal antibodies, and phospho-MET (Y1234/1235), Oct4, AKT, PARP, mToR, p70S6K, MKK4, phospho and total p38α/β SAPK rabbit polyclonal antibodies were obtained from Cell Signaling Technology (Beverly, Mass.). The On-Target plus SiRNAs for knockdown of CARP-1/CCAR1 were purchased from Dharmacon (ThermoFisher).

B. Chemical Synthesis of CFM-4 Analogs

Data from an initial SAR survey of 35 commercially available analogs of CFM-4 was used to guide the design of additional analogs. Optimal R1, X and R2 substitutions on the CFM-4 template established to date are presented in Table 2.

TABLE 2

List and chemical modifications of CFM-4 analogs 4.7-4.18.

| CFM | $R^1$ | $R^2$ | $R^3$ | $R^4$ |
|---|---|---|---|---|
| 4 | H | 2-Cl—Ph—CH$_2$ | H | H |
| 4.7 | H | 4-Cl—Ph—CH$_2$ | H | H |
| 4.8 | H | 2-napthyl-CH$_2$ | H | H |
| 4.9 | H | 3-Cl—Ph—CH$_2$ | H | H |
| 4.10 | H | 2-pyr—CH$_2$ | H | H |
| 4.11 | H | 2-Cl—Ph—CH$_2$ | MeO | H |
| 4.12 | H | 2-MeO—Ph—CH$_2$ | H | H |
| 4.13 | H | 8-quinolinyl-CH$_2$ | H | H |
| 4.14 | 2-CH$_3$ | 2-Cl—Ph—CH$_2$ | H | H |
| 4.15 | H | 2-Cl—Ph—CH$_2$ | Cl | H |
| 4.16 | 3-Cl | 2-Cl—Ph—CH$_2$ | H | H |
| 4.17 | 3-OCH$_3$ | 2-Cl—Ph—CH$_2$ | H | H |
| 4.18 | H | 2-Cl—Ph—CH$_2$ | H | CH$_3$ |

Several R3 substituents were also generated on the aromatic ring (Cl, Br, alkyl and NO2), and all were well tolerated. Synthesis of structural analogs of CFM-4 from diverse isatins and thiosemicarbazides was carried out essentially as described before [Bursavich M G, Gilbert A M, Lombardi S, Georgiadis K E, Reifenberg E, Flannery C R, Morris E A. 5'-Phenyl-3'H-spiro[indoline-3,2'-[1,3,4] thiadiazol]-2-one inhibitors of ADAMTS-5 (Aggrecanase-2) Bioorg. Med. Chem. Lett. 2007; 17:5630-5633] followed by their screening for biological activity in cells in vitro by MTT assays.

C. Generation of Drug-Resistant TNBC Cells

Human TNBC MDA-MB-468 and MDA-MB-231, and mouse TNBC 4T1 cells were cultured in the chronic presence (>10 months) of Doxorubicin. The parental, wild-type cells were initially treated with 200 nM Doxorubicin for 2-3 weeks, followed by escalation to 400 nM, 1 µM, and 2 µM doses over a period of 3-4 weeks for each dose till resistance developed and the cells became well adapted to growth in 1 µM dose of Doxorubicin for their routine culture. In the case of Cisplatin however, the human TNBC MDA-MB-468 and MDA-MB-231 were initially cultured in continuous presence of 1 µM Cisplatin for 3-4 weeks, and the dose was escalated to 1.5 µM and 3 µM over periods of 3-4 weeks for each dose till resistance developed and cells became adapted to routine culture in 3 µM dose. Subsequent, routine maintenance of the resistant cells in the presence of the respective drug was continued and multiple, resistant sublines for each of the TNBC cells were isolated and characterized for their growth inhibitory $(GI)_{50}$ dose of respective therapeutic by the MTT-based viability assays as below.

D. MTT and Western Blot Assays

In vitro inhibition of cell growth was assessed by MTT (3-[4, 5-dimethyltiazol-2-yl]-2.5-diphenyl tetrazolium bromide) reagent. Cells ($5 \times 10^3$) were seeded in a 96-well culture plate and subsequently treated with respective agents at different concentrations as mentioned. Control cells were treated with 0.1% DMSO in culture medium. After treatment, the cells were incubated with 1 mg/ml of MTT reagent at 37° C. for 2-4 hours and then MTT was removed and 50 µL of DMSO was added, followed by colorimetric analysis using a multi-label plate reader at 560 nm (Victor3; PerkinElmer, Wellesley, Mass., USA).

For protein expression analysis, Western blot (WB) experiments were performed according to the standard procedures. The cells were either untreated or treated with various agents either alone or in combinations as indicated. Following treatment durations, the cells were lysed in cell lysis (10x) buffer (#9803; cell signaling) containing 0.1% of protease and phosphatase inhibitor cocktail (Sigma) for 20 min at 4° C. The lysates were centrifuged at 14,000 rpm at 4° C. for 15-20 min to remove debris. Protein concentrations of whole cell lysates were determined using the Protein Assay Kit. Supernatant proteins, 50-100 µg from each sample, were separated by SDS-polyacrylamide gel electrophoresis (SDS-PAGE) and transferred to polyvinylidene difluoride (PVDF) membrane (Bio-rad, Hercules, Calif.) by standard procedures. The membranes were hybridized with primary antibodies followed by incubation with appropriate secondary antibodies using manufacturer suggested dilutions. The antibody-bound proteins were visualized by treatment with the chemiluminescence detection reagent according to manufacturer's instructions, followed by exposure to X-ray film (Denville Scientific Inc.). The same membranes were re-probed with the anti-β-actin or anti-α-tubulin antibody, which was used as an internal control for protein loading.

E. Cell Migration and Clonogenic Assays

The TNBC cells migration in the absence or presence of CFMs was measured by the "scratch/wound healing" assay. Cells were seeded in a 6-well plate (~10,000 cells/well), and when attached, a scratch was created in the cell monolayer using sterile pipette tip. The cells were then allowed to continue growing in the absence (Control) or presence of noted dose of each of the agents for indicated time periods. The cells were photographed at the beginning and at regular intervals during the treatment period, and the images from control cells were compared with the treated cells to determine the migration of the cells essentially as described before [Liang C C, Park A Y, Guan J L In vitro scratch assay: a convenient and inexpensive method for analysis of cell migration in vitro. Nat Protoc. 2007; 2:329-33]. The photomicrographs of the cells were recorded under different magnifications utilizing Zeiss microscope with attached 35 mm camera.

F. Clonogenic Assay

A soft-agar sandwich assay was performed. Cells were sandwiched between 0.6% and 0.3% agarose in DMEM medium containing 5% FBS in a six-well chamber (500 cells/chamber), and treated with buffer (Control), or respective agent for noted time and dose at 37° C. humidified $CO_2$ incubator. The colonies from multiple random fields were counted, compared to control and photographed essentially as described before [Jamal S, Cheryan V T, Muthu M, Munie S, Levi E, Ashour A E, Pass H I, Wali A, Singh M, Rishi A K. CARP-1 functional mimetics are a novel class of small molecule inhibitors of malignant pleural mesothelioma cells. PLos One. 2014; 9:e891; Ashour A E, Jamal S, Cheryan V T, Muthu M, Zoheir K M A, Alafeefy A M, Abd-allah AR, Levi E, Tarca A L, Polin L A, Rishi A K. CARP-1 functional mimetics: A novel class of small molecule inhibitors of medulloblastoma cell growth. PLoS One. 2013; 8:e66733; Zhang L, Levi E, Majumder P, Yu Y, Aboukameel A, Du J, Xu H, Mohammad R M, Hatfield J S, Wali A, Adsay V, Majumdar A P N, Rishi A K. Transactivator of transcription tagged cell cycle and apoptosis regulatory protein-1 peptides suppress growth of human breast cancer cells in vitro and in vivo. Mol Cancer Ther. 2007; 6:1661-1672].

G. Formulation of CFM-4.16 Nano Lipid Carriers (CFM-4.16 NLF) and Pharmacokinetic Studies Preparation and characterization of CFM-4.16 NLF was carried out essentially as described [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627]. Briefly, appropriate amounts of CFM-4.16 were blended with Compritol 888ATO, Miglyol 812N, and Geleol, and the mixture was melted at 70° C. to form a uniform and clear oil phase. Next, an aqueous phase consisting of dispersing surfactant Tween 80 and Vitamin E TPGS in double distilled water was added drop wise to the oil phase at 70° C. and phases agitated at 5000 rpm for 5 min using tissuemiser. The coarse emulsion was then homogenized for 15 min under high pressure. The NLF preparation was then processed with NanoDebee for about 5 cycles followed by probe sonication for 5 min to reduce its size [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627; Zhang W, Liu J, Zhang Q, Li X, Yu S, Yang X, Kong J, Pan W. Enhanced cellular uptake and anti-proliferating effect of chitosan hydrochlorides modified genistein loaded NLC on human lens epithelial cells. Int J Pharm. 2014; 471:118-26].

Further surface modification of NLF preparation was carried out by mixing with appropriate amounts of the chitosan polymer (CP) essentially as described before [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627; Tian B, Luo Q, Song S, Liu D, Pan H, Zhang W, He L, Ma S, Yang X, Pan W. Novel surface-modified nanostructured lipid carriers with partially deacetylated water-soluble chitosan for efficient ocular delivery. J Pharm Sci. 2012; 101:1040-9]. Briefly, CP was dissolved in water to obtain a series of concentrations (0.25%, 0.5%, 1%, 2%, w/v), and then mixed with CFM-4 NLF dispersions. In each case, an aliquot of NLF was mingled with an equal volume of CP by adding it drop wise under continuous agitation at room temperature (20° C.) over a 30 min incubation period. The surface modified CFM-4.16 NLF formulation was subjected to drug encapsulation efficiency, measurement of particle size and zeta potential, and in vitro drug release studies following methods described previously by the current inventors [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627].

Pharmacokinetic Studies were performed in rodents (Sprague Dawley Rats) to determine the bio-availability kinetics of the CFM-4.16 NLF formulation and CFM-4.16 free drug (FD) following previously detailed protocols [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627]. Briefly, rats were fasted overnight prior to the start of experiments and randomly divided into three experimental groups receiving CFM-4.16 FD and CFM-4.16 NLF at 40 mg/kg orally and CFM-4.16 solution (CFM-4.16 sol) at 5 mg/kg by intravenous route. After the drug administration, blood samples (250 µl) were withdrawn from tail veins at 0, 0.25, 0.5, 1, 2, 4, 6, 8, 12 and 24 h, and collected directly into heparinized microvet blood collection tubes and plasma was obtained by centrifugation at 10,000 rpm for 10 min. The plasma samples were stored at −80° C. until needed for analysis. CFM-4.16 was extracted from the plasma by protein precipitation method and extracted samples were dissolved in mobile phase and samples were analyzed by HPLC. Oral bioavailability of CFM-4.16 FD and CFM-4.16 NLF along with their pharmacokinetic parameters such as area under curve (AUC), Cmax, t1/2, and tmax were estimated using non-compartmental techniques with WinNonlin® 5.0 software (Pharsight Corporation, Mountain View, Calif., USA).

H. Establishment of TNBC Cell-Derived Xenografts in Immunocompromised Mice

The experiments involving generation of TNBC cell-derived sub-cutaneous xenografts were performed according to the current inventors' previously published methods and protocols approved by the Institutional Laboratory Animal care & Use Committees at the Wayne State and Florida A&M Universities [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627; Zhang W, Liu J, Zhang Q, Li X, Yu S, Yang X, Kong J, Pan W. Enhanced cellular uptake and anti-proliferating effect of chitosan hydrochlorides modified genistein loaded NLC on human lens epithelial cells. Int J Pharm. 2014; 471:118-26; Chougule M B, Patel A R, Jackson T, Singh M. Antitumor activity of Noscapine in combination with Doxorubicin in triple negative breast cancer. PLoS One. 2011; 6:e17733]. Female, 5-weeks old NCR SCID mice with Lc Background or Balb/c nude mice were purchased from Charles River Laboratories (Horsham, Pa.). The orthotopic TNBC xenograft studies were carried out in female BALB/c Nude Mice. Following suitable acclimation of animals, $1 \times 10^6$ MDA-MB-231 TNBC cells were re-suspended in 200 µl of serum-free Hank's balanced salt solution, and implanted in the mammary fat pads using a 27-gauge needle. Tumors were allowed to grow unperturbed for 10-14 days. When tumors became palpable (200 $mm^3$), the mice were randomly assigned to treatment or control groups of six animals each. Mice were treated with Control, PBS only, CFM-4.16 NLF (40 mg/kg), Doxorubicin (5 mg/kg), or CFM-4.16 NLF+ Doxorubicin every alternate day for 2 weeks. CFM-4.16 NLF was administered by oral gavage while Doxorubicin was given by intravenous route by tail vein. One week after the last dose of drugs, animals were sacrificed and tumor tissues were collected immediately after tumor volume measurement. Tumor volumes were calculated by the modified ellipsoidal formula. Tumor volume=½(length×width). Representative tumor samples were stored at −80° C. for subsequent analysis.

For subcutaneous (sc) tumor xenograft studies, first a maximal tolerated dose for CFM-4.16 was determined in the NCR-SCID mice. For this purpose, CFM-4.16 prepared in 10% DMSO/cremophor+distilled, sterile water, and pH was adjusted to 4.5. This preparation was injected daily iv at 24 mg/kg on days 1 and 2, 30 mg/kg on days 3-9 and at 32 mg/kg on days 10-16 (some mice were switched to SC route due to swollen tail veins days 12-16) for a total dose of 482 mg/kg. A mild ataxia with some tail and leg twitching resolving within 1-2 minutes was seen. This dose/schedule produced a mild weight loss of 1.6% body weight by day 7(recovery by day 18). No other histological abnormalities were noted. Subcutaneous tumor xenografts from MDA-MB-231 TNBC cells were generated in female NCR-SCID mice as described before [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627]. When the tumors developed, mice were sacrificed, tumors were dissected, cut into small fragments and either stored in liquid N2 or dissociated to isolate tumor-derived parental and drug-resistant human TNBC cells that were subsequently cultured for 3-dimensional mammosphere assays as below. In addition, tumor fragments were transplanted sc into similarly conditioned animals (n=10 for each group) by using a 12-guage trocar. Mice were checked 3-times a week for tumor development. Once palpable tumors developed, the groups of animals were subjected to efficacy trial with CFM-4.16. The animals bearing xenografts were either untreated (Control group; 10 mice) or treated with 470 mg/kg dose of CFM-4.16 (Qd 1-19; iv administration). The tumor measurements were carried out at multiple time points during the course of treatment and observation periods. Mice were observed for changes in weight and side effects followed by measurement of tumors three times per week. The end points for assessing antitumor activity consisted of tumor weight, tumor growth inhibition (% T/C), and tumor cell kill Log10. Tumor weight (mg)=(A×B2)/2 where A and B are the tumor length and width (in mm), respectively. Tumor growth inhibition (T/C) was the median tumor weight in the treated group (T) when the median tumor weight in the control group reached 750 mg. Results was expressed as percentage. According to NCI-accepted criteria, a treatment is considered effective if T/C is <42%. Tumor growth delay (T-C) is the difference between the median time (in days) required for the treatment group tumors (T) to reach 750 mg and the median time (days) for the control group tumors to reach the same weight.

I. Three-Dimensional Mammosphere Assays

The TNBC cells were obtained from tumors derived from parental and drug-resistant cells or from a two-dimensional culture plate with ~70-80% confluence. The cells were washed twice in 1×PBS and trypsinized following established protocols. The cells were pelleted at 200×g at room temperature, and re-suspended in 5 ml of mammosphere media (DMEM/F12 supplemented with 2 mM L-glutamine, 100 U/ml penicillin, 100 U/ml streptomycin, 1×B27 supplement, 20 ng/ml recombinant human epidermal growth factor (EGF; Sigma), 10 ng/ml recombinant human basic fibroblast growth factor (bFGF; R&D Systems). The cell suspension of 5000 viable cells per ml was then seeded in an ultra-low adherent 60 mm plate and incubated at 37° C. and 5% $CO_2$ for two weeks without disturbing the plates. After the mammospheres formed, fresh media with or without 10 µM CFM-4.16 was added and the cells incubated for additional 24 h at 37° C. and 5% $CO_2$. The mammospheres in the untreated and treated plates were photographed, and the cells were then dissociated to determine their viabilities by the MTT assay as described [Lombardo Y, de Giorgio A, Coombes C R, Stebbing J, Castellano L. Mammosphere Formation Assay from Human Breast Cancer Tissues and Cell Lines. J. Vis. Exp. 2015; 97: e52671. doi:10.3791/52671].

J. Statistical Analysis

In some instances, statistical analysis was performed using unpaired Student's t-test. A p-value less than 0.05 between treatment groups was considered significantly different.

II. Results

A. CFM-4.16, a Novel CFM-4 Analog, is a Potent Inhibitor of TNBC Cells

Figure 3A:
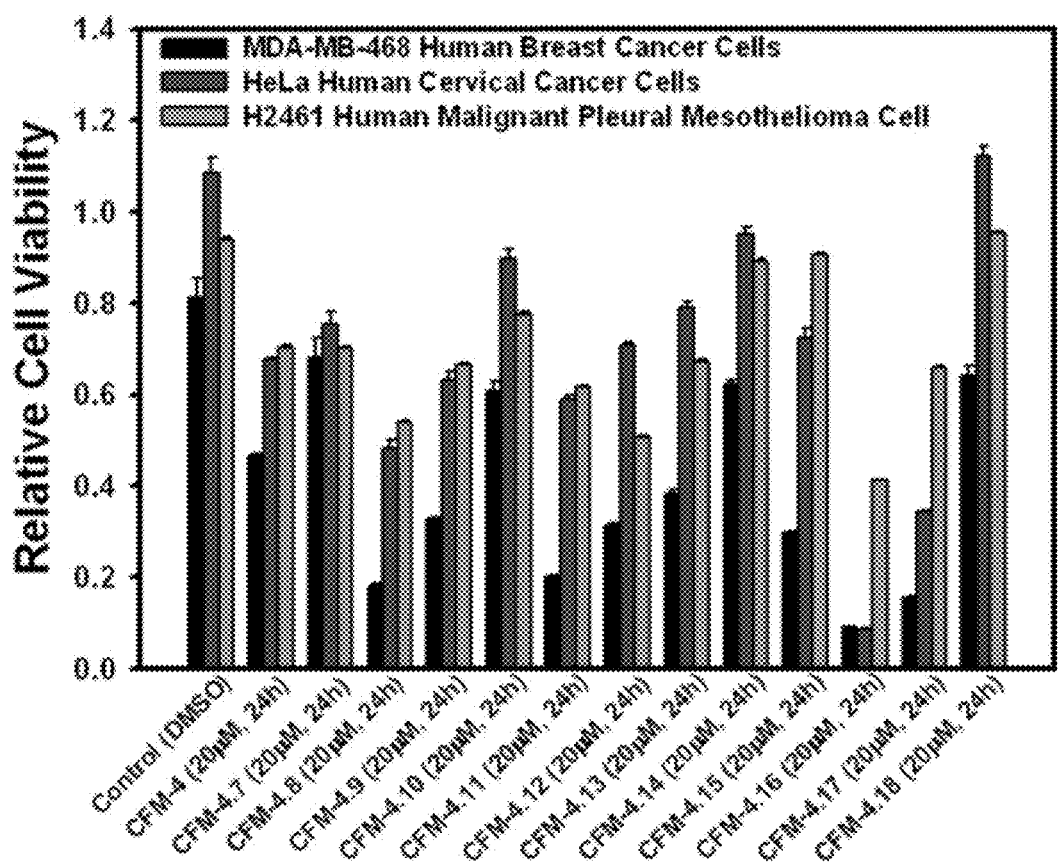
FIG. 3A shows results of cell lines treated with DMSO (control) and with various CFMs for the indicated dose and time. Cell viability was determined by MTT assay. The data in the histograms represent means of three independent experiments; bars, S. E.
Figure 3B:
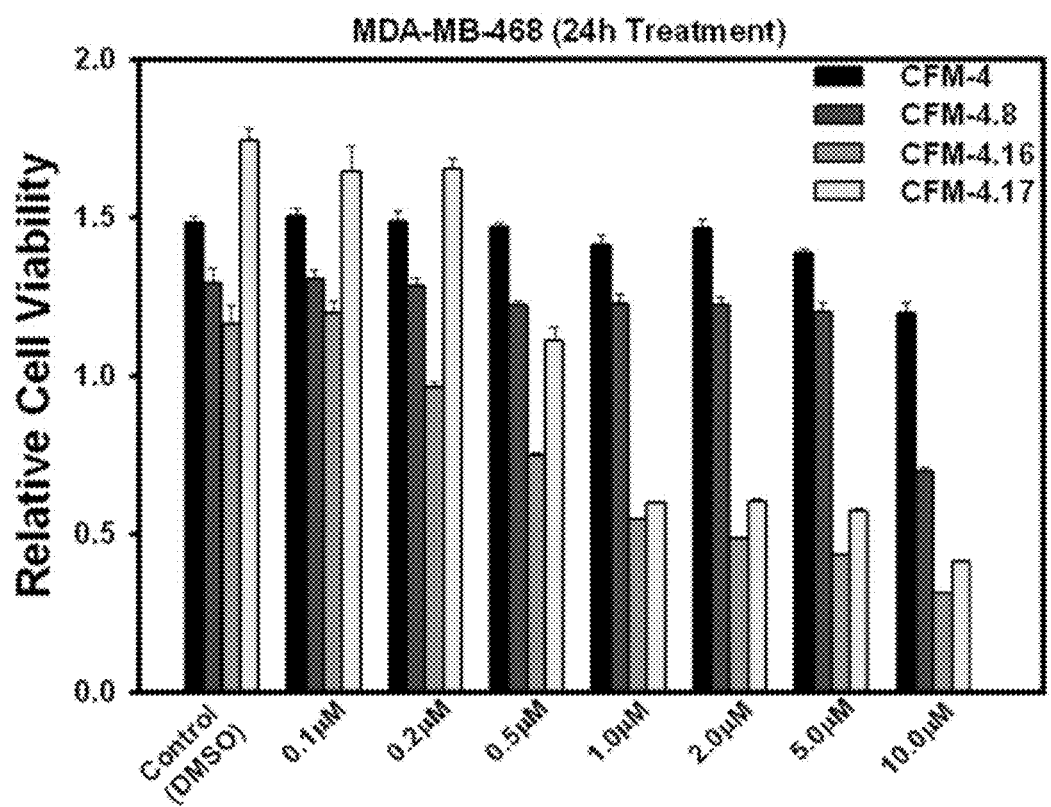
FIG. 3B shows results of cell lines treated with DMSO (control) and with various CFMs for the indicated dose and time. Cell viability was determined by MTT assay. The data in the histograms represent means of three independent experiments; bars, S. E.
Figure 4A:
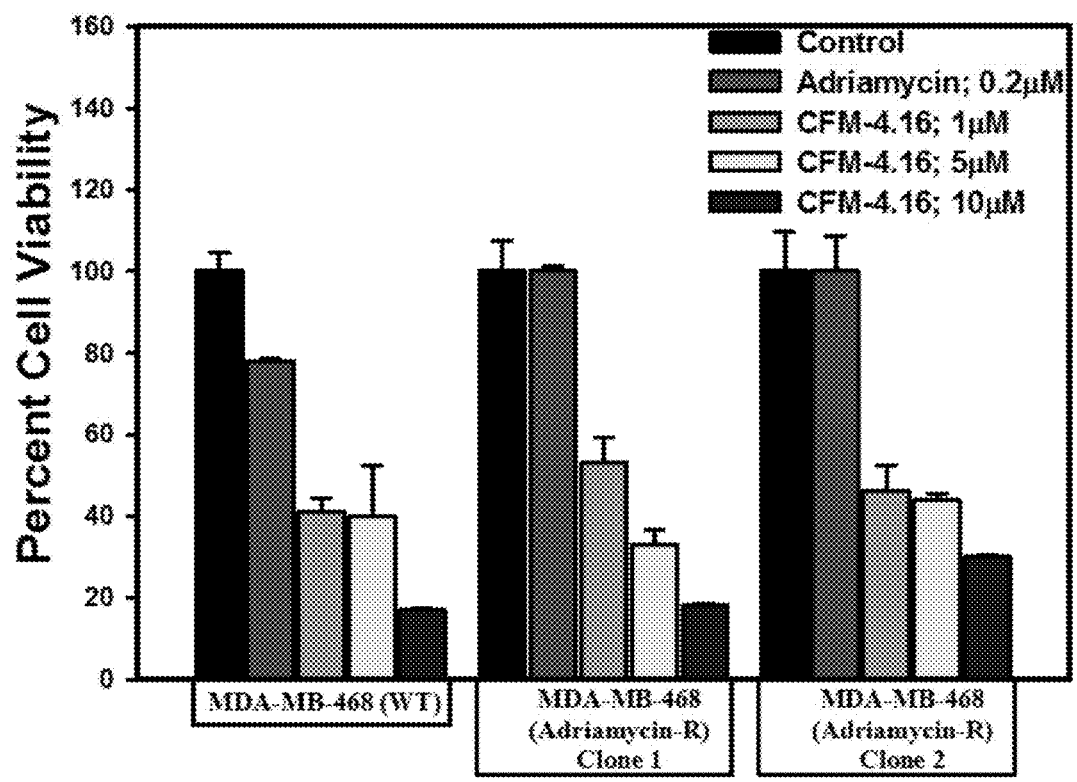
FIG. 4A is a graphical illustration showing that indicated parental and their respective drug resistant TNBC cells were either untreated (Control) or treated with noted doses of Adriamycin or CFM-4.16 for 12 h. Cell viability was determined by MTT assay. The histogram columns represent means of three independent experiments; bars, S. E.
Figure 4B:
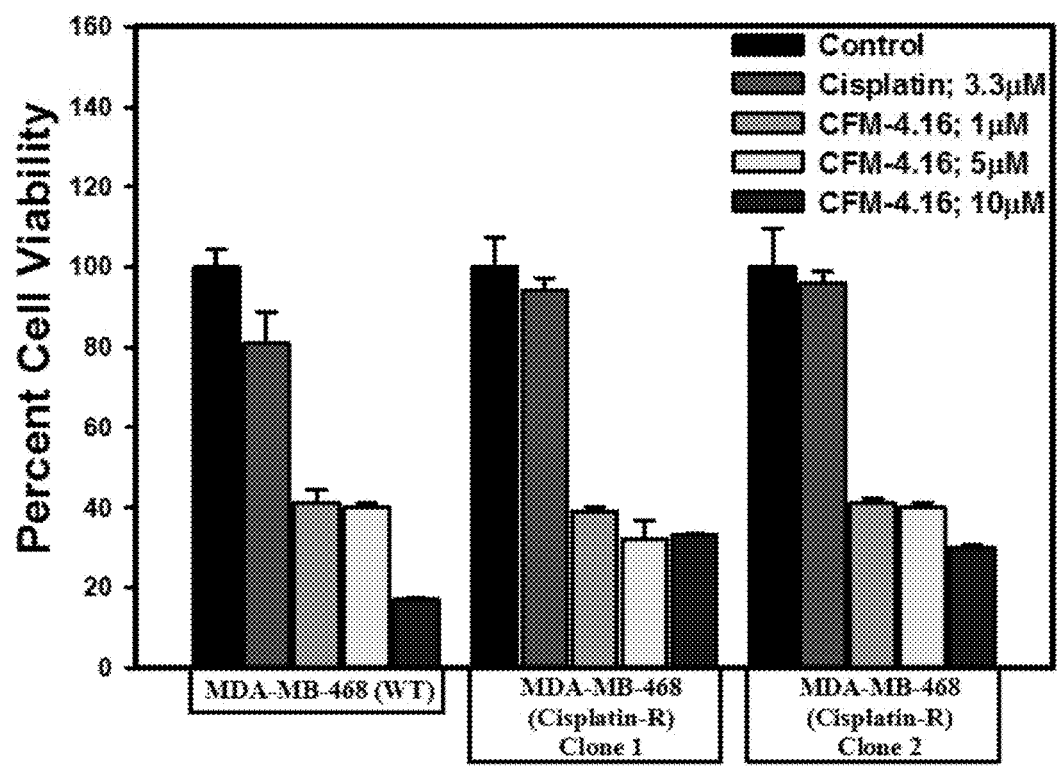
FIG. 4B is a graphical illustration showing that indicated parental and their respective drug resistant TNBC cells were either untreated (Control) or treated with noted doses of Adriamycin or CFM-4.16 for 12 h. Cell viability was determined by MTT assay. The histogram columns represent means of three independent experiments; bars, S. E.
Figure 4C:
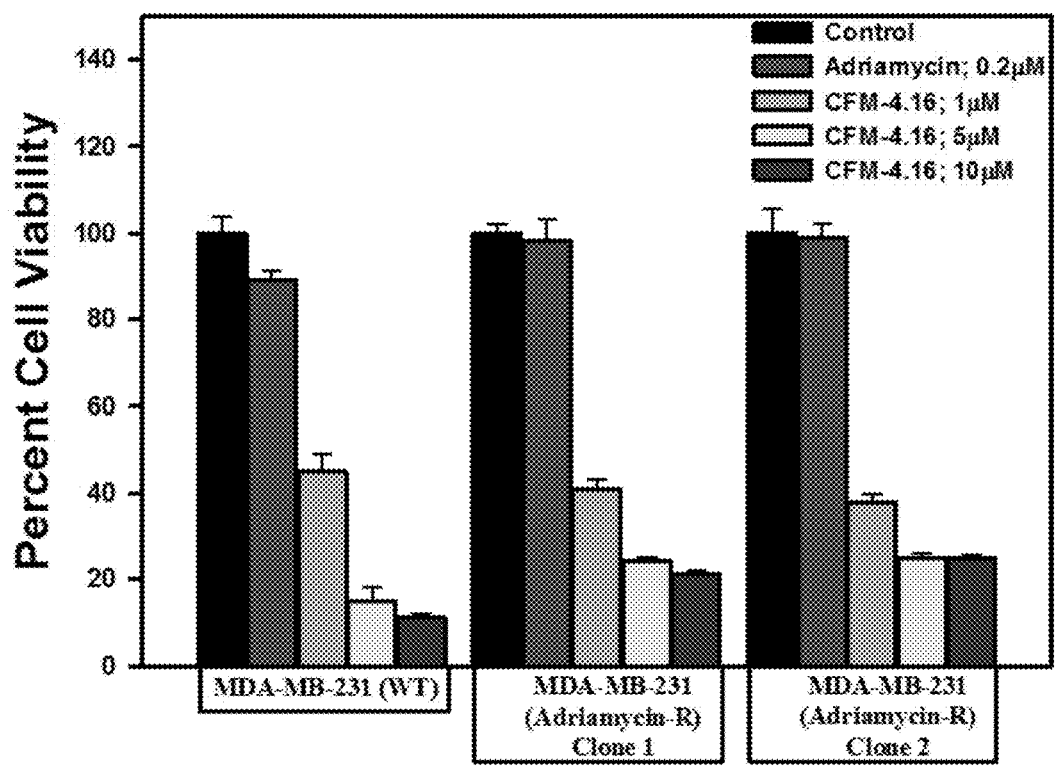
FIG. 4C is a graphical illustration showing that indicated parental and their respective drug resistant TNBC cells were either untreated (Control) or treated with noted doses of Adriamycin or CFM-4.16 for 12 h. Cell viability was determined by MTT assay. The histogram columns represent means of three independent experiments; bars, S. E.
Figure 4D:
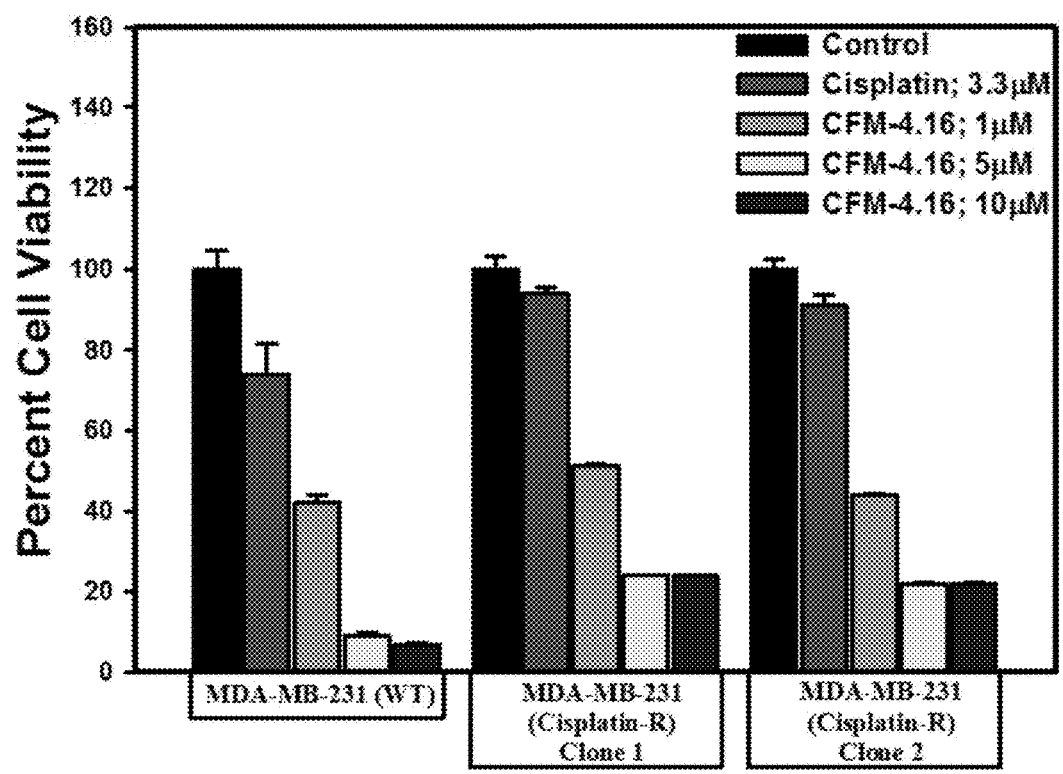
FIG. 4D is a graphical illustration showing that indicated parental and their respective drug resistant TNBC cells were either untreated (Control) or treated with noted doses of Adriamycin or CFM-4.16 for 12 h. Cell viability was determined by MTT assay. The histogram columns represent means of three independent experiments; bars, S. E.
Figure 4E:
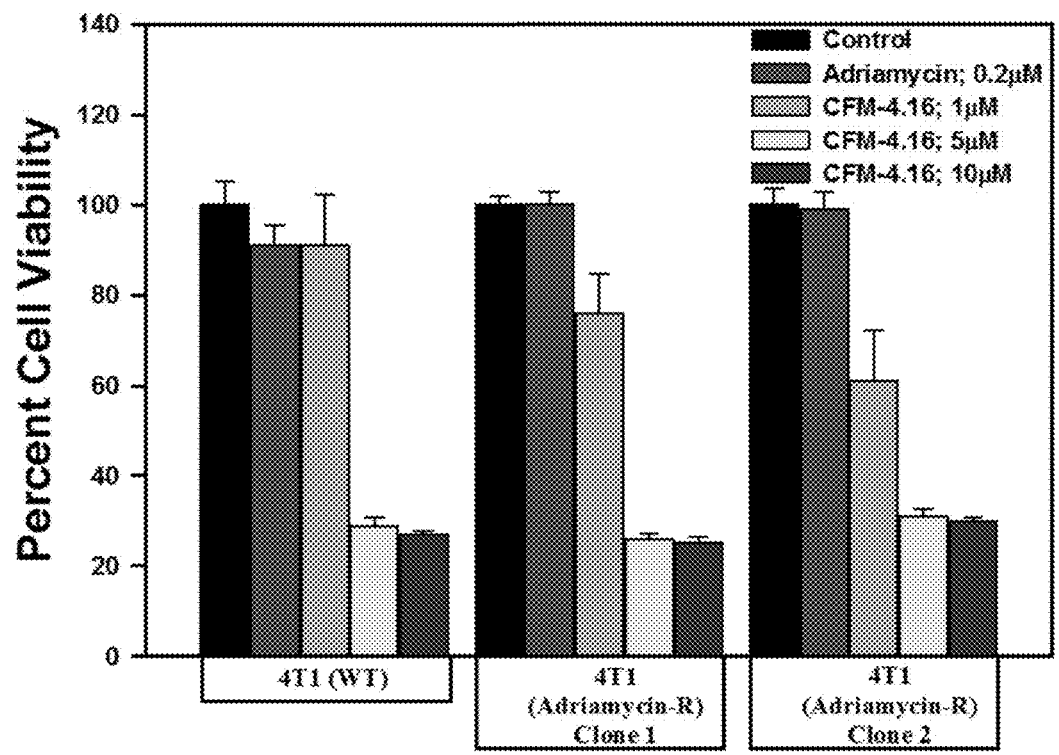
FIG. 4E is a graphical illustration showing that indicated parental and their respective drug resistant TNBC cells were either untreated (Control) or treated with noted doses of Adriamycin or CFM-4.16 for 12 h. Cell viability was determined by MTT assay. The histogram columns represent means of three independent experiments; bars, S. E. Overall.

The current inventors' previous studies have indicated cancer cell growth inhibitory properties of CFMs in particular CFM-4 and CFM-5 [Puliyappadamba et al.]. These compounds although were soluble in DMSO, the intravenous administration of DMSO+cremophor preparations of CFM-4 failed to inhibit growth of xenografted TNBC tumors in SCID mice [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627]. A nanolipid formulation of CFM-4 (CFM-4 NLF) however resulted not only in increased systemic bioavailability of this compound, the oral administration of this NLF inhibited growth of orthotopically transplanted xenografts of human TNBC as well as non-small cell lung (NSCLC) cancer cells [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627]. On the basis of these findings, it was speculated that solubility and/or potency of the CFM-4 scaffold could be improved for its utility as a novel anti-TNBC molecule. To address this possibility, twelve (12) additional analogs of CFM-4 (Table 2) were synthesized using medicinal chemistry based structure activity relationship (SAR) studies. Each of the analog was suspended in DMSO, and their potency was evaluated in cell culture studies utilizing HeLa cervical cancer, MDA-MB-468 TNBC, and H2461 malignant pleural mesothelioma (MPM) cells by MTT based assays. As shown in FIG. 3A, CFM-4.8, -4.11, -4.16, and -4.17 elicited greater inhibition of viability of TNBC cells when compared with CFM-4 at the tested dose of 20 µM for 24 h period for each compound. Interestingly, CFM-4.16 and -4.17 compounds caused greater inhibition of viability of HeLa cells while only CFM-4.16 caused a greater loss of viability of MPM cells when compared with CFM-4 at the tested doses of 20 µM for 24 h period for each compound. Moreover, a 10 µM dose of CFM-4 inhibited MDA-MB-231 and MDA-MB-468 viabilities by ~30% and 45%, respectively. A comparable, 10 µM dose of CFM-4.16 however resulted in ≥80-100% loss of cell viability of either of the TNBC cells (not shown), suggesting that CFM-4.16 was likely more potent analog for TNBC cells. Further dose response analysis revealed that either of the CFM-4.16 or -4.17 inhibited TNBC cell viabilities by 50% or higher at the doses of ≥1 µM (FIG. 3B). Additional dose response analyses revealed that although the CFM-4.16 dose for inhibition of the TNBC cells growth by 50% ($GI_{50}$) was ~2 µM, since CFM-4.16 also stimulated apoptosis (see below), its dose for inducing a 50% cytotoxic effects ($LC_{50}$) was ~7-8 µM (not shown).

Given that the frontline anti-TNBC therapeutic ADR has a molecular mass of 543.5, and the molecular mass of CFM-4.16 is 440.3, it was next tested whether and to what extent an equimolar dose of each compound will inhibit growth of the TNBC cells. For this purpose, a number of TNBC cells were treated with 5 µM dose of each agent separately or in combination for a short duration of 6 h. This experiment interestingly revealed that although each agent caused inhibition of viability of all the TNBC cells, CFM-4.16, but not CFM-4 or any of its other analogs, elicited a greater loss of cell viability of each cell line when compared with the respective, ADR-treated cell line (FIG. 3C). CFM-4.16 also enhanced ADR-mediated inhibition of viability of TNBC cells (FIG. 3C). CFM-4.16 however, failed to enhance ADR-mediated growth inhibition of a variety of other cancer cell lines tested including the MCF-7, SK-BR-3 and MDA-MB-453 breast cancer cells (not shown). The precise mechanism(s) of increased inhibition of TNBC cell growth by a combination of CFM-4.16 and ADR are yet to be clarified. The current inventors' prior studies have shown that ADR or CFM compounds function in part by stimulating CARP-1 levels, and CARP-1 expression was found necessary for apoptosis signaling by ADR as well as by CFM-4 [Rishi A K, Zhang L, Boyanapalli M, Wali A, Mohammad R M, Yu Y, Fontana J A, Hatfield J S, Dawson M I, Majumdar A P N, Reichert U. Identification and characterization of a Cell-Cycle and Apoptosis Regulatory Protein [CARP]-1 as a novel mediator of apoptosis signaling by Retinoid CD437. J Biol Chem. 2003; 278:33422-33435; Kim J H, Yang C K, Heo K, Roeder R G, An W, Stallcup M R. CCAR1, a key regulator of mediator complex recruitment to nuclear receptor transcription complexes. Molecular Cell. 2008; 31:510-519; Puliyappadamba et al.]. It is likely then that TNBC cell growth inhibitory signaling by CFM-4.16 involves mechanisms that are overlapping as well as distinct from those utilized by ADR, and the fact that the emergence of drug (ADR or Cisplatin) resistant TNBCs remain a significant and unresolved clinical problem, provided a rationale to explore whether CFM-4.16 would be suitable for inhibiting growth of drug-resistant TNBC cells.

To test whether CFM-4.16 compound will be an effective inhibitor of chemotherapy (ADR or Cisplatin)-resistant TNBC cells, a number of stable, TNBC sublines/clonal derivatives that were cultured in prolonged, chronic presence of ADR or Cisplatin, were generated essentially as detailed previously. The parental and resistant sublines were then separately subjected to MTT-based assays for determination of their respective $GI_{50}$ dose for ADR or Cisplatin (Table 3).

TABLE 3

$GI_{50}$ values of parental and drug-resistant TNBC cells. In the case of Adriamycin-resistant cells, the respective parental and resistant (ADR-R) sublines were treated with 0.1, 0.2, 1.0, 2.0, 4.0, and 10.0 μM dose of ADR. In the case Cisplatin-resistant cells, the respective parental and resistant (Cis-R) sublines were treated with 1.65, 3.30, 6.60, 16.50, 33.00, and 66.00 μM dose of Cisplatin. Percent cell viabilities were determined relative to respective DMSO-treated controls. The data in the $GI_{50}$ columns represent means of three independent experiments.

| Cisplatin (72 h) | | Adriamycin (72 h) | |
| --- | --- | --- | --- |
| Cell Line | $GI_{50}(\mu M)$ | Cell Line | $GI_{50}(\mu M)$ |
| MDA-MB-468 Wild type | ~1.65 | MDA-MB-468 Wild type | ~0.02 |
| Cis-R Clone 1-2 | ~6.6 | ADR-R Clones 1-6 | ~10.0 |
| Cis-R Clone 3 | ~12.0 | 4T1 Wild type | ~0.1 |
| Cis-R Clones 4-6 | ~15.0 | ADR-R Clones 1-6 | >10.0 |
| MDA-MB-231 Wild type | ~1.65 | MDA-MB-231 Wild type | <0.1 |
| Cis-R Clones 1-6 | ≥150.0 | ADR-R Clones 1-6 | >10.0 |

Of note is the fact that although the $GI_{50}$ dose of Cisplatin and ADR for the cisplatin-resistant MDA-MB-231 cells and the ADR-resistant MDA-MB-468 cells was ≥90-fold and ≥500-fold, respectively, higher than their wild-type, parental counterparts, the $GI_{50}$ dose of Cisplatin for the cisplatin-resistant MDA-MB-468 cells however was only 4-9-fold higher than their wild-type, parental cells (Table 3). These drug-resistant cells were then utilized to determine whether CFM-4.16 inhibits their growth and investigated the molecular mechanisms involved as detailed below.

First, the parental as well as the respective drug-resistant sublines were exposed to various doses of CFM-4.16 followed by determination of their viability by MTT-based assays. Since the $GI_{50}$ doses for ADR and Cisplatin for 72 h treatment period were <0.1 and ~1.65 μM, respectively, for both the parental TNBC cell lines (Table 3), a dose of 0.2 μM ADR or 3.3 μM Cisplatin was chosen for a shorter, 12 h treatment periods to avoid extensive loss of cell viability and/or cell death. As shown in FIGS. 4A-4E, CFM-4.16 inhibited growth of both the wild-type TNBC cells as expected. CFM-4.16 also effectively inhibited growth of the ADR or Cisplatin-resistant TNBC sublines in a dose-dependent manner, suggesting that CFM class of scaffolds could be novel precursors of molecules for treatment of TNBCs including their drug-resistant variants.

B. CFM-4.16 Promotes Apoptosis in TNBC Cells by Activating p38 MAP Kinase, c-Jun N-Terminal Kinase (JNK) and Stimulating Expression of CCAR-1/CARP-1

Figure 5A:
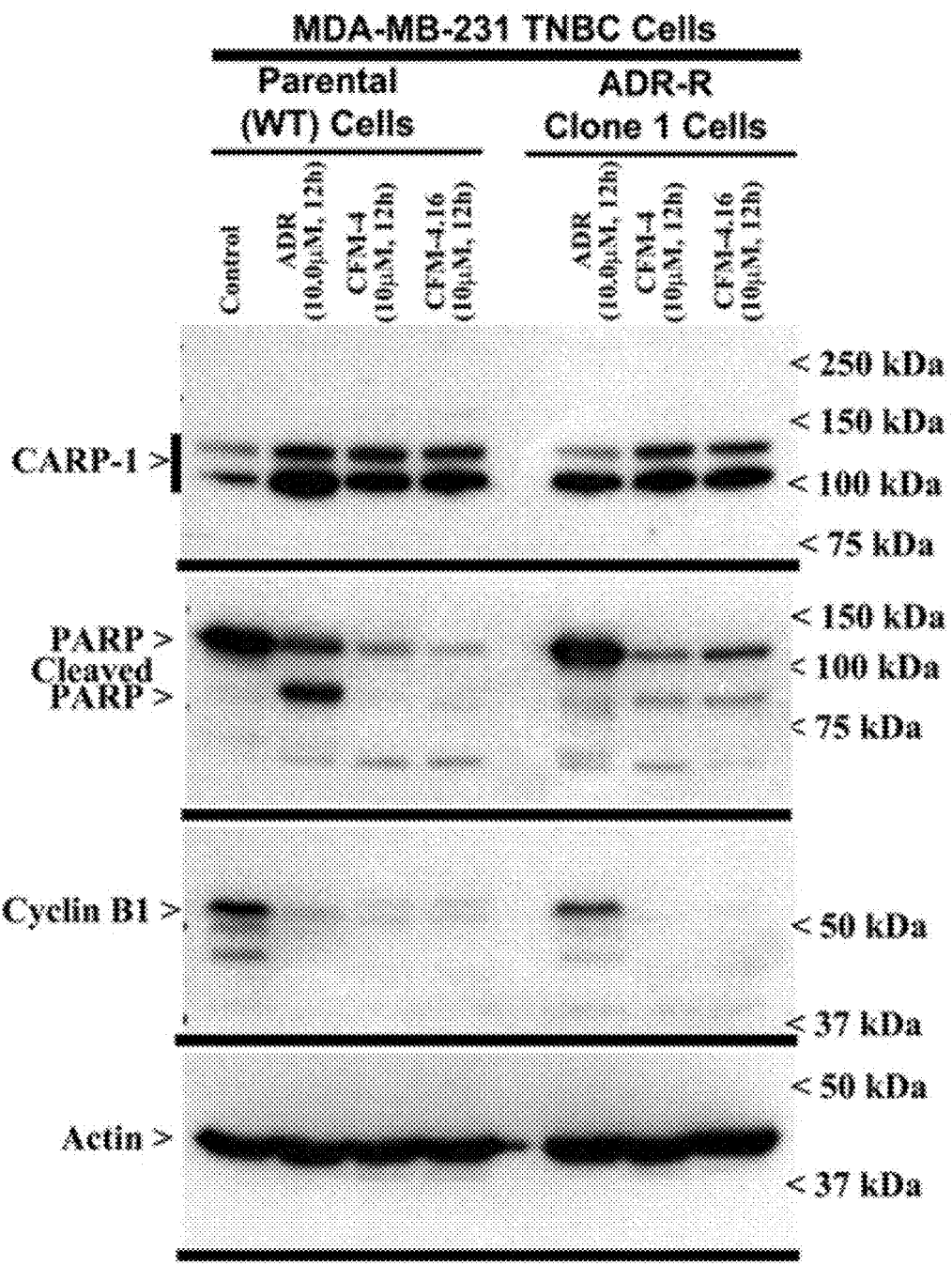
FIG. 5A is a graphical illustration showing that indicated TNBC cells were either untreated (Control), treated with ADR, CFM-4, or CFM-4.16 for noted dose and time. Cell lysates were analyzed by Western blotting (WB) for levels of CARP-1, cyclin B1, cleaved PARP and caspase-8.
Figure 5B:
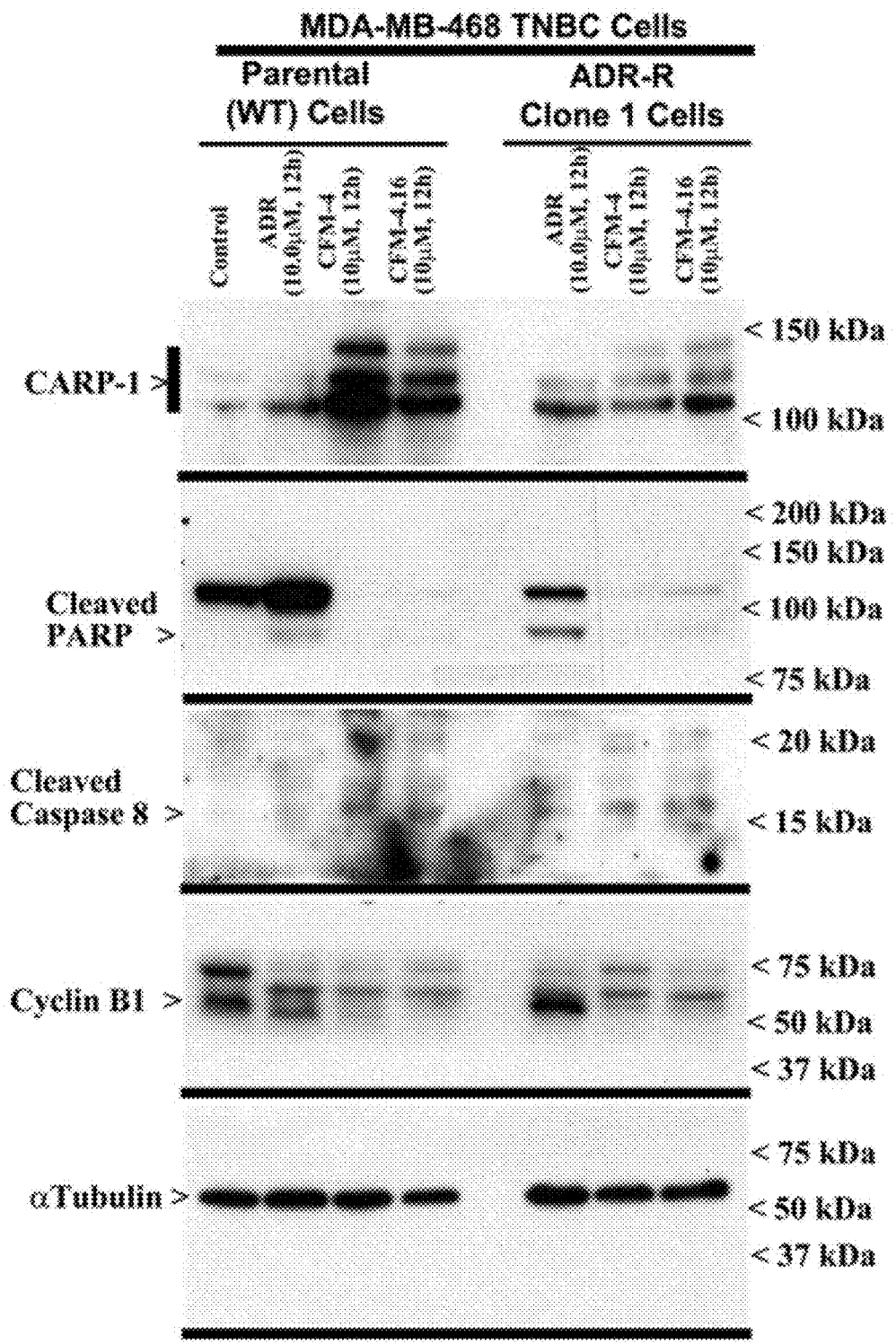
FIG. 5B is a graphical illustration showing that indicated TNBC cells were either untreated (Control), treated with ADR, CFM-4, or CFM-4.16 for noted dose and time. Cell lysates were analyzed by Western blotting (WB) for levels of CARP-1, cyclin B1, cleaved PARP and caspase-8.
Figure 5C:
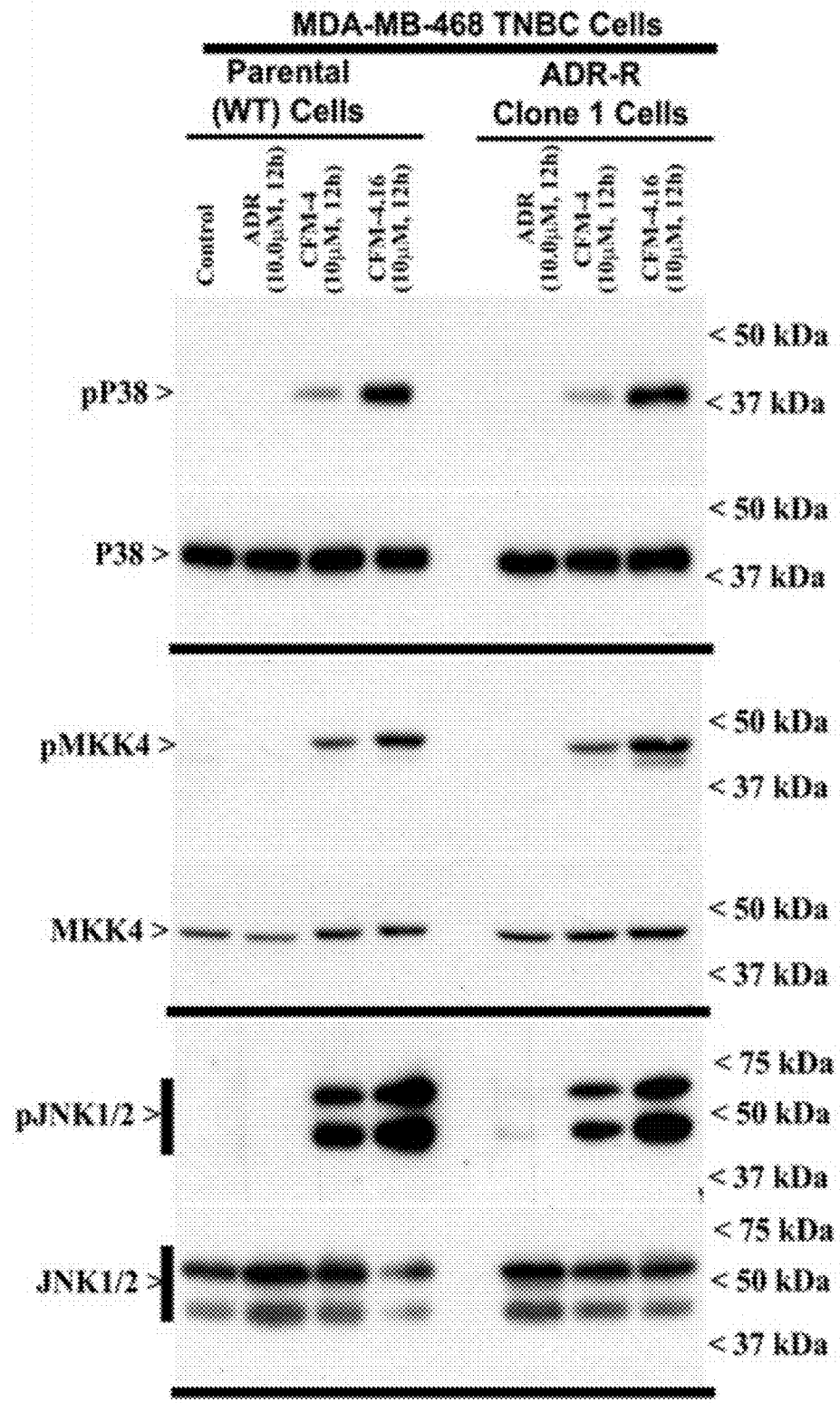
FIG. 5C is a graphical illustration showing that indicated TNBC cells were either untreated (Control), treated with ADR, CFM-4, or CFM-4.16 for noted dose and time. Cell lysates were analyzed by Western blotting (WB) for activation (phosphorylation) of pro-apoptotic p38, MKK4, and JNK1/2 SAPKs.
Figure 5D:
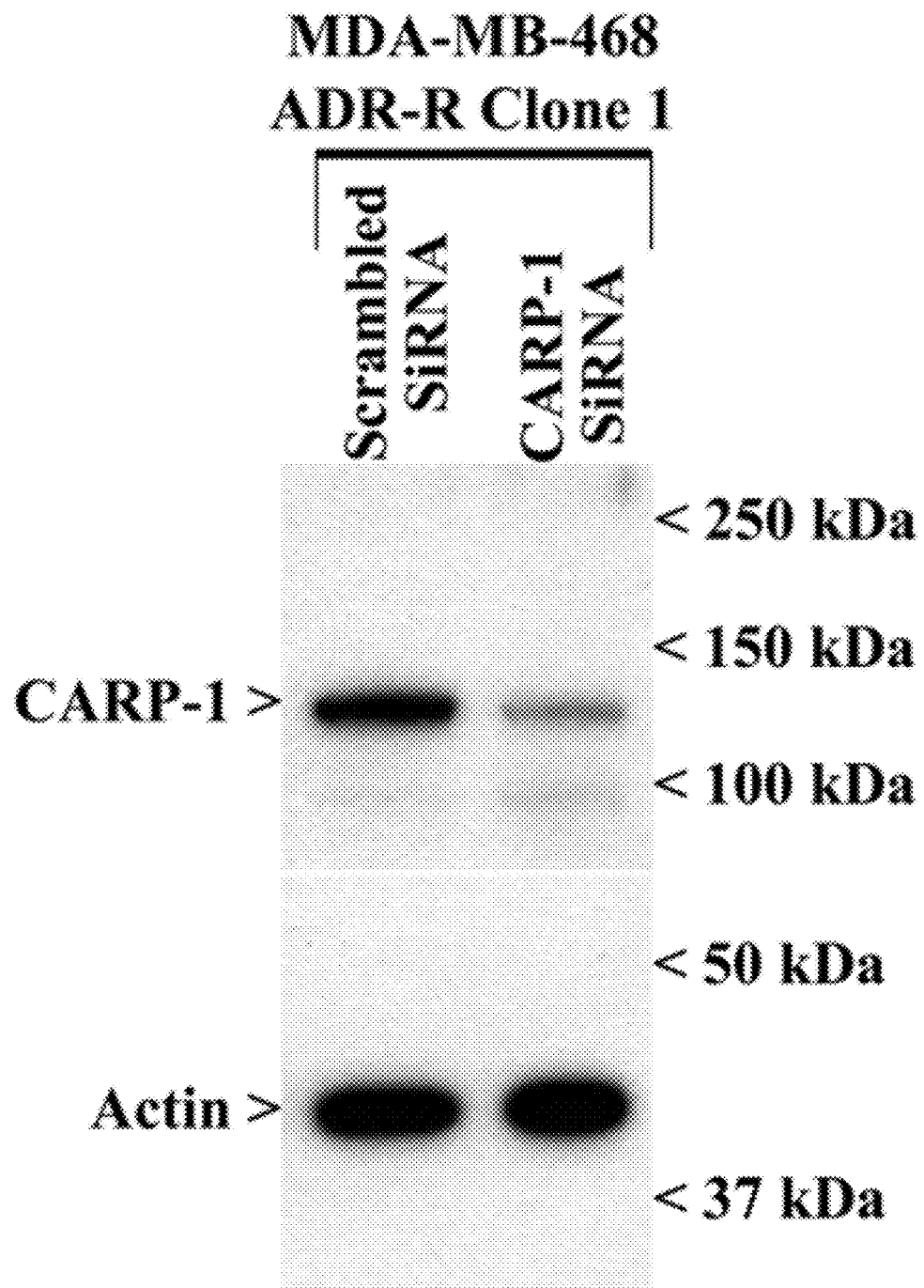
FIG. 5D shows that knockdown of CARP-1 blocks CFM-4.16 effects. Cells were transfected with 100 nM each of the scrambled or CARP-1 siRNAs for 72 h and were then either untreated (Control/DMSO), treated with CFM-4 or CFM-4.16 for noted time and dose. Cell lysates were subjected to WB as in FIG. 5B.
Figure 5E:
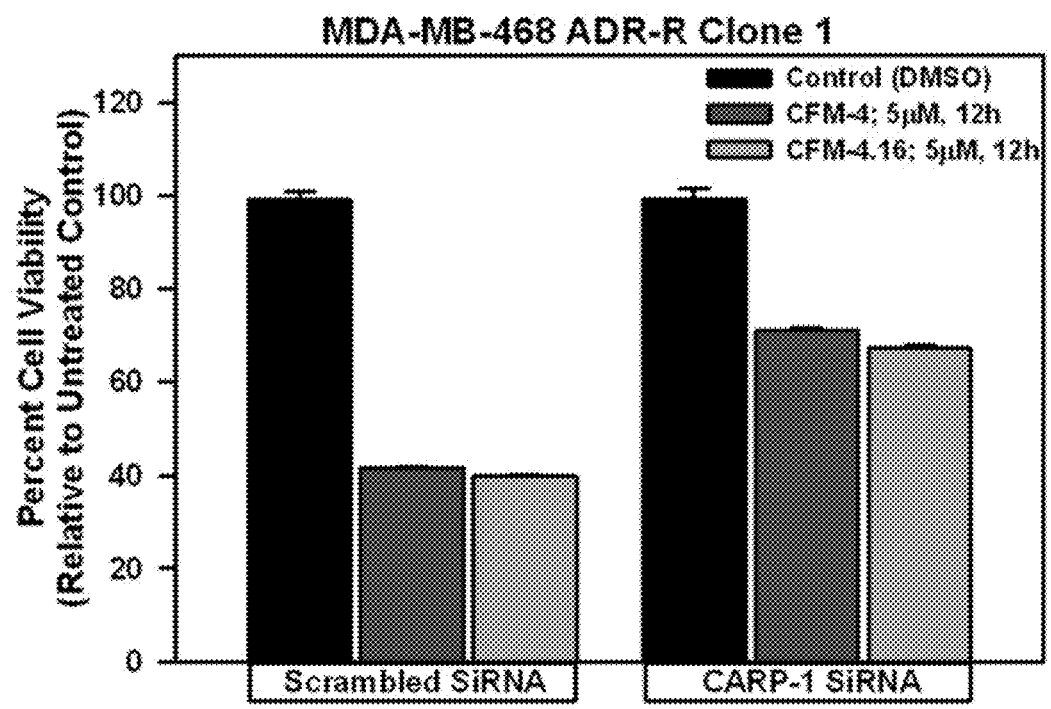
FIG. 5E shows that knockdown of CARP-1 blocks CFM-4.16 effects. Cells were transfected with 100 nM each of the scrambled or CARP-1 siRNAs for 72 h and were then either untreated (Control/DMSO), treated with CFM-4 or CFM-4.16 for noted time and dose. Cell lysates were subjected to MTT assay for determination of cell viabilities as in FIGS. 4A-4E. The histogram columns represent means of two independent experiments; bars, S. E. Overall.
Figure 6A:
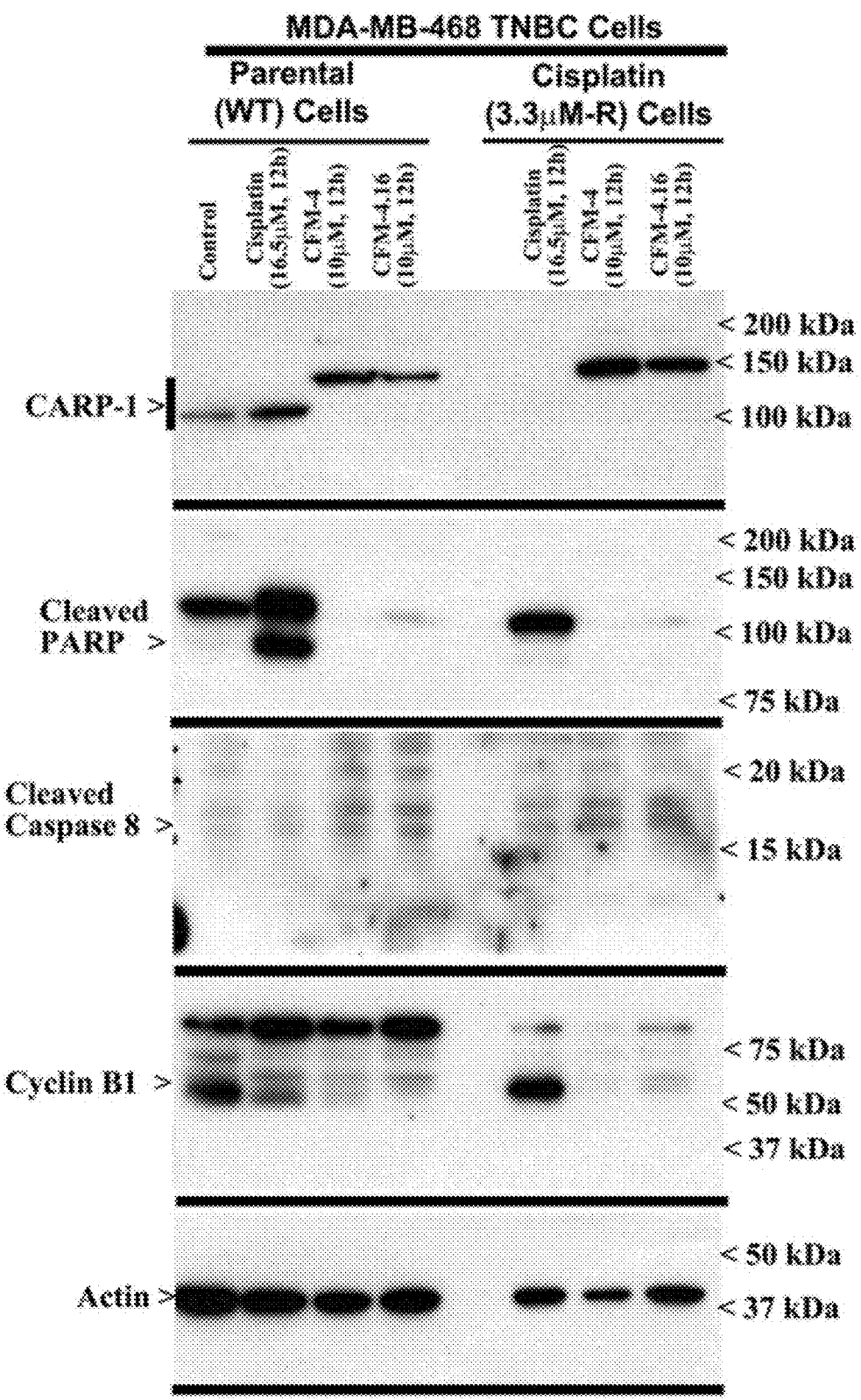
FIG. 6A shows that CFM-4.16 stimulates apoptosis in parental and Cisplatin-resistant TNBC cells in part by upregulating pro-apoptotic CARP-1. Indicated breast cancer cells were either untreated (Control), treated with Cisplatin, Herceptin, CFM-4, or CFM-4.16 for noted dose and time. Cell lysates were analyzed by Western blotting for levels of CARP-1, cyclin B1, cleaved PARP and caspase-8.
Figure 6B:
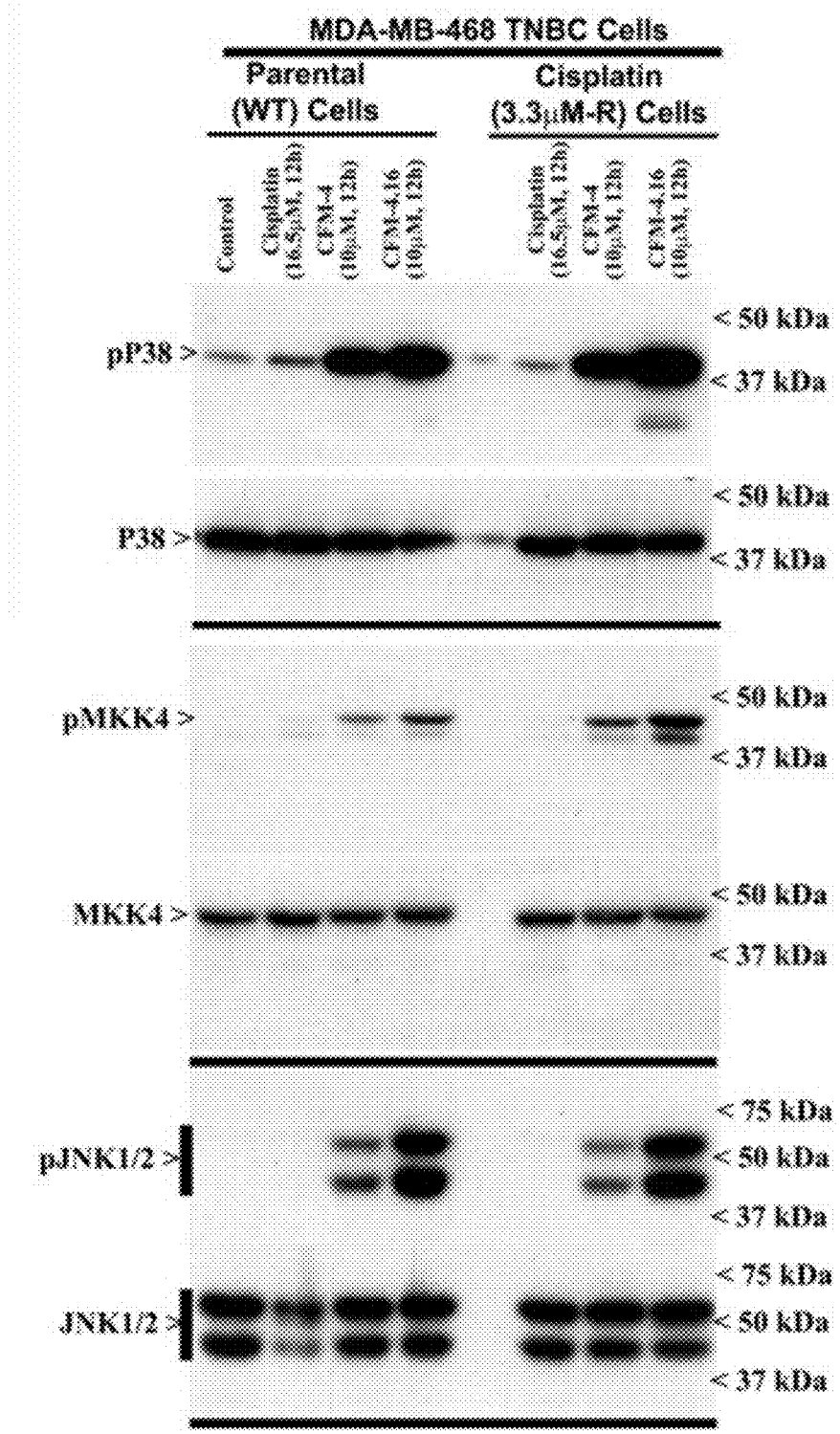
FIG. 6B shows that CFM-4.16 stimulates apoptosis in parental and Cisplatin-resistant TNBC cells in part by upregulating pro-apoptotic CARP-1. Indicated breast cancer cells were either untreated (Control), treated with Cisplatin, Herceptin, CFM-4, or CFM-4.16 for noted dose and time. Cell lysates were analyzed by Western blotting for activation (phosphorylation) of pro-apoptotic p38, MKK4, and JNK1/2 SAPKs.
Figure 6C:
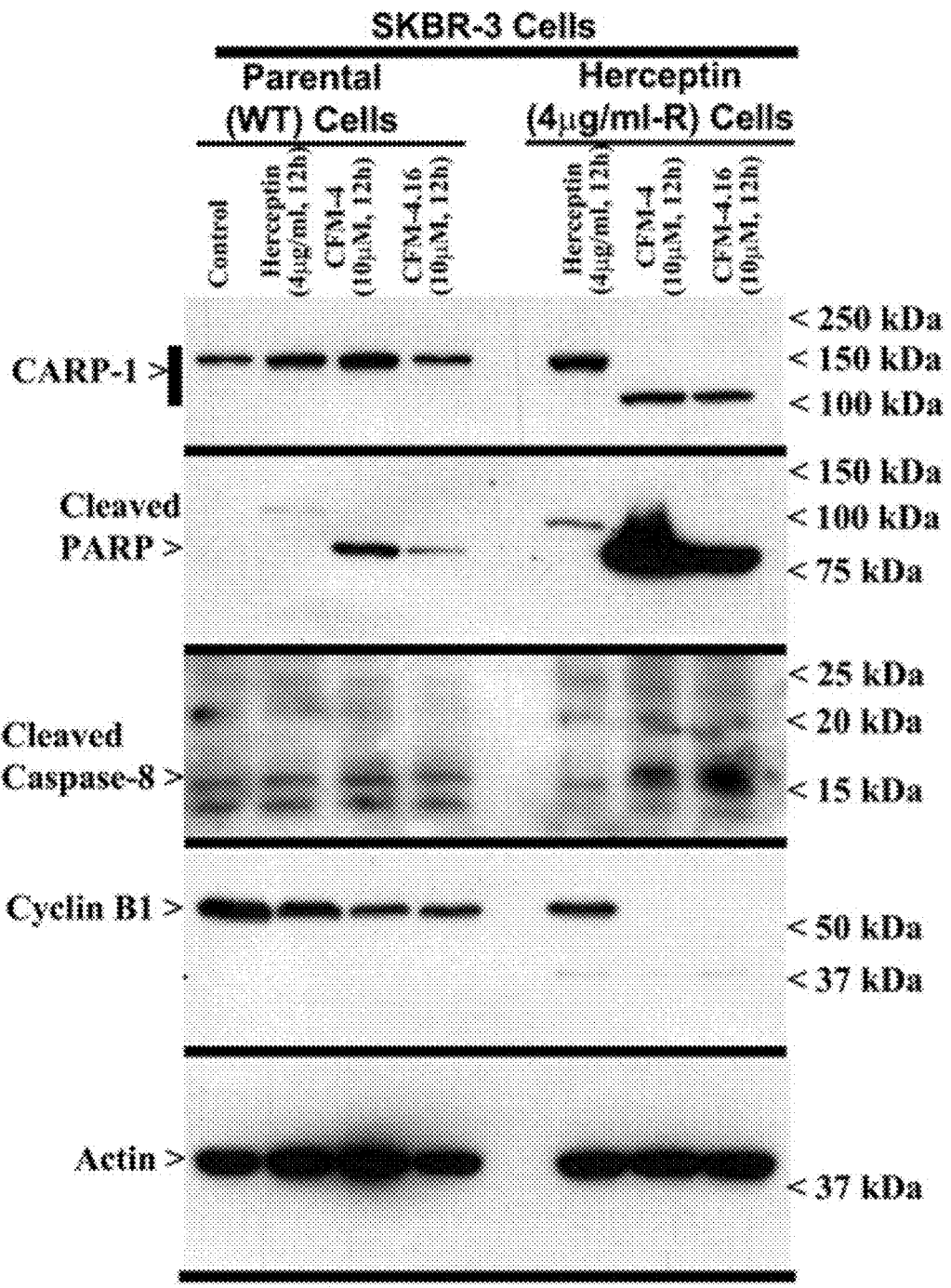
FIG. 6C shows that CFM-4.16 stimulates apoptosis in Herceptin-resistant breast cancer cells in part by upregulating pro-apoptotic CARP-1. Indicated breast cancer cells were either untreated (Control), treated with Cisplatin, Herceptin, CFM-4, or CFM-4.16 for noted dose and time. Cell lysates were analyzed by Western blotting for levels of CARP-1, cyclin B1, cleaved PARP and caspase-8.
Figure 6D:
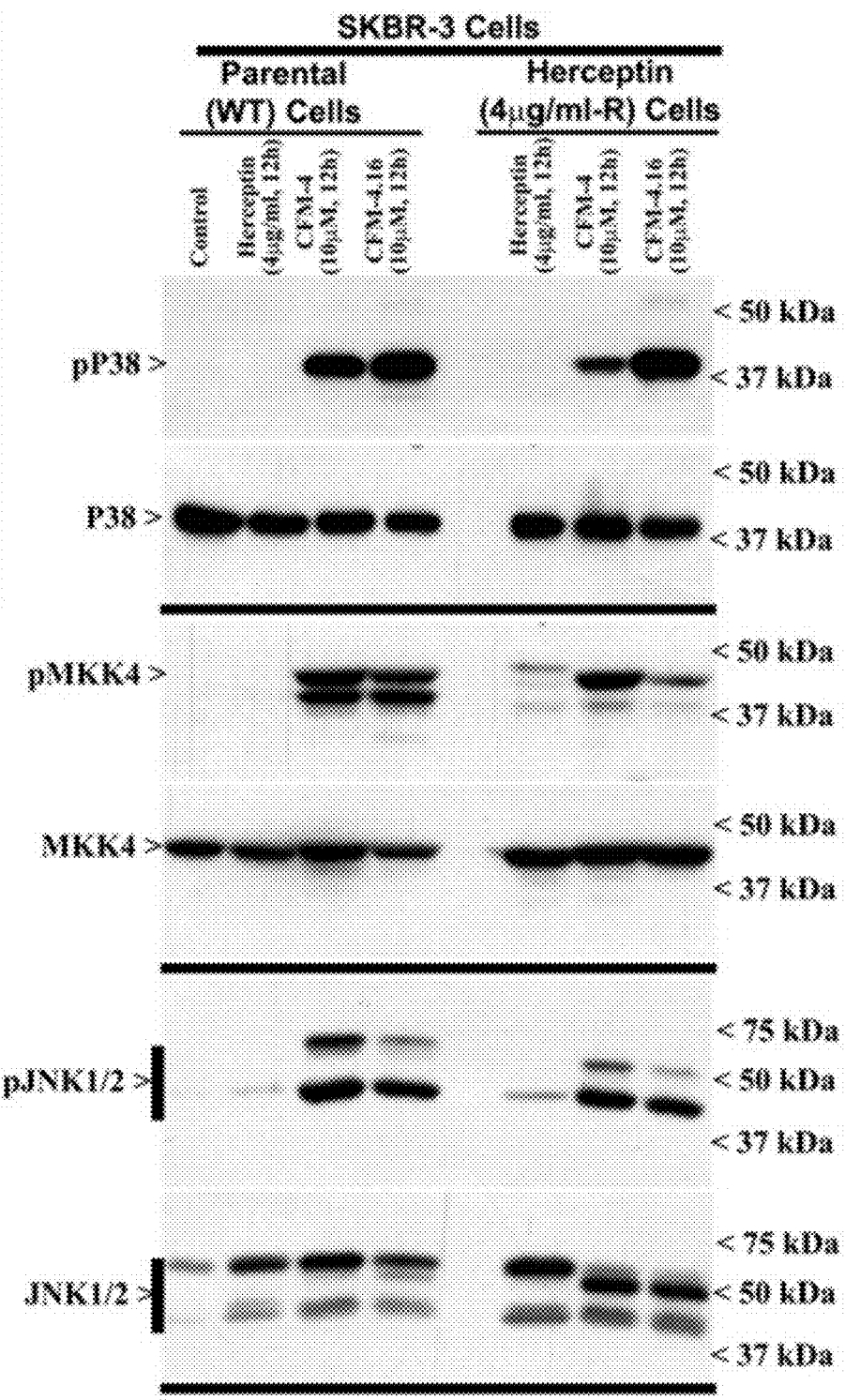
FIG. 6D shows that CFM-4.16 stimulates apoptosis in Herceptin-resistant breast cancer cells in part by upregulating pro-apoptotic CARP-1. Indicated breast cancer cells were either untreated (Control), treated with Cisplatin, Herceptin, CFM-4, or CFM-4.16 for noted dose and time. Cell lysates were analyzed by Western blotting for activation (phosphorylation) of pro-apoptotic p38, MKK4, and JNK1/2 SAPKs.

CARP-1 has previously been shown to function as a regulator of breast cancer cell growth by ADR [Rishi A K, Zhang L, Boyanapalli M, Wali A, Mohammad R M, Yu Y, Fontana J A, Hatfield J S, Dawson M I, Majumdar A P N, Reichert U. Identification and characterization of a Cell-Cycle and Apoptosis Regulatory Protein [CARP]-1 as a novel mediator of apoptosis signaling by Retinoid CD437. J Biol Chem. 2003; 278:33422-33435; Kim J H, Yang C K, Heo K, Roeder R G, An W, Stallcup M R. CCAR1, a key regulator of mediator complex recruitment to nuclear receptor transcription complexes. Molecular Cell. 2008; 31:510-519; Rishi A K, Zhang L, Yu Y, Jiang Y, Nautiyal J, Wali A, Fontana J A, Levi E, Majumdar A P N. Cell cycle and apoptosis regulatory protein [CARP]-1 is involved in apoptosis signaling by epidermal growth factor receptor. J Biol Chem. 2006; 281:13188-98]. Knock-down of CARP-1 resulted in elevated levels of topoisomerase IIα [Rishi A K, Zhang L, Boyanapalli M, Wali A, Mohammad R M, Yu Y, Fontana J A, Hatfield J S, Dawson M I, Majumdar A P N, Reichert U. Identification and characterization of a Cell-Cycle and Apoptosis Regulatory Protein [CARP]-1 as a novel mediator of apoptosis signaling by Retinoid CD437. J Biol Chem. 2003; 278:33422-33435], and abrogated HBC cell growth inhibition by ADR, Etoposide or CFM-4 [Rishi A K, Zhang L, Boyanapalli M, Wali A, Mohammad R M, Yu Y, Fontana J A, Hatfield J S, Dawson M I, Majumdar A P N, Reichert U. Identification and characterization of a Cell-Cycle and Apoptosis Regulatory Protein [CARP]-1 as a novel mediator of apoptosis signaling by Retinoid CD437. J Biol Chem. 2003; 278:33422-33435; Kim J H, Yang C K, Heo K, Roeder R G, An W, Stallcup M R. CCAR1, a key regulator of mediator complex recruitment to nuclear receptor transcription complexes. Molecular Cell. 2008; 31:510-519; Puliyappadamba et al.]. Moreover, CFM-4 and its analog CFM-4.6 inhibited growth of TNBC and NSCLC cells in part by inducing apoptosis and stimulating activation of pro-apoptotic, stress-activated protein kinases (SAPKs) p38α/β and JNK1/2, caspase-8, and cleavage of PARP [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627]. Consistent with these findings, western blot analyses in FIGS. 5A-5C and FIGS. 6A-6D show that CFM-4.16 activated pro-apoptotic SAPKs p38α/β and JNK1/2, caspase-8, while causing cleavage of PARP and decline in mitotic cyclin B1 levels in both the parental and drug-resistant TNBC cells. Since prior studies have demonstrated a requirement for CARP-1 expression in transduction of growth inhibitory signaling by ADR or CFM-4 [Rishi A K, Zhang L, Boyanapalli M, Wali A, Mohammad R M, Yu Y, Fontana J A, Hatfield J S, Dawson M I, Majumdar A P N, Reichert U. Identification and characterization of a Cell-Cycle and Apoptosis Regulatory Protein [CARP]-1 as a novel mediator of apoptosis signaling by Retinoid CD437. J Biol Chem. 2003; 278:33422-33435; Kim J H, Yang C K, Heo K, Roeder R G, An W, Stallcup M R. CCAR1, a key regulator of mediator complex recruitment to nuclear receptor transcription complexes. Molecular Cell. 2008; 31:510-519; Puliyappadamba et al.], it was next determined whether CARP-1 was also required for CFM-4.16-dependent growth inhibition of drug-resistant TNBC cells. For this purpose, siRNA-mediated knock-down of CARP-1 in ADR-resistant MDA-MB-468 subline 1 cells was conducted, essentially following methods described by the current inventors previously [Puliyappadamba et al.]. SiRNA-mediated depletion of CARP-1 levels in ADR-resistant MDA-MB-468 subline 1 cells (FIG. 5D) interfered with growth inhibition of these cells by CFM-4 or CFM-4.16 (FIG. 5E). These data suggest that CARP-1 is a necessary transducer of inhibitory signaling by CFM-4 and its analog CFM-4.16 in the parental as well as the drug-resistant TNBC cells. It is of note here that CFM-4.16 treatment induced a rather robust activation of both the pro-apoptotic SAPKs in comparison with CFM-4 in the parental as well as resistant TNBC cells (FIG. 5C). Whether and to the extent such robust activation of pro-apoptotic SAPKs by CFM-4.16 contributes to its superior TNBC growth inhibitory effects remain to be clarified.

Figure 7A:
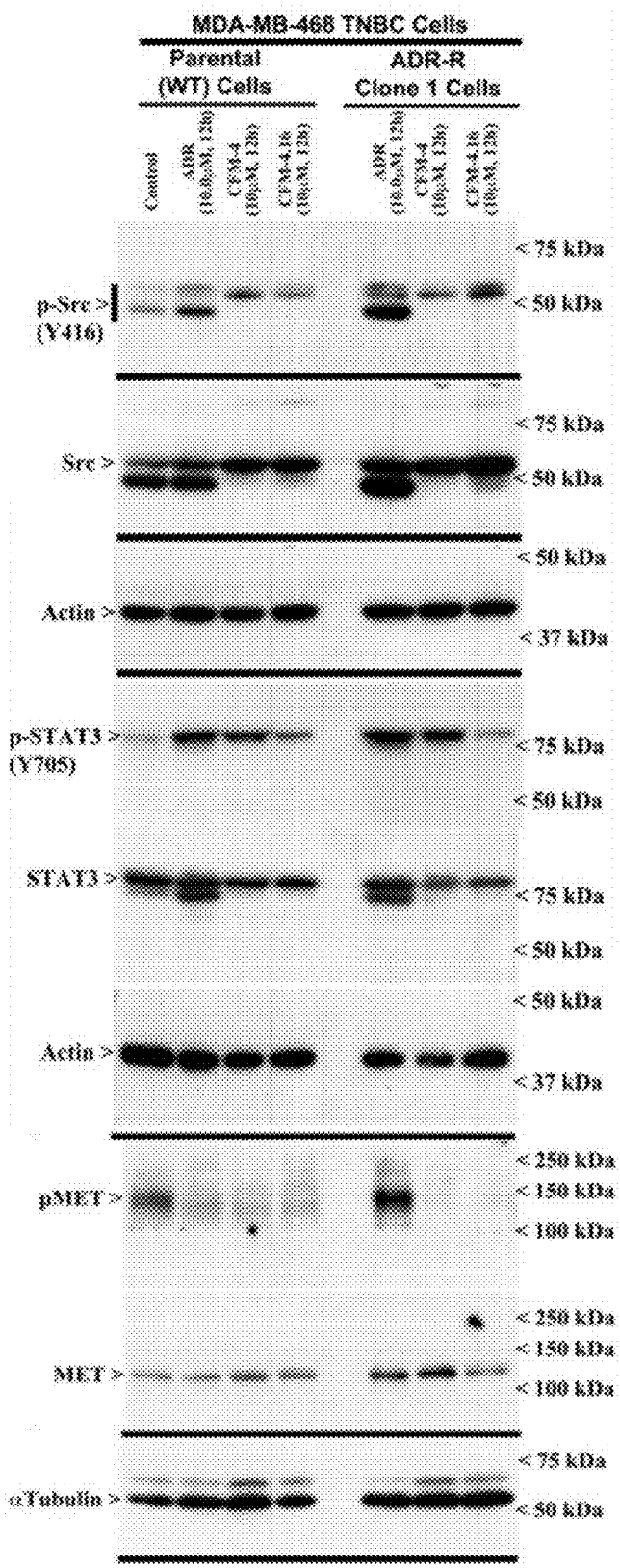
FIG. 7A shows that CFM-4.16 inhibits oncogenic tyrosine kinases in ADR-resistant TNBC cells. MDA-MB-468 TNBC cells were untreated (Control), treated with ADR, CFM-4, or CFM-4.16 for noted dose and time. Cell lysates were analyzed for expression and activation (phosphorylation) of Src, MET, and STAT3 kinases, and levels of actin and α-tubulin proteins by Western blotting. Identity of respective protein and molecular weight markers is denoted by arrowheads on the left and right side, respectively, of each WB.
Figure 7B:
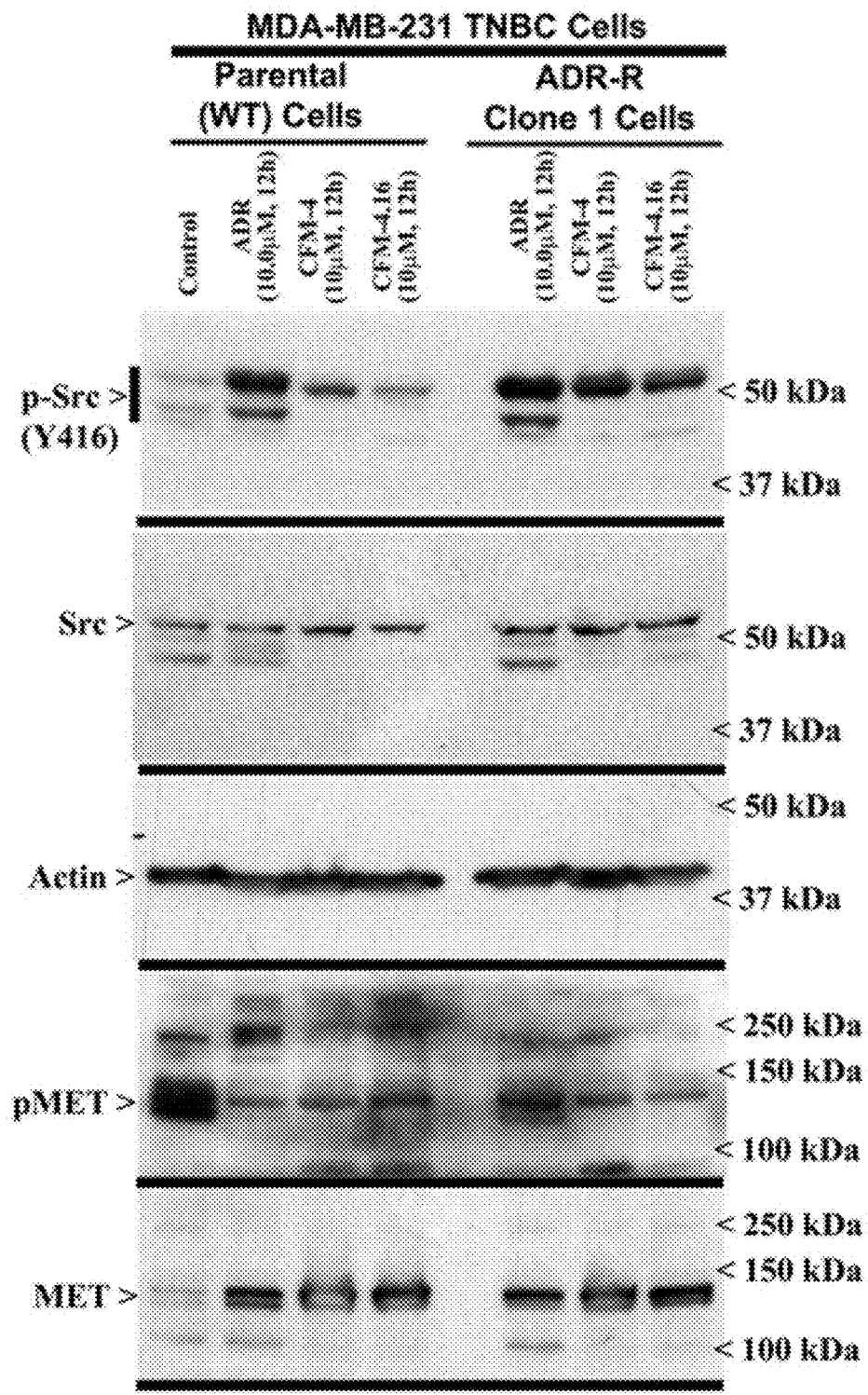
FIG. 7B shows that CFM-4.16 inhibits oncogenic tyrosine kinases in ADR-resistant TNBC cells. MDA-MB-231 TNBC cells were untreated (Control), treated with ADR, CFM-4, or CFM-4.16 for noted dose and time. Cell lysates were analyzed for expression and activation (phosphorylation) of Src, MET, and STAT3 kinases, and levels of actin and α-tubulin proteins by Western blotting. Identity of respective protein and molecular weight markers is denoted by arrowheads on the left and right side, respectively, of each WB.
Figure 7C:
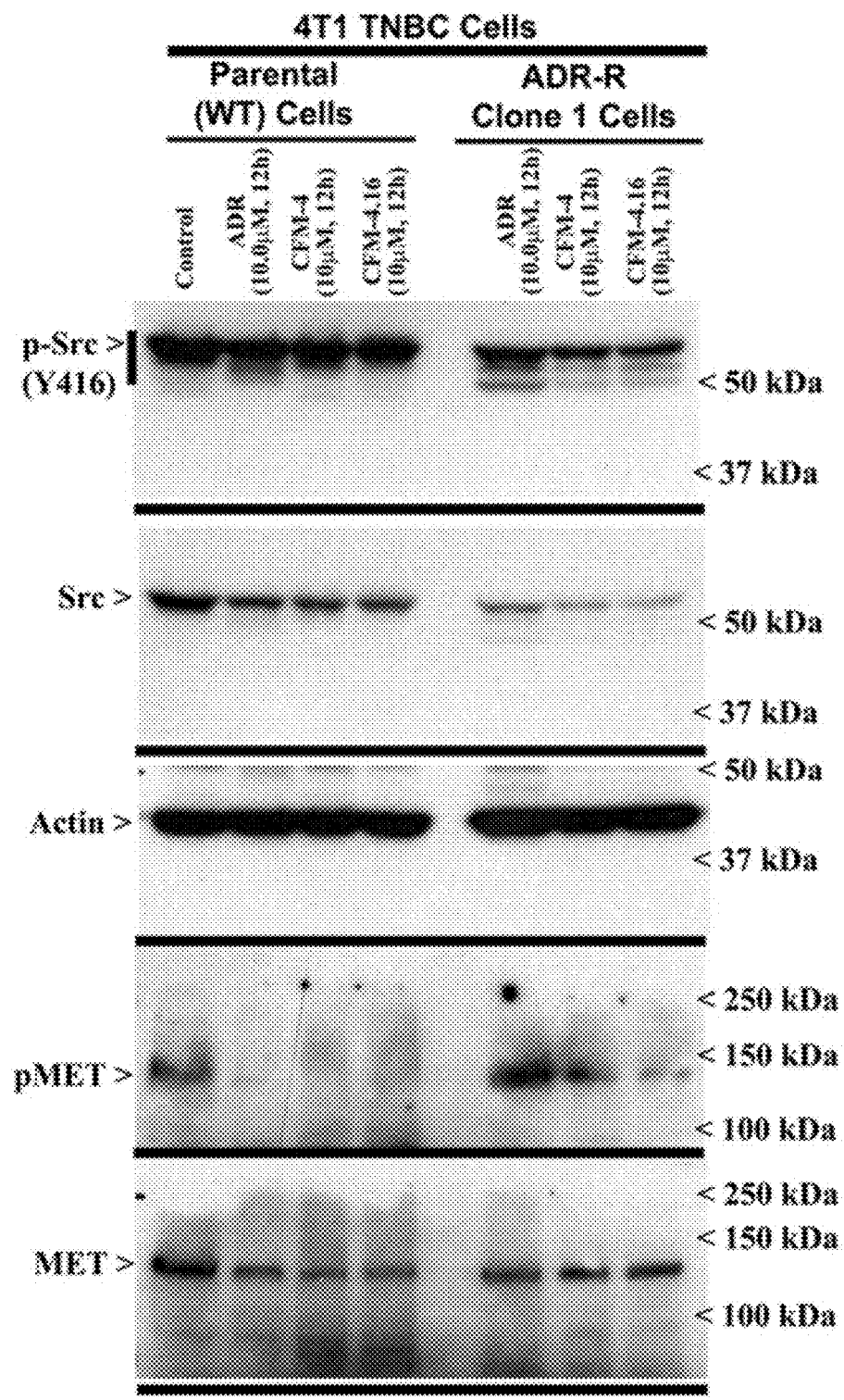
FIG. 7C shows that CFM-4.16 inhibits oncogenic tyrosine kinases in ADR-resistant TNBC cells. 4T1 TNBC cells were untreated (Control), treated with ADR, CFM-4, or CFM-4.16 for noted dose and time. Cell lysates were analyzed for expression and activation (phosphorylation) of Src, MET, and STAT3 kinases, and levels of actin and α-tubulin proteins by Western blotting. Identity of respective protein and molecular weight markers is denoted by arrowheads on the left and right side, respectively, of each WB.
Figure 8A:
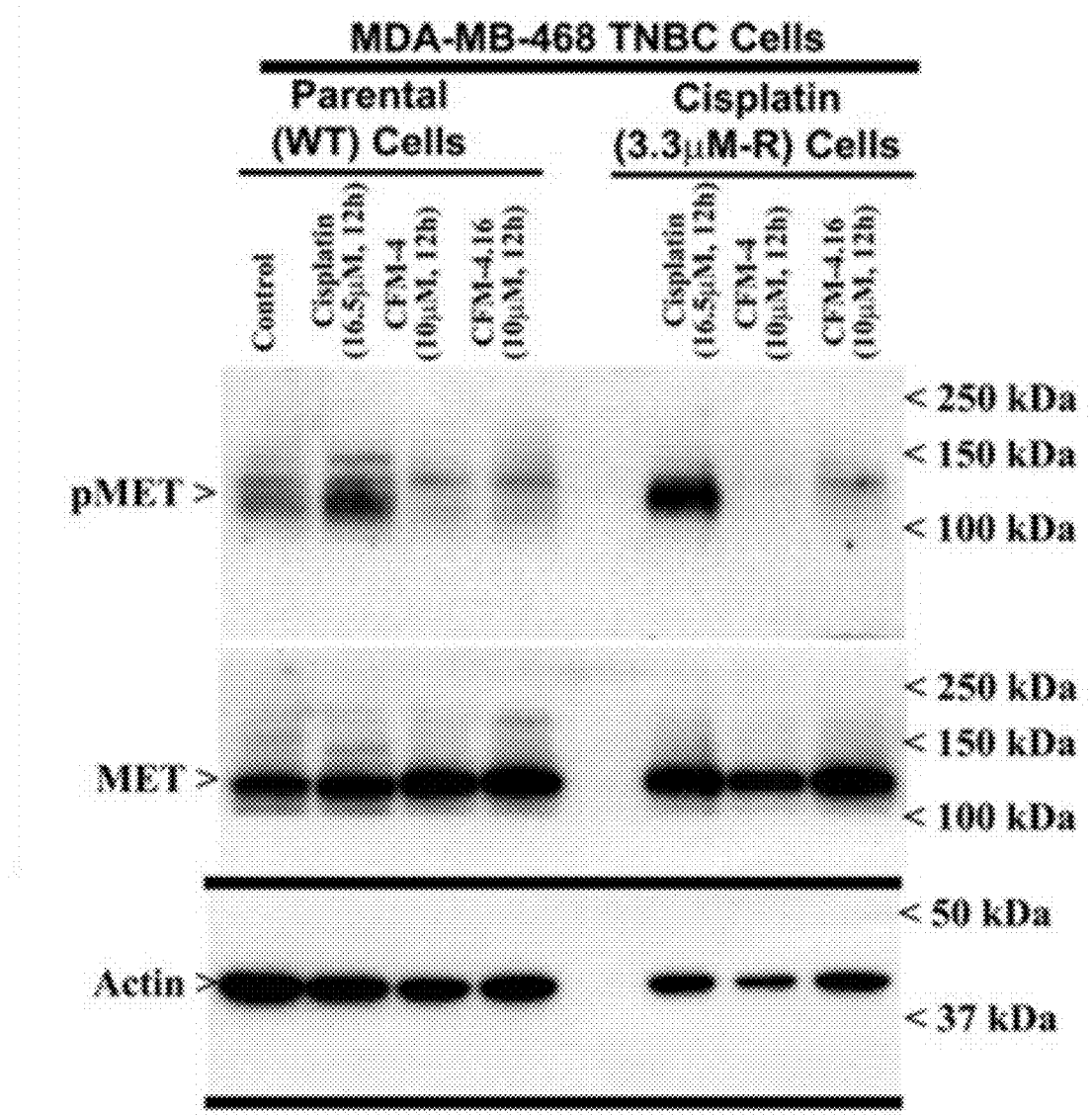
FIG. 8A shows that CFM-4.16 inhibits oncogenic tyrosine kinases in Cisplatin-resistant TNBC cells. MDA-MB-468 TNBC cells were untreated (Control), treated with Cisplatin, Herceptin, CFM-4, or CFM-4.16 for noted dose and time. Cell lysates were analyzed for expression and activation (phosphorylation) of Src, MET, and STAT3 kinases, and levels of actin proteins by Western blotting. Identity of respective protein and molecular weight markers is denoted by arrowheads on the left and right side, respectively, of each WB.
Figure 8B:
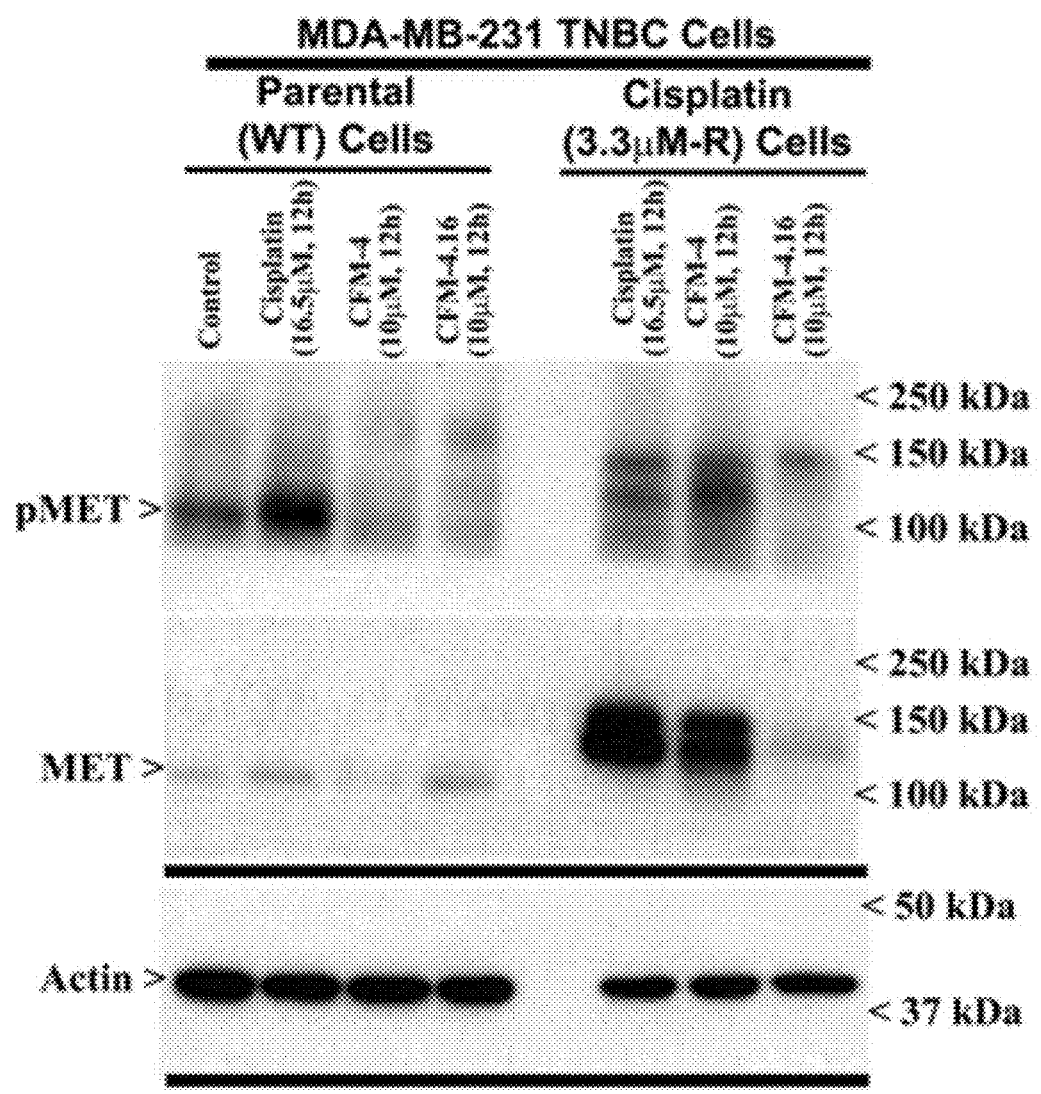
FIG. 8B shows that CFM-4.16 inhibits oncogenic tyrosine kinases in Cisplatin-resistant TNBC cells. MDA-MB-231 TNBC cells were untreated (Control), treated with Cisplatin, Herceptin, CFM-4, or CFM-4.16 for noted dose and time. Cell lysates were analyzed for expression and activation (phosphorylation) of Src, MET, and STAT3 kinases, and levels of actin proteins by Western blotting. Identity of respective protein and molecular weight markers is denoted by arrowheads on the left and right side, respectively, of each WB.
Figure 8C:
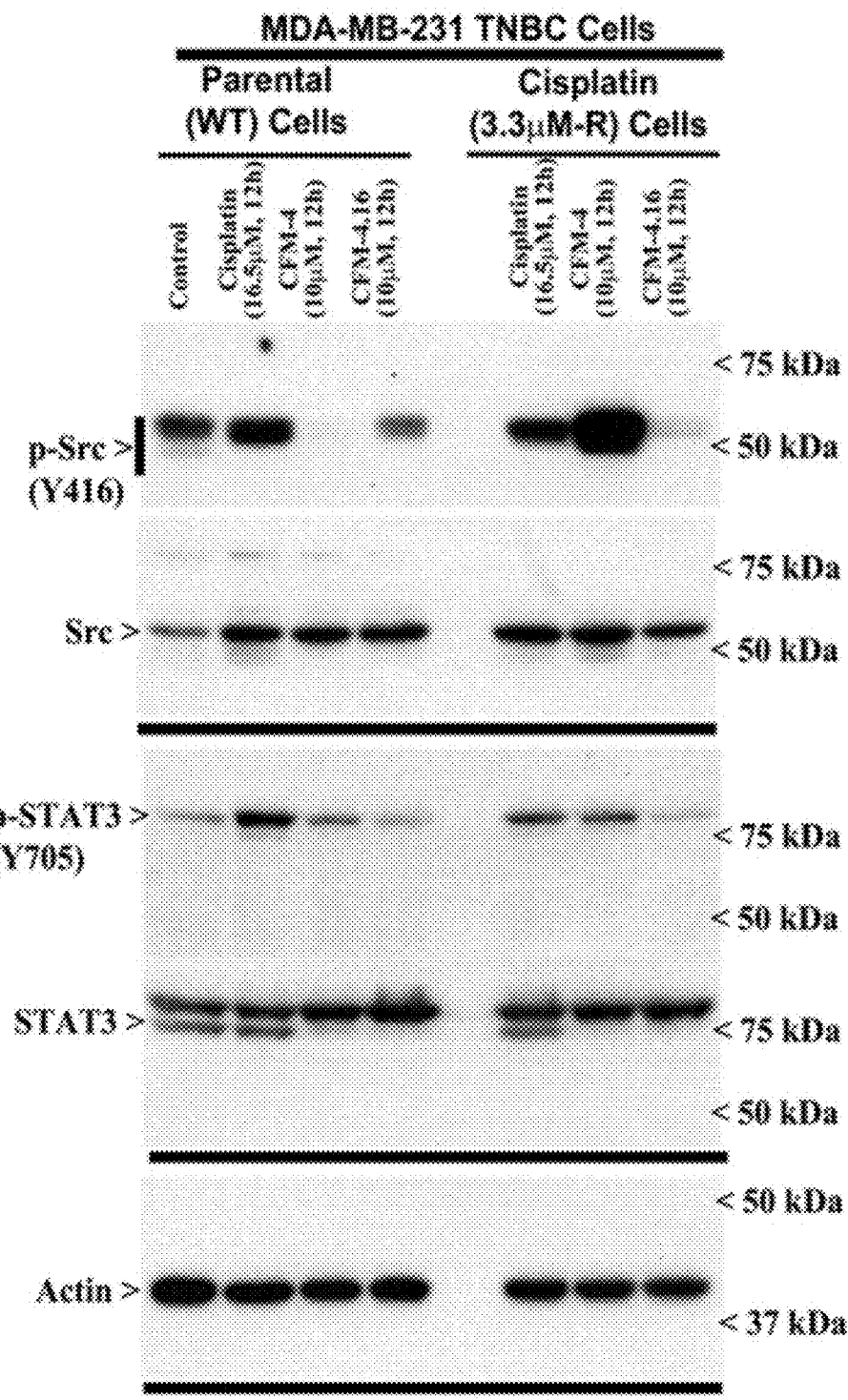
FIG. 8C shows that CFM-4.16 inhibits oncogenic tyrosine kinases in Cisplatin-resistant TNBC cells. Indicated breast cancer cells were untreated (Control), treated with Cisplatin, Herceptin, CFM-4, or CFM-4.16 for noted dose and time. Cell lysates were analyzed for expression and activation (phosphorylation) of Src, MET, and STAT3 kinases, and levels of actin proteins by Western blotting. Identity of respective protein and molecular weight markers is denoted by arrowheads on the left and right side, respectively, of each WB.
Figure 8D:
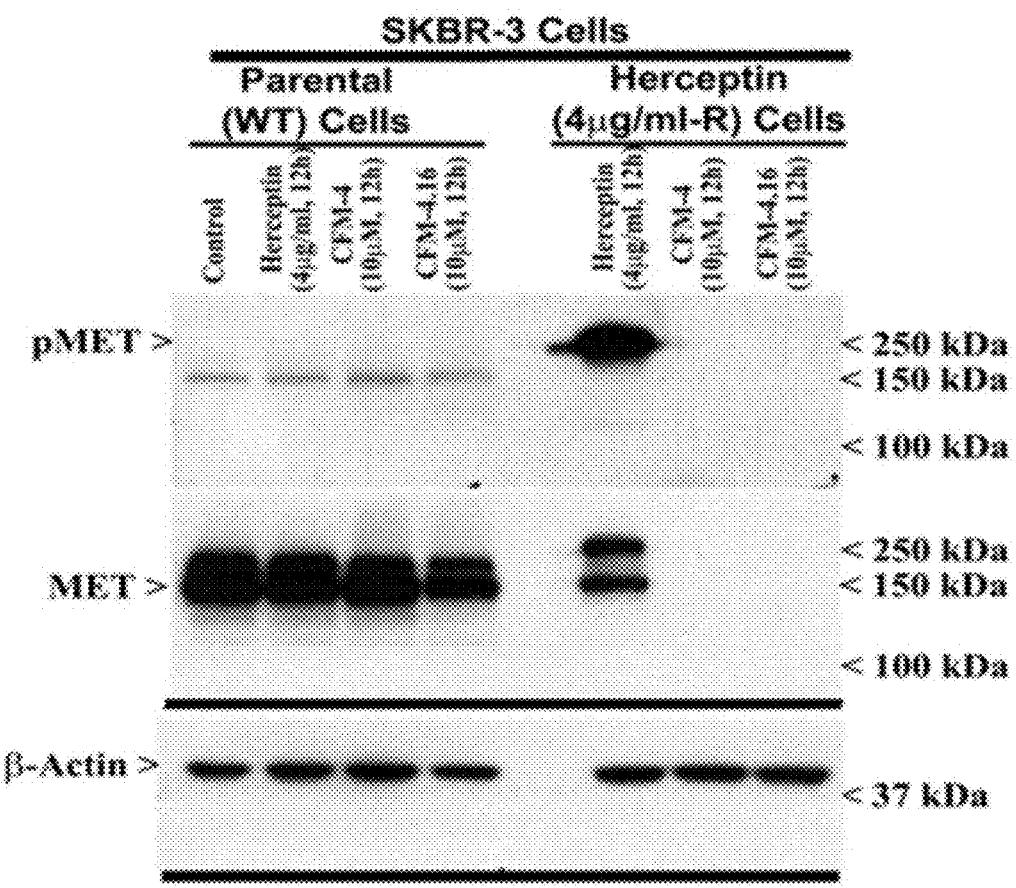
FIG. 8D shows that CFM-4.16 inhibits oncogenic tyrosine kinases in Herceptin-resistant breast cancer cells. Indicated breast cancer cells were either untreated (Control), treated with Cisplatin, Herceptin, CFM-4, or CFM-4.16 for noted dose and time. Cell lysates were analyzed for expression and activation (phosphorylation) of Src, MET, and STAT3 kinases, and levels of actin proteins by Western blotting. Identity of respective protein and molecular weight markers is denoted by arrowheads on the left and right side, respectively, of each WB.
Figure 9A:
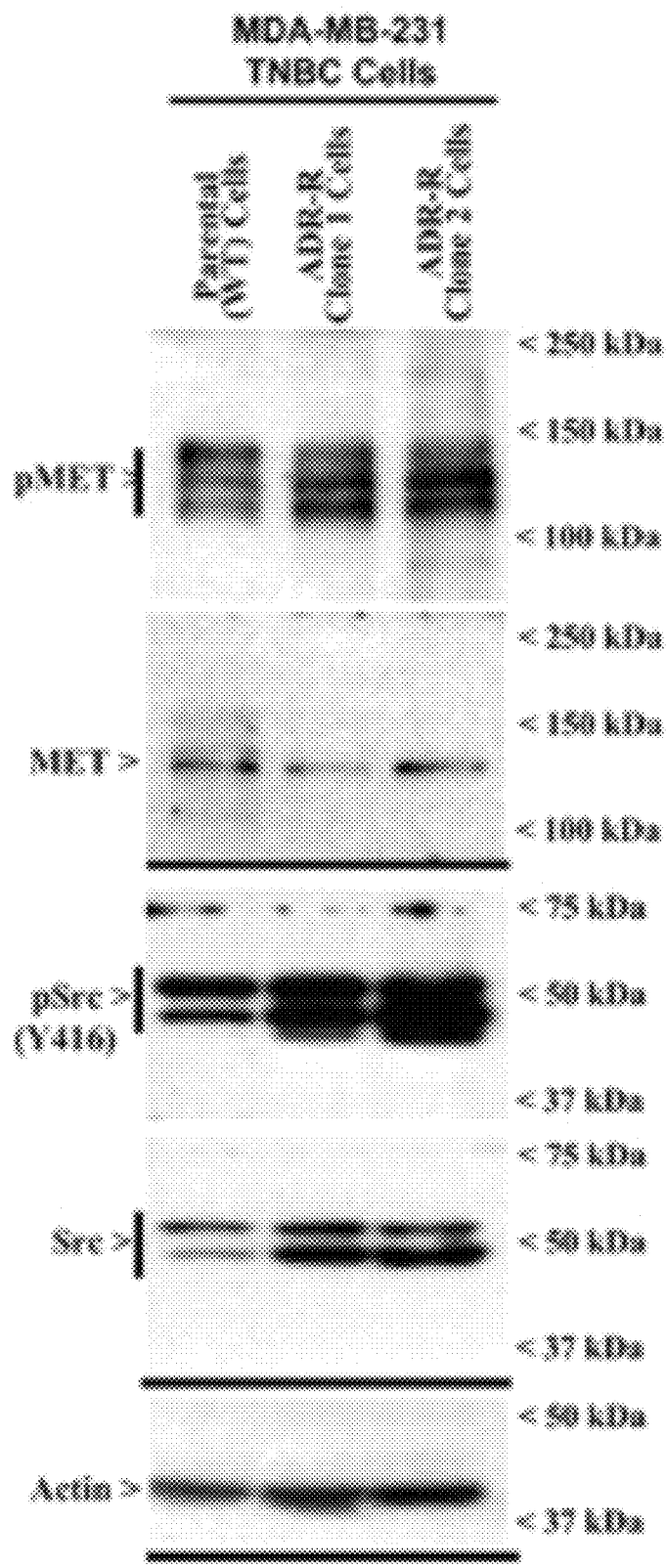
FIG. 9A depicts Activation and expression of Src and MET tyrosine kinases in parental and ADR-resistant TNBC cells. Cell lysates from MDA-MB-231 TNBC cells were analyzed for expression and activation (phosphorylation) of Src, MET, and levels of actin proteins by Western blotting. Identity of respective protein and molecular weight markers is denoted by arrowheads on the left and right side, respectively, of each WB. Note that in the case of MDA-MB-468 cells, the lysates were analyzed on two separate gels. Following transfer of proteins, one membrane was incubated with antibodies for p-Src, p-MET, and Actin proteins while the second membrane was incubated with antibodies for total Src, MET, and actin proteins.
Figure 9B:
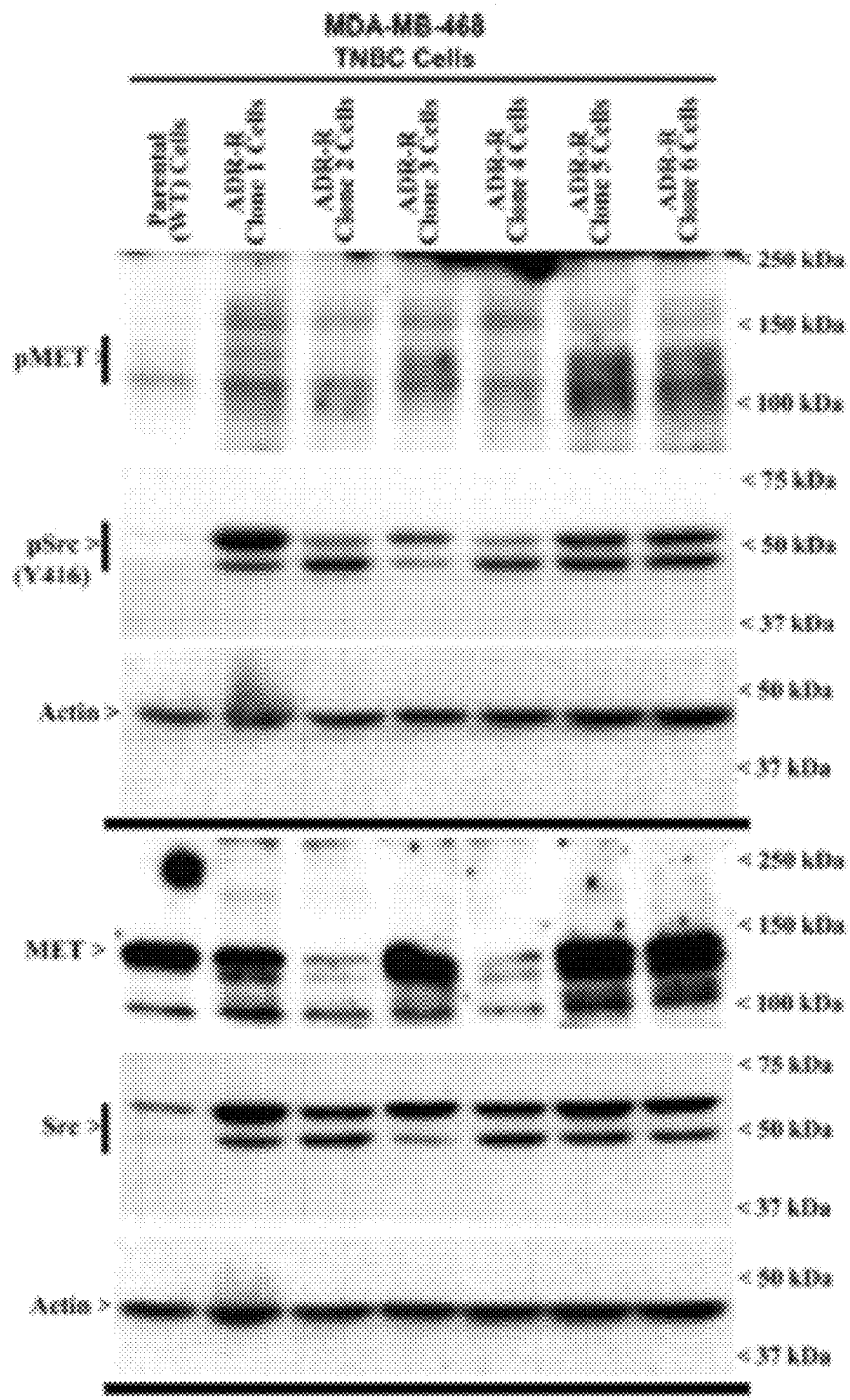
FIG. 9B depicts Activation and expression of Src and MET tyrosine kinases in parental and ADR-resistant TNBC cells. Cell lysates from MDA-MB-468 TNBC cells were analyzed for expression and activation (phosphorylation) of Src, MET, and levels of actin proteins by Western blotting. Identity of respective protein and molecular weight markers is denoted by arrowheads on the left and right side, respectively, of each WB. Note that in the case of MDA-MB-468 cells, the lysates were analyzed on two separate gels. Following transfer of proteins, one membrane was incubated with antibodies for p-Src, p-MET, and Actin proteins while the second membrane was incubated with antibodies for total Src, MET, and actin proteins.

C. CFMs Inhibit Activation and/or Expression of Cell Growth and Survival Promoting Oncogenic Tyrosine Kinases Aberrant expression and/or activation of oncogenic signaling by kinases such as the Src and Abl tyrosine kinases, and receptor tyrosine kinases (RTKs) MET, Vascular endothelial growth factor receptor (VEGFR), Fibroblast growth factor receptor (FGFR), Insulin-like growth factor receptor 1 (IGF-1R), as well as members of the epidermal growth factor receptor (EGFR) family, have been well documented to play pivotal roles in cancer development, progression, metastasis, and often function as significant drivers of development of therapy resistance in many cancers including TNBCs [Rosenzweig S A. Acquired resistance to drugs targeting receptor tyrosine kinases. Biochem Pharmacol. 2011; 83:1041-8]. Western-blot analyses were conducted to further elucidate molecular mechanisms of TNBC growth inhibition by CFM-4 and its analog CFM-4.16, and to determine whether CFM class of compounds targeted activation and/or expression of oncogenic tyrosine kinases. The parental and drug-resistant TNBC cells were treated with ADR, CFM-4 or CFM-4.16, and in the first instance, the cell lysates were analyzed for activation and/or expression of Src and MET tyrosine kinases. As shown in FIGS. 7A-7C, 8A-8D, and 9A-9B, expression and/or activity of MET RTK was moderately elevated in ADR as well as Cisplatin-resistant TNBC cells. Activity and/or expression of Src were also moderately elevated in ADR-resistant human TNBC cells but not in ADR-resistant murine or cisplatin-resistant human TNBC cells. These data are consistent with well-documented roles of these oncogenic kinases as drivers of drug resistance in many cancers including TNBCs. CFM-4 and CFM-4.16 treatments however caused reduced activation and/or expression of both MET and Src tyrosine kinases in parental as well as drug-resistant human and murine TNBC cells (FIGS. 7A-7C and 8A-8D), suggesting that CFM class of molecules function in part by targeting oncogenic kinases and their signaling to promote apoptosis and suppress cell growth. Interestingly, activation of STAT3, a well-known down-stream transducer of signaling by activated EGFR and Src tyrosine kinases in TNBC cells [Garcia R, Bowman T L, Niu G, Yu H, Minton S, Muro-Cacho C A, Cox C E, Falcone R, Fairclough R, Parsons S, Laudano A, Gazit A, Levitzki A, et al. Constitutive activation of Stat3 by the Src and JAK tyrosine kinases participates in growth regulation of human breast carcinoma cells. Oncogene. 2001; 20:2499-513], was robustly attenuated in CFM-4.16 but not CFM-4-treated ADR as well as Cisplatin-resistant human TNBC cells (FIGS. 7A and 8C). These findings together with the data demonstrating a robust activation of pro-apoptotic SAPKs by CFM-4.16 when compared with CFM-4 would suggest for potential of this compound as a superior inhibitor of drug-resistant TNBCs.

Figure 10:
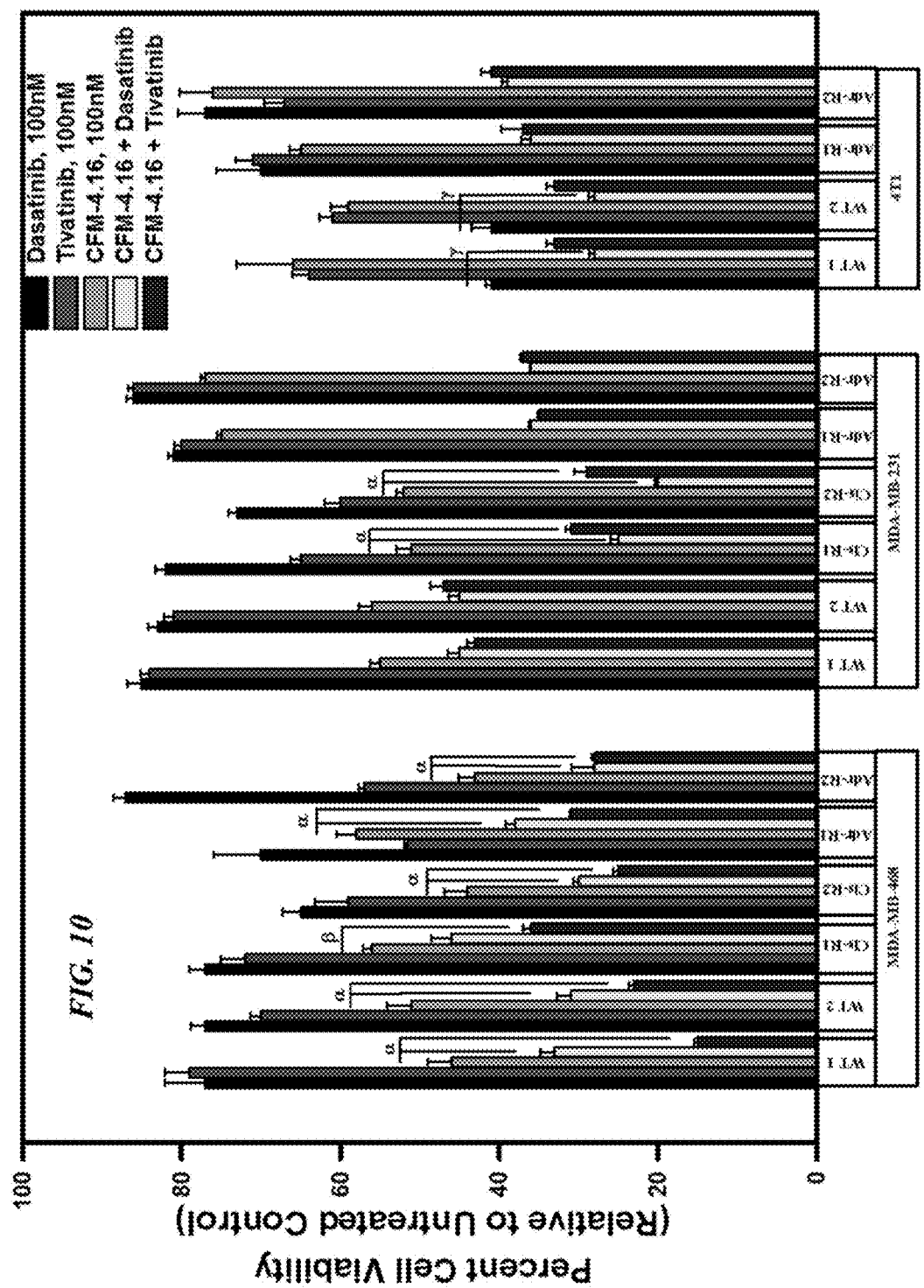
FIG. 10 shows that CFM-4.16 enhances efficacy of compounds that target MET or Src kinases in drug-resistant TNBCs. Indicated parental and their respective drug-resistant sublines were untreated, treated with noted dose of MET inhibitor Tevatinib, Src inhibitor Dasatinib, CFM-4.16, a combination of CFM-4.16 and Dasatinib, or a combination of CFM-4.16 and Tevatinib. Note that the cells were exposed to CFM-4.16 for 24 h while cells were treated with Dasatinib or Tevatinib (as single agent or in combination with CFM-4.16) for 12 h. Cell viability was determined by MTT assay as in FIG. 1. The histogram columns represent means of three independent experiments; bars, S. E. α and β, p=<0.03 relative to respective cells treated with CFM-4.16 only. γ, p=<0.01 relative to respective cells treated with Dasatinib only.

Since MET and Src tyrosine kinases are moderately activated and/or overexpressed in drug resistant TNBC cells and CFM-4.16 treatments attenuated activation of MET in parental and drug-resistant TNBC cells, while impacting Src activities only in Cisplatin-resistant TNBC cells (FIGS. 7A-7C and 8A-8D), it was next determined whether pretreatment with CFM-4.16 could sensitize/enhance growth suppression of TNBC cells by pharmacologic inhibitors of MET and/or Src kinases. For this purpose, Dasatinib was utilized as a multi-targeted orally administered inhibitor of RTKs and Src family of tyrosine kinases [Gnoni A, Marech I, Silvestris N, Vacca A, Lorusso V. Dasatinib: an antitumour agent via Src inhibition. Curr Drug Targets. 2011; 12:563-78] that is FDA approved treatment for chronic myelogenous leukemia (CML). In addition, Tivatinib, an investigational orally administered, highly selective inhibitor of the MET RTK was utilized [Scagliotti G, von Pawel J, Novello S, Ramlau R, Favaretto A, Barlesi F, Akerley W, Orlov S, Santoro A, Spigel D, Hirsh V, Shepherd F A, Sequist L V, et al. Phase III multinational, randomized, double-blind, placebo-controlled study of Tivantinib (ARQ 197) plus erlotinib versus erlotinib alone in previously treated patients with locally advanced or metastatic non-squamous non-small-cell lung cancer. J Clin Oncol. 2015; 33:2667-2674]. The parental and the drug-resistant TNBC cells were either treated with CFM-4.16, Dasatinib, or Tivatinib as single agents or the cells were first treated with CFM-4.16 for 12 h, followed by addition of Dasatinib or Tivatinib for another 12 h. As shown in FIG. 10, treatments with Dasatinib or Tivatinib alone generally elicited a moderate, 20-40% loss of viability of parental as well as drug-resistant human TNBC cells. Although parental and drug-resistant human TNBC cells, with the exception of ADR-resistant MDA-MB-231 cells, elicited a higher 45-55% loss of viability when exposed to CFM-4.16 alone, CFM-4.16 in combination with Tivatinib provoked a much greater loss of viabilities of these cells when compared with either agent alone. Dasatinib in combination with CFM-4.16 however was more effective in inhibiting viabilities of drug-resistant MDA-MB-231 cells when compared with loss of viabilities elicited following treatments with either agent alone. Surprisingly, while Tivatinib or CFM-4.16 caused a reduction of ~30-40% viability of murine wild-type 4T1 TNBC cells, and Dasatinib caused ~60% loss of viability of these cells, either of these compounds caused a moderate, 20-30% loss of viability of the ADR-resistant 4T1 cells. A combination of Tivatinib and CFM-4.16 caused much greater loss of viability of wild-type 4T1 cells, while a combination of CFM-4.16 with Dasatinib or Tivatinib elicited a much greater loss of viability of ADR-resistant 4T1 cells. Together these data support the hypothesis that low-dose combination of CFM-4.16 with MET targeting could be an effective approach for TNBCs including their drug-resistant counterparts.

Figure 11A:
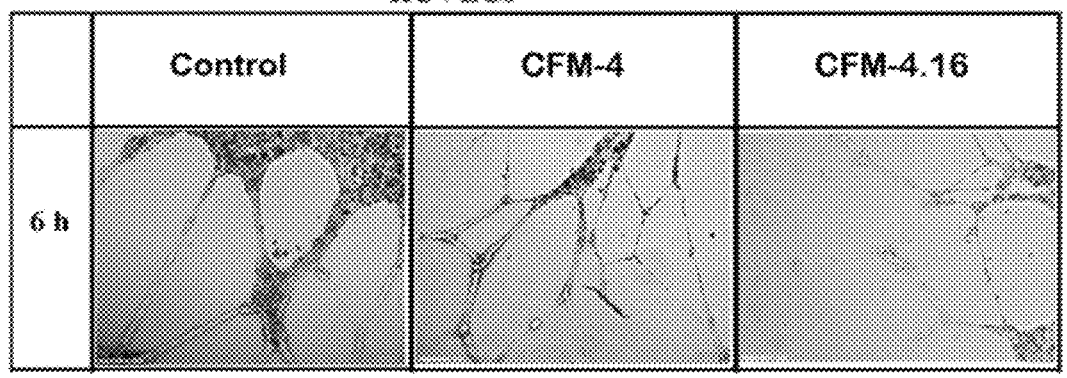
FIG. 11A shows HUVECs seeded onto a surface containing polymerized extracellular matrix (ECM), and allowed to develop network structures in buffer (Control) or CFM-treated cells. The growth of tubules was monitored over a period of 12 hours. The cells growth in the scratch assay was recorded by photography. Representative photomicrographs of control and treated cells are presented.
Figure 12C:
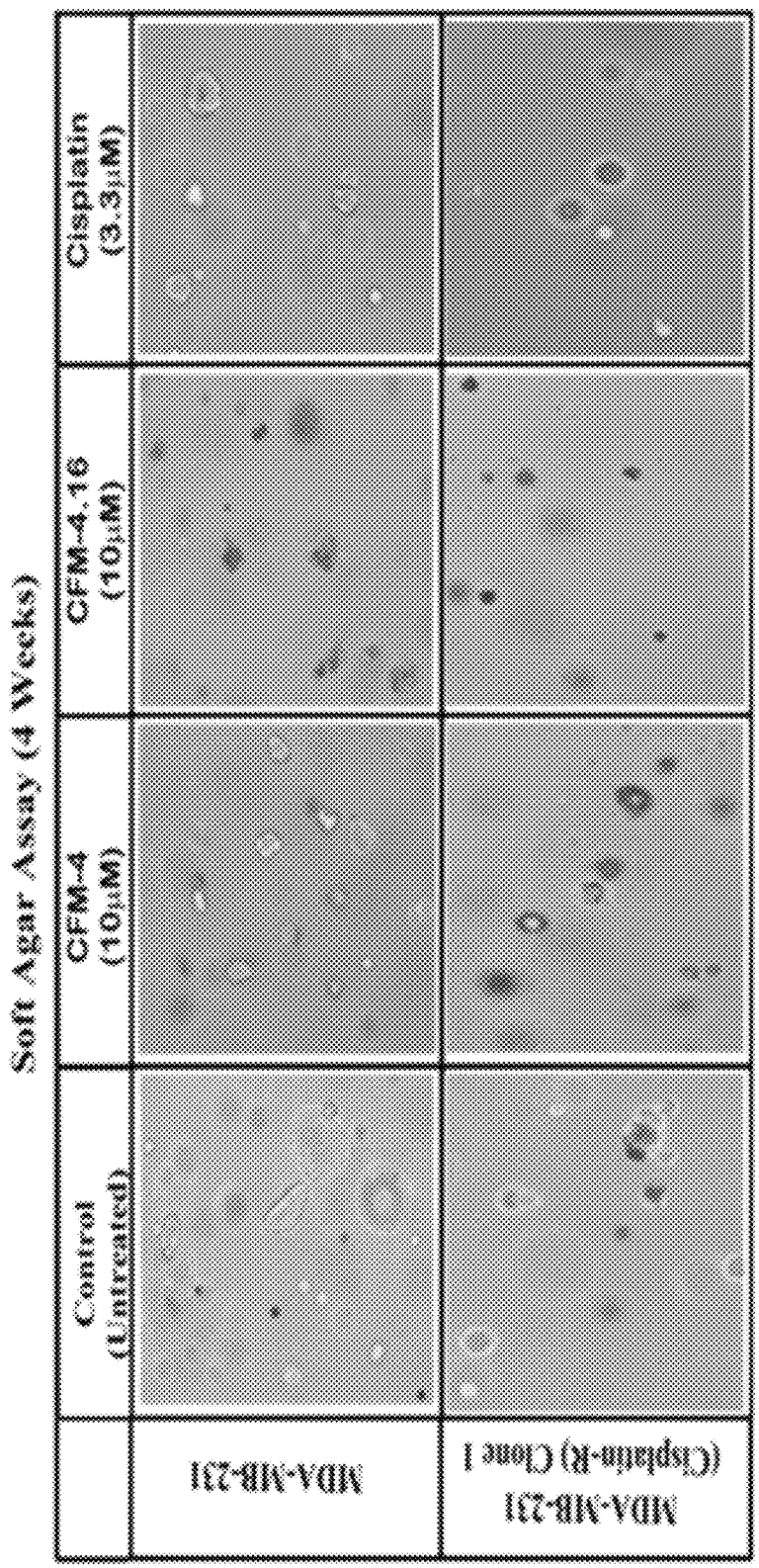
FIG. 12C shows that indicated TNBC cells were seeded in soft-agar and either untreated (Control), treated with 10 µM of each of CFMs, or 3.3 µM of Cisplatin for noted time. The number of colonies of cells was recorded by photography. Representative photomicrographs of untreated and treated TNBC cells are shown.
Figure 12D:
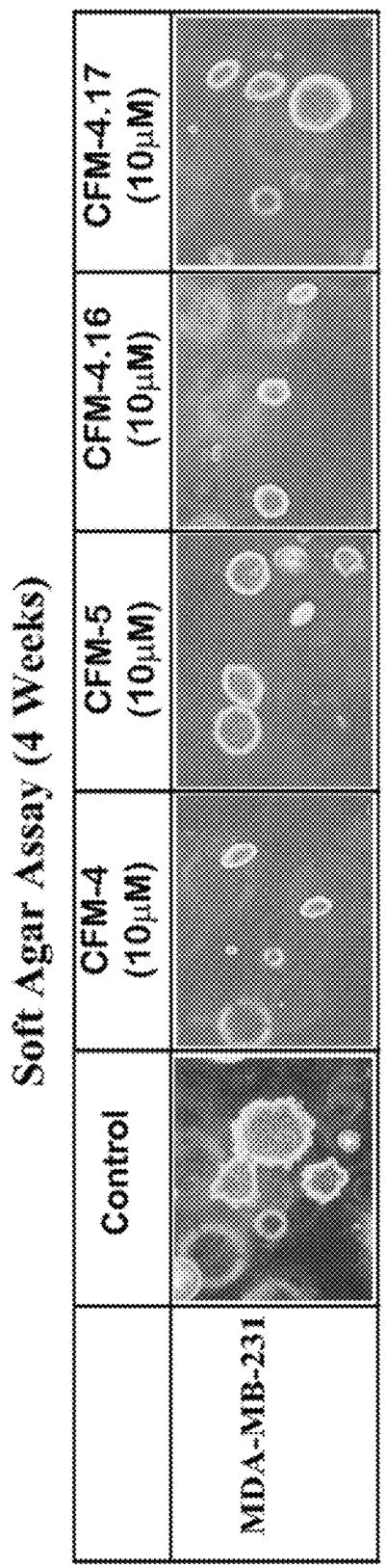
FIG. 12D shows that indicated TNBC cells were seeded in soft-agar and either untreated (Control), treated with 10 µM of each of CFMs, or 3.3 µM of Cisplatin for noted time. The number of colonies of cells was recorded by photography. Representative photomicrographs of untreated and treated TNBC cells are shown. Overall.
Figure 13B:
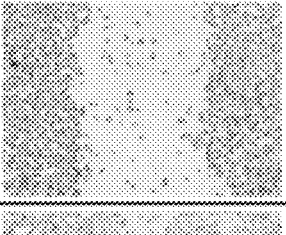
FIG. 13B shows that SKBR-3 (Herceptin-R Clone 4) breast cancer cells were untreated (Control), treated with 3 µM of CFM-4, 1.0 µM of CFM-4.16, or 2 µg/ml Herceptin for noted times, and were subjected to scratch assays. The cells growth in the scratch assay was recorded by photography. Representative photomicrographs of untreated and treated breast cancer cells are shown.
Figure 13C:
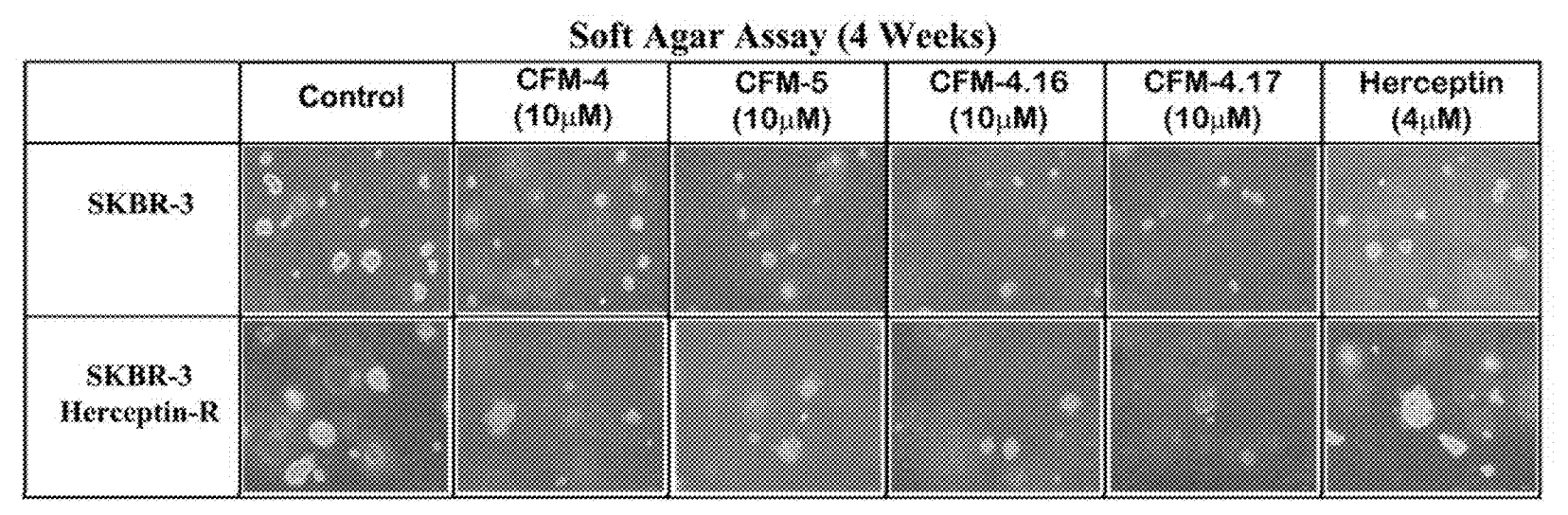

D. CFMs Suppress Migration and Three-Dimensional Growth of the Parental and Drug-Resistant TNBCs It was next investigated whether CFM-4.16 inhibited TNBC cell migration and growth as colonies in soft agar and 3-dimensional cultures in vitro. In addition, an in vitro tubule formation assay was conducted to determine anti-angiogenic properties of CFM-4.16. As shown in FIG. 11A, although CFM-4 or CFM-4.16 caused disruption of tubule formation by HUVECs when compared with untreated control, a rather robust disruption in tubule integrity was noted for CFM-4.16-treated HUVECs. Moreover, treatments with CFM-4 or CFM-4.16 prevented the parental as well as drug (ADR- or cisplatin-) resistant TNBC sublines and the parental and Herceptin-resistant, Her-2-positive SKBR-3 cells from growing in the areas of wound caused by a scratch (FIGS. 11B, 11C, 12A, 12B, 13A, and 13B). CFM-4 or CFM-4.16 also caused significant reduction in size and number of colonies formed by the parental as well as drug (ADR- or cisplatin-) resistant TNBC or Herceptin-resistant, Her-2-positive SKBR-3 cells in soft agar (FIGS. 11D, 12C, 12D, and 13C).

Figure 14A:
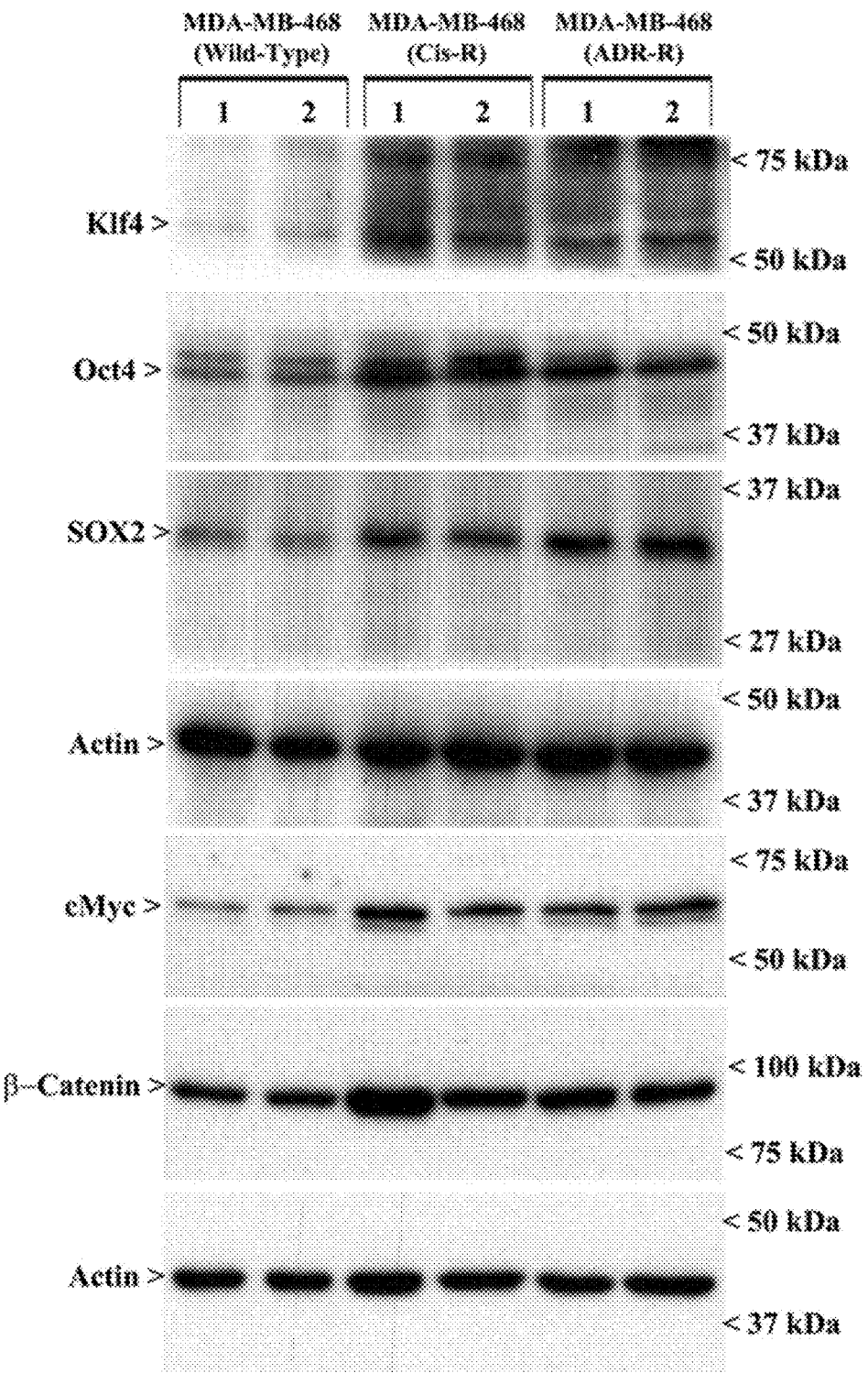
FIG. 14A shows that parental or drug-resistant TNBC cells were untreated, treated with noted time and dose of indicated agent, and cell lysates were analyzed by Western blotting for levels of Klf4, Oct4, SOX2, CD133, cMyc, β-catenin and actin proteins. Identity of respective protein and molecular weight markers is denoted by arrowheads on the left and right side, respectively, of each WB.
Figure 14B:
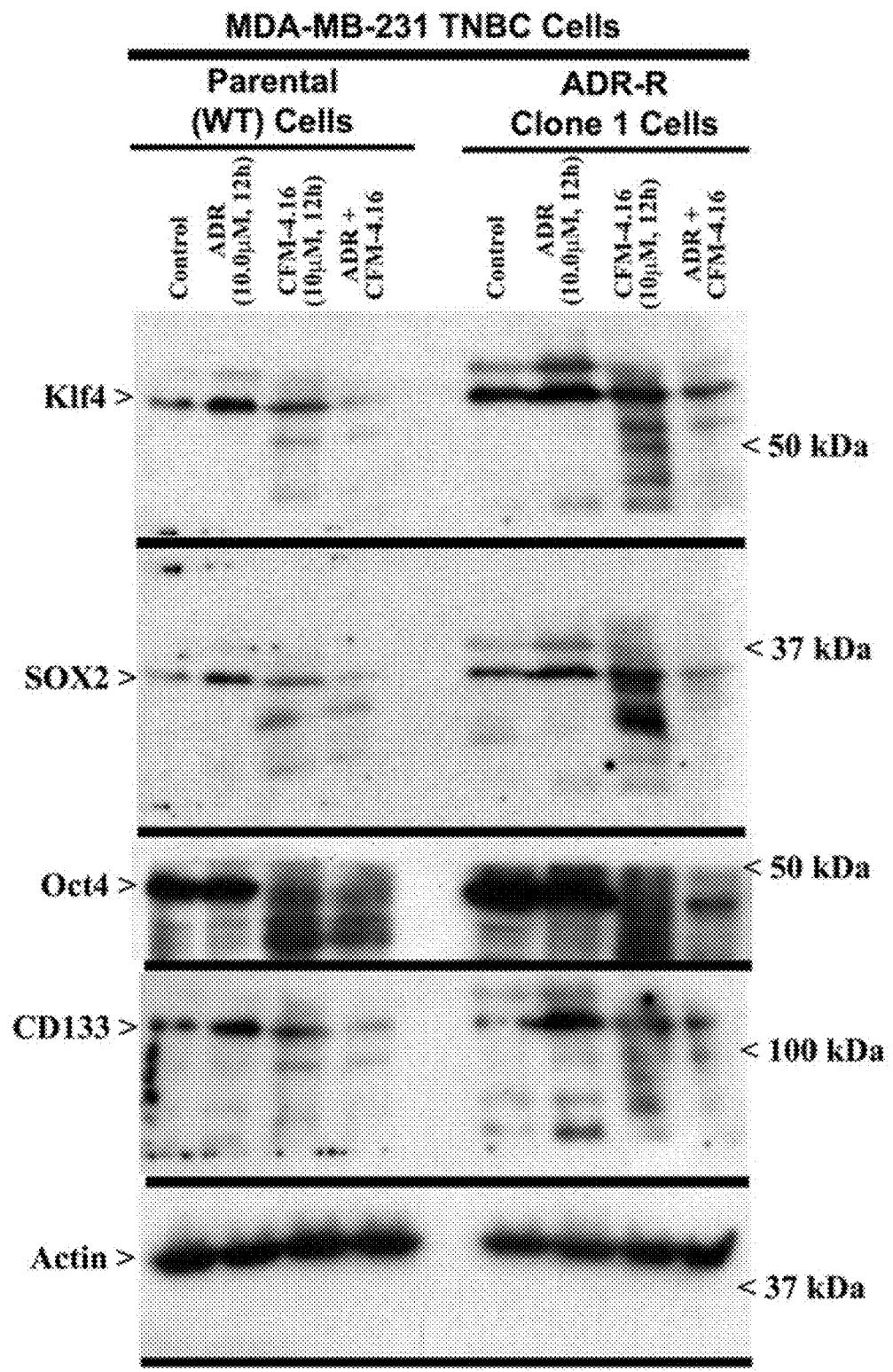
FIG. 14B shows that parental or drug-resistant TNBC cells were untreated, treated with noted time and dose of indicated agent, and cell lysates were analyzed by Western blotting for levels of Klf4, Oct4, SOX2, CD133, cMyc, β-catenin and actin proteins. Identity of respective protein and molecular weight markers is denoted by arrowheads on the left and right side, respectively, of each WB. Overall.

A wealth of recent studies has indicated that a unique, small subpopulation of tumor cells have stem cell properties, which are often referred to as cancer stem-like cells (CSCs), that are capable of propagating the tumor as well as contribute towards development of resistance against conventional therapeutic drugs [Wicha M S, Liu S, Dontu G. Cancer stem cells: an old idea—a paradigm shift. Cancer Res. 2006; 66:1883-90; Visvader J E, Lindeman G J. Cancer stem cells in solid tumours: accumulating evidence and unresolved questions. Nat Rev Cancer. 2008; 8:755-68]. The CSCs are often characterized by aberrant presence and/or expression of a number of distinct membrane and intracellular markers in various tumors [Hadjimichael C, Chanoumidou K, Papadopoulou N, Arampatzi P, Papamatheakis J, Kretsovali A. Common stemness regulators of embryonic and cancer stem cells. World Journal of Stem Cells. 2015; 7:1150-1184]. Since CSC-associated markers for breast cancers include CD44, ALDH, EpCAM, CD133, ABCG2, Oct4, Sox2, Nanog, and Klf4, it was first determined whether expression of any of these CSC-associated markers was altered in the drug-resistant TNBC cells, and to the extent their expression was impacted by CFM-4.16. Western-blot analysis revealed that expression of Klf4, Oct4, Sox2, c-Myc, and β-catenin was upregulated in ADR- or cisplatin-resistant MDA-MB-468 TNBC cells when compared with their parental counterparts (FIG. 14A). Similarly, although expression of Klf4, Oct4, and Sox2 was also elevated in ADR-resistant MDA-MB-231 TNBC cells, treatment with CFM-4.16 caused a robust decline in levels of Oct4 in both the parental and ADR-resistant MDA-MB-231 TNBC cells (FIG. 14B). A combination of ADR and CFM-4.16 however was highly effective in causing diminished levels of Klf4, Sox2, Oct4, and CD133 in both the parental and ADR-resistant MDA-MB-231 TNBC cells (FIG. 14B). The data in FIGS. 14A-14B collectively suggest that drug-resistant TNBC cells likely have a subpopulation of stem-like cells with elevated expression of CSC-associated markers that contribute to their growth and survival, and superior TNBC growth inhibition by ADR plus CFM-4.16 noted in FIG. 3C could be due, in part, to their ability to target expression of different CSC-associated markers in the parental as well as drug-resistant TNBC cells.

Figure 15A:
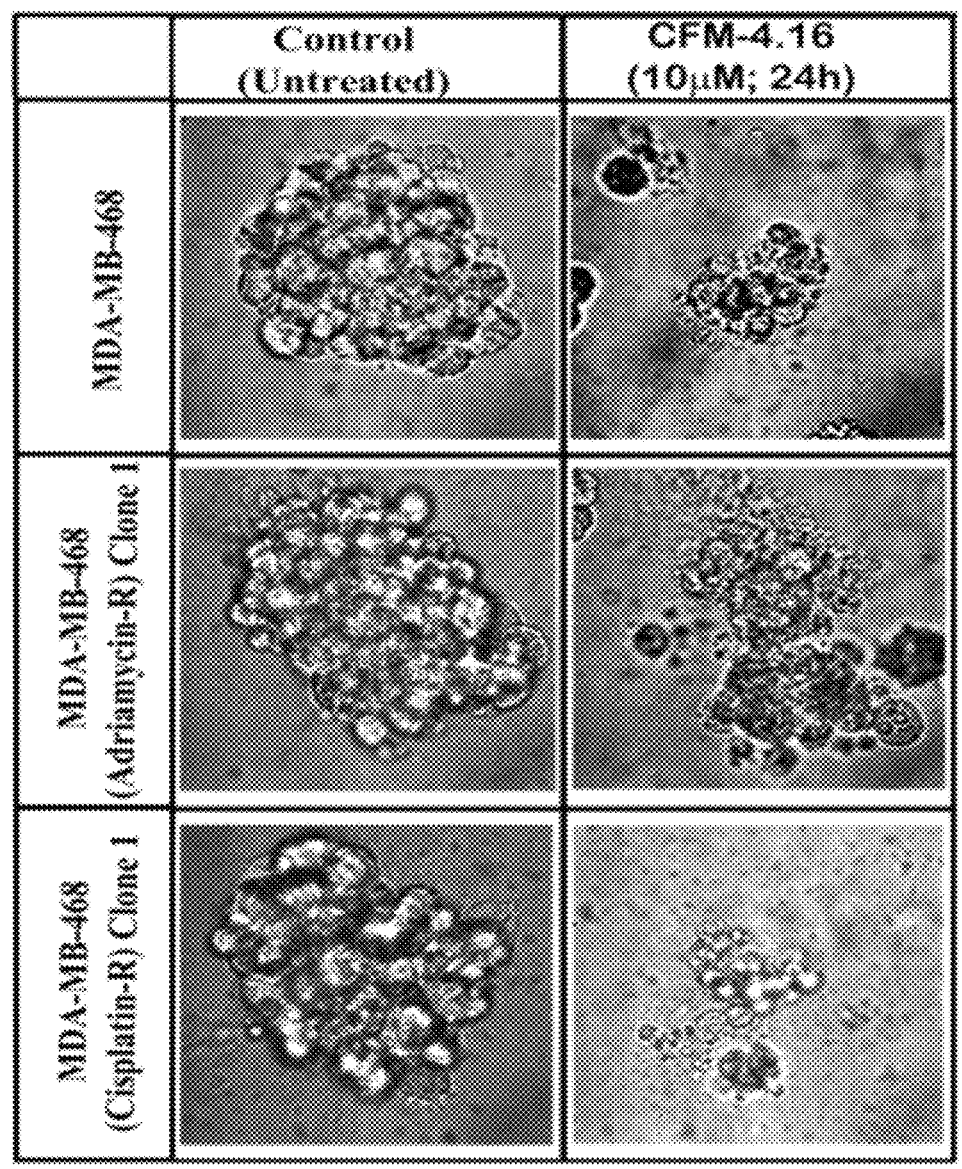
FIG. 15A depict photomicrographs of CFM-4.16 untreated and treated mammospheres. Parental and drug-resistant MDA-MB-468 TNBC cells were grown as mammospheres. The mammosphere cultures were either untreated (Control) or treated with CFM-4.16 for noted dose and time.
Figure 15B:
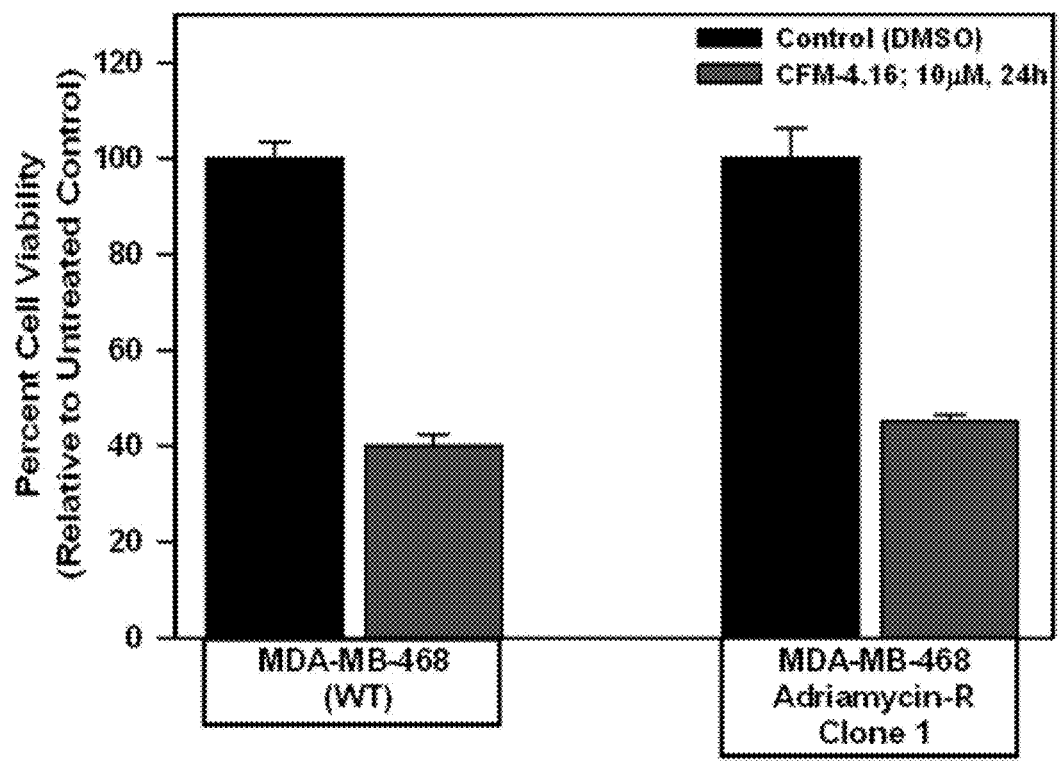
FIG. 15B depicts results when the cells of FIG. 15A were subjected to MTT-based viability assay as in FIGS. 3A-3C.
Figure 15C:
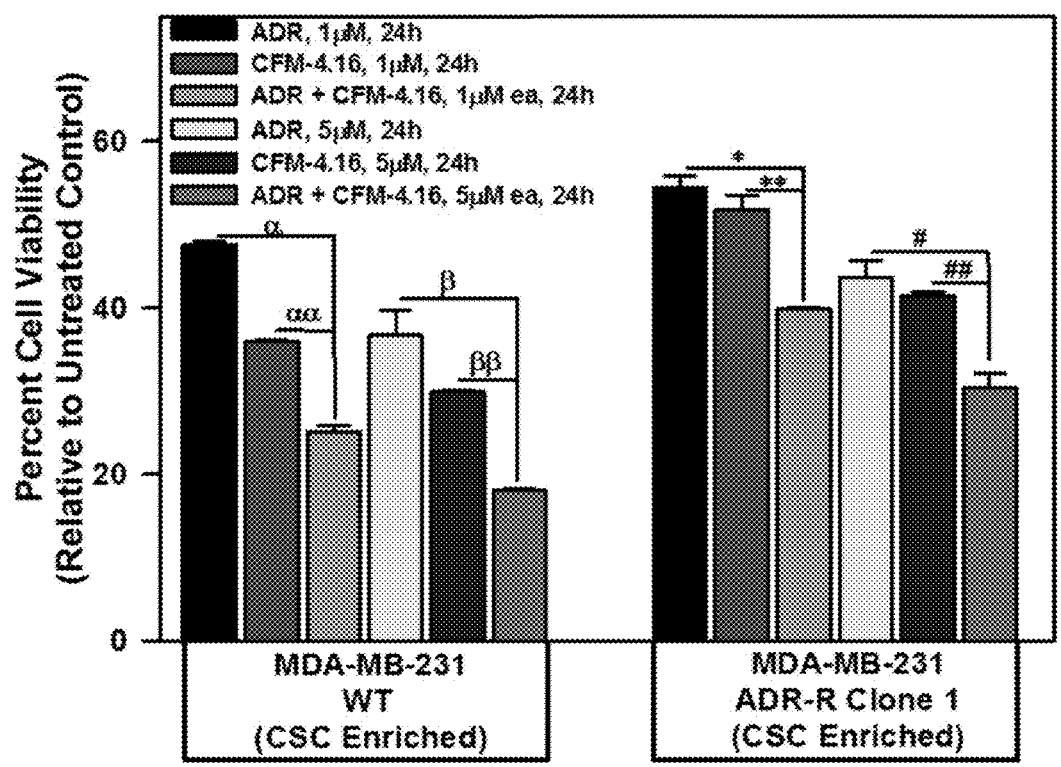
FIG. 15C shows that the tumor-derived cells from xenografts of parental and ADR-resistant TNBC cells were enriched for CSCs. The CSC-enriched cells were then treated with ADR, CFM-4.16, or a combination of both for noted dose and time. The cell viabilities were determined by MTT-based assay as in FIGS. 3A-3C, and plotted relative to the MTT values for the respective untreated controls. The histogram columns in panels B and C represent means of three and four independent experiments, respectively; bars, S. E. α, αα, β, ββ, *, , #, ##p=<0.03 relative to respective cells treated with ADR+CFM-4.16. Overall.

It was next clarified whether and to the extent CFM-4.16 was able to interfere with growth of mammospheres derived from parental and drug-resistant TNBC-cells. In the first instance, mammospheres were grown from the 2-D cultures of parental and drug-resistant MDA-MB-468 TNBC cells. The growing mammosphere cultures were then exposed to CFM-4.16, and the viabilities of untreated and treated cultures were determined by an MTT-based assay. Presence of CFM-4.16 caused disintegration of mammospheres of both the parental and drug-resistant MDA-MB-468 TNBC cells (FIG. 15A). MTT assays revealed a robust decline in viability of CFM-4.16-treated mammospheres of parental as well as ADR-resistant cells when compared with their respective DMSO-treated controls (FIG. 15B). Next, CSC-enriched populations derived from xenografts of parental and ADR-resistant MDA-MB-231 TNBC cells were utilized to determine their inhibition by ADR, CFM-4.16, and a combination of both the agents. As shown in FIG. 15C, either ADR or CFM-4.16 caused significant loss of viabilities of parental as well as ADR-resistant CSC enriched TNBC cells in a dose-dependent manner when compared with their untreated counterparts. Of note here is that CSC enriched populations derived from either the parental or ADR-resistant TNBC cells had significantly higher decline in their viabilities following exposure to a combination of CFM-4.16 and ADR when compared with the cells that were treated with either agent alone. Moreover, the parental CSC enriched cells treated with ADR, CFM-4.16, or a combination of both the agents generally had a greater decline in their viabilities when compared with the viabilities of similarly treated ADR-resistant CSC enriched cells (FIG. 15C). The increased survival of CFM-4.16 or ADR-treated, ADR-resistant CSC enriched cells when compared with similarly treated parental CSC enriched cells noted in FIG. 15C could be due in part to elevated levels of several CSC-associated markers in the ADR-resistant cells (see FIGS. 14A-14B) that are often well known to contribute to emergence, survival, and maintenance of drug resistance in TNBC and other cancers.

Figure 16A:
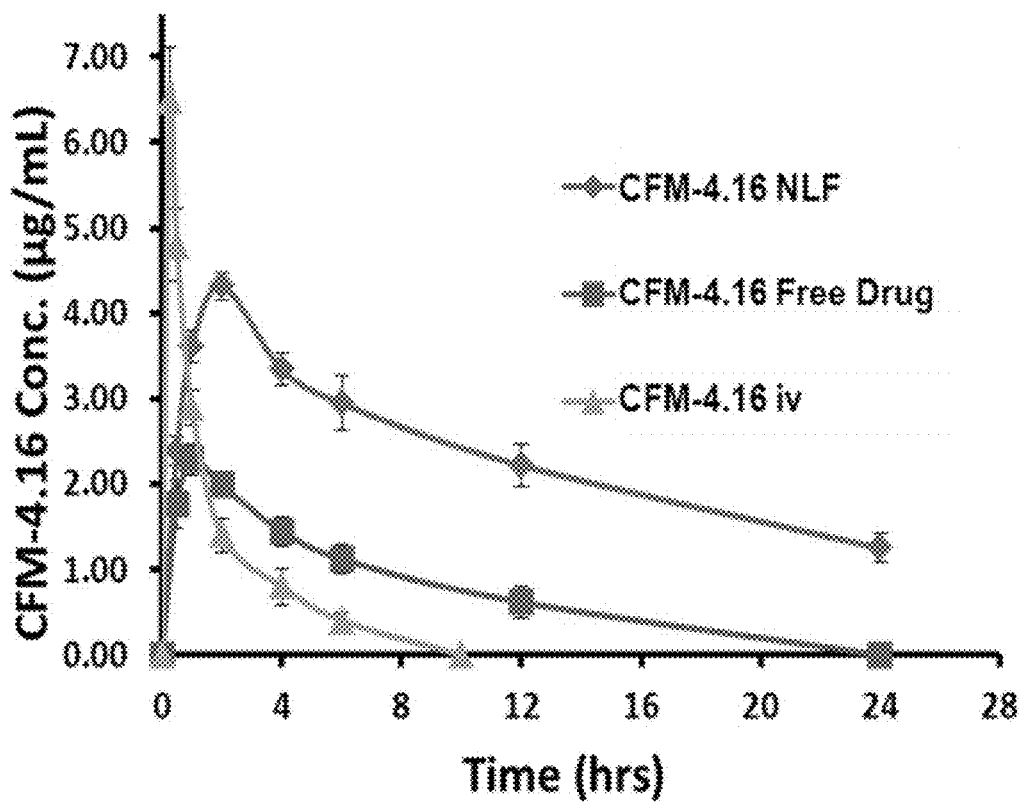
FIG. 16A depicts HPLC analysis of rat serum levels of CFM-4.16 at the noted time intervals following oral administration of indicated dose of CFM-4.16 NLF, CFM-4.16 Free drug, or intravenous (iv) administration of CFM-4.16 (noted as CFM-4.16 iv). Table in the lower part of panel A shows indicated pharmacokinetic parameters for CFM-4.16 when administered orally as CFM-4.16 free drug, CFM-4.16 NLF, or CFM-4.16 iv.

E. Oral Administration of CFM-4.16 NLF in Combination with Intravenous ADR Causes Superior Inhibition of Xenografted TNBC Tumors To investigate therapeutic potential of CFM-4.16, subcutaneous tumor xenografts derived from MDA-MB-231 TNBC cells were generated in NCR SCID mice and efficacy and potency of CFM-4.16 was first tested by intra-venous (Tail vein injection) administration. This experiment failed to yield a therapeutic T/C values for this agent (Not shown). Since the xenograft studies involved intravenous administration of CFM-4.16 that was dissolved in DMSO plus cremophor, and a similar preparation of parent compound CFM-4 was previously also found to lack therapeutic T/C values in multiple xenograft studies [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627], it was suspected that systemic metabolism of these compounds likely contributed to their lower levels in serum that could have resulted in their lack of xenograft inhibitory effects. However, oral administration of a nano-lipid formulation (NLF) of the parent compound CFM-4 (CFM-4 NLF) resulted in significant improvement in its bioavailability over that noted for the orally administered, free CFM-4 compound [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627]. Oral administration of CFM-4 NLF also inhibited growth of TNBC as well as non-small cell lung cancer cell-derived xenografts in vivo [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627]. On the basis of these prior findings, a nano-lipid formulation of CFM-4.16 (CFM-4.16 NLF) was prepared and tested for its bioavailability and efficacy in vivo. Oral administration of CFM-4.16 NLF resulted in a significant increase in the bioavailability when compared to CFM-4.16 Free drug (FIG. 16A). The plasma Cmax concentration of CFM-4.16 free drug was found to be 1.19±0.035 µg/ml. The Cmax concentration of CFM-4.16 NLF was 4.32±0.23 m/ml, which was a 3.63-fold increase when compared with CFM-4.16 free drug. The AUC for CFM-4.16 Free drug was 21.07±4.20 µg·h/ml, whereas for CFM-4.16 NLF it was 86.21±17.20 µg·h/ml. The AUC for CFM-4.16 NLF was 4.09-fold more compared to CFM-4.16 Free drug. A 2.48-fold increased plasma half-life (t1/2) of CFM-4.16 NLF suggests for a sustained release behavior of CFM-4.16 NLF. These studies therefore indicate that the improved pharmacokinetic parameters such as increased Cmax, t1/2 and AUC in the case of CFM-4.16 NLF led to its overall improved bioavailability over CFM-4.16 free drug by a 4.093-fold (FIG. 16A).

Figure 16B:
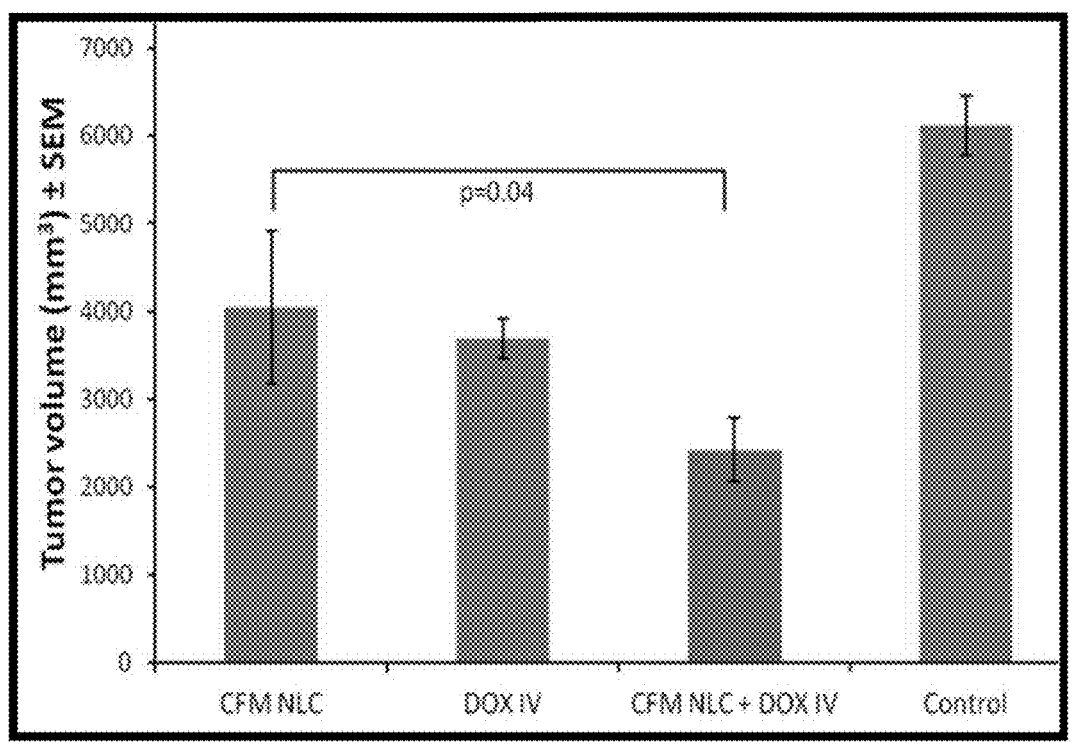
FIG. 16B depicts results of a histogram showing breast tumor volume of the placebo-treated (indicated as Control), CFM-4.16 NLF, Doxorubicin (indicated as DOX iv), or CFM-4.16 NLF+doxorubicin (indicated as CFM-4.16 NLF+DOX iv) treated, TNBC (MDA-MB-231) xenograft-bearing animals. The columns represent average values from a total of six animals in respective group, bars, SE, significant where *p=0.04 vs CFM NLF.
Figure 16C:
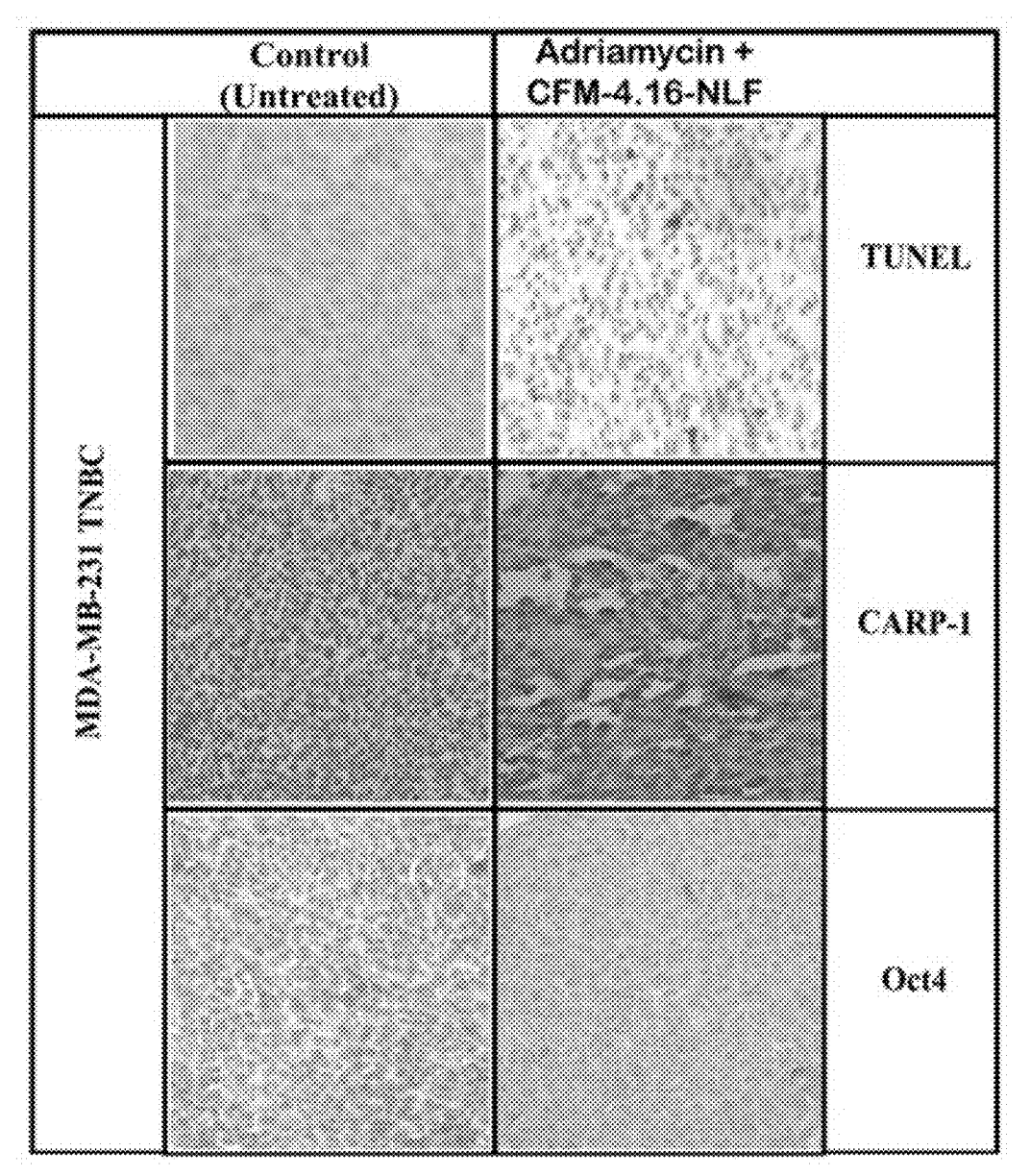

The in vivo antitumor efficacy of CFM-4.16 NLF, ADR (noted as DOX), or their combination was investigated in TNBC MDA-MB-231 orthotropic xenograft tumor bearing nude mice as described herein and in the current inventors' previously published studies [Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627]. As shown in FIG. 16B, all the treatment groups showed significant tumor growth inhibition compared to the control (placebo) group. Although oral administration of CFM-4.16 NLF resulted in reduced breast tumor volume, a significantly higher reduction in the tumor volumes was noted in the CFM-4.16 NLF plus ADR (-DOX) group when compared with CFM-4.16 NLF or ADR (-DOX)-treated groups. These data indicate a statistically improved antitumor effect of combination compared to single drug groups (p<0.05). Combination group showed 1.66 and 1.52-fold reduction in tumor volume compared to CFM-4.16 NLF and ADR (DOX) group, respectively (FIG. 16B). Immuno-histological analysis of a representative TNBC tumor from the animals that were treated with placebo (control) or CFM-4.16 NLF plus ADR revealed increased staining for TUNEL and CARP-1 protein, and reduced staining for Oct4 (FIG. 16C). The data in FIGS. 16A-16C collectively demonstrate that NLF formulation of CFM-4.16 enhances its bioavailability, serum levels, and anti-tumor efficacy. In addition, CFM-4.16 inhibited xenografted TNBC tumors in part by diminishing levels of CSC-associated markers, and inducing apoptosis, and these findings are consistent with the current in vitro observations as well as the current inventors' previous studies where CFM-4 and CFM-4.6 compounds were found to stimulate apoptosis in a variety of cancer cell types including those of NSCLC and TNBC origins [Puliyappadamba et al.; Muthu, M., Somagoni, J. M., Cheriyan, V. T., Munie, S., Levi, E., Ashour, A. E., Alafeefy, A. M., Sochacki, P., Polin, L. A., Reddy, K. B., Larsen, S. D., Singh, M., Rishi, A. K. Identification and testing of novel CARP-1 functional mimetic compounds as inhibitors of non-small cell lung and triple-negative breast cancers. J. Biomed. Nanotechnol. 2015; 11:1608-1627; Jamal S, Cheryan V T, Muthu M, Munie S, Levi E, Ashour A E, Pass H I, Wali A, Singh M, Rishi A K. CARP-1 functional mimetics are a novel class of small molecule inhibitors of malignant pleural mesothelioma cells. PLos One. 2014; 9:e89146; Ashour A E, Jamal S, Cheryan V T, Muthu M, Zoheir K M A, Alafeefy A M, Abd-allah AR, Levi E, Tarca A L, Polin L A, Rishi A K. CARP-1 functional mimetics: A novel class of small molecule inhibitors of medulloblastoma cell growth. PLoS One. 2013; 8:e66733].

Considering the foregoing results and data obtained, oral administration of CFM's nano-lipid formulation results in reduced growth of TNBC as well as non-small cell lung cancer (NSCLC) cell-derived xenografts in vivo. Given that frequent emergence of therapy-resistant TNBCs remains a significant and unresolved clinical problem, here a hypothesis was tested, namely that potent analog(s) of CFM-4 scaffold are suitable inhibitors of TNBCs and their drug-resistant phenotypes in vitro and pre-clinical animal studies.

As a first step in this direction, it was found that out of twelve additional analogs of CFM-4 obtained by medicinal chemistry based structure activity relationship (SAR) studies (Table 2), two compounds, CFM-4.16 and CFM-4.17, possessed activities that were superior to the parent compound CFM-4 or other analogs. Interestingly, the compound CFM-4.16 in combination with ADR caused greater growth inhibition of only the TNBC cells when compared with either agent alone (FIGS. 3A-3E). On these bases, CFM-4.16 was chosen to test its potential as an inhibitor of TNBCs including the drug-resistant TNBCs.

Given that emergence of TNBCs that are resistant to chemotherapeutic drugs such as ADR and Cisplatin is a significant problem in clinic, the potential of CFM-4.16 was investigated, along with its class of scaffold as inhibitors of drug-resistant TNBCs. To test this hypothesis, a model was first developed by growing human and murine TNBC cells in continuous presence of chemotherapy (Cisplatin or ADR) over periods longer than 6 months, and obtained and characterized number of drug-resistant TNBC sublines. Indeed, the drug-resistant TNBC sublines had higher $GI_{50}$ doses for the respective chemotherapeutic when compared with their parental, wild-type cells (see Table 3) indicating emergence of robust, drug-resistant TNBC phenotypes following stepwise dose escalation and chronic presence of the respective therapeutic. Importantly however, CFM-4.16 was effective in inhibiting viabilities of parental as well as drug-resistant TNBC cells in a dose-dependent manner (see FIGS. 4A-4E). Of note here is that CFM-4.16-dependent reduction in the viabilities of the drug-resistant cells was similar to that noted for the respective, CFM-4.16-treated parental cells, suggesting that molecular mechanisms of TNBC cell growth inhibition by CFM class of compounds are likely distinct from those utilized by chemotherapy such as ADR. Although ADR is known to require CARP-1 for apoptosis signaling in breast cancer including TNBC cells [Rishi A K, Zhang L, Boyanapalli M, Wali A, Mohammad R M, Yu Y, Fontana J A, Hatfield J S, Dawson M I, Majumdar A P N, Reichert U. Identification and characterization of a Cell-Cycle and Apoptosis Regulatory Protein [CARP]-1 as a novel mediator of apoptosis signaling by Retinoid CD437. J Biol Chem. 2003; 278:33422-33435; Rishi A K, Zhang L, Yu Y, Jiang Y, Nautiyal J, Wali A, Fontana J A, Levi E, Majumdar A P N. Cell cycle and apoptosis regulatory protein [CARP]-1 is involved in apoptosis signaling by epidermal growth factor receptor. J Biol Chem. 2006; 281:13188-98], and ADR-resistant TNBC cells express elevated levels of CARP-1, CFM-4.16 exposure caused a further increase in CARP-1 levels in ADR-resistant cells (FIGS. 5A-5E). Moreover, similar to CFM-4, treatments of parental or ADR-resistant TNBC cells with CFM-4.16 stimulated activation of caspase-8, stress-activated kinases p38 and JNK1/2, and cleavage of PARP while inhibiting activation of oncogenic MET RTK, and causing reduced levels of cyclin B1 (FIGS. 5A-5E and 7A-7C). Since depletion of CARP-1 in ADR-resistant TNBC cells also interfered with loss of their viabilities by CFM-4 or CFM-4.16 (FIGS. 5A-5E), collectively suggest for a requirement of CARP-1 for growth inhibition of ADR-resistant TNBC cells by CFM class of compounds. CFM-4 or CFM-4.16 also caused activation of stress and apoptosis signaling and CARP-1 increase in cisplatin-resistant TNBC and Herceptin-resistant, Her2-expressing SKBR-3 breast cancer cells (FIGS. 6A-6D). Thus, CFM-4.16 although functions in part by activating CARP-1 and stress signaling to induce apoptosis in a manner that is analogous to CFM-4, the fact that CFM-4.16 but not CFM-4 enhances efficacy of ADR only in the TNBC cells would underscore its potential as a promising novel scaffold for development of agents to target drug-resistant TNBCs.

Both the MET and Src tyrosine kinases have been well known as drivers of carcinogenesis and development of resistance to therapies in many cancers including the TNBCs [Ho-Yen C M, Jones J L, Kermorgant S. The clinical and functional significance of c-Met in breast cancer: a review. Breast Cancer Res. 2015; 17:52. doi: 10.1186/s13058-015-0547-6; Gelsomino F, Facchinetti F, Haspinger E R, Garassino M C, Trusolino L, De Braud F, Tiseo M. Targeting the MET gene for the treatment of non-small-cell lung cancer. Crit Rev Oncol Hematol. 2014; 89:284-99; Lehmann B D, Bauer J A, Chen X, Sanders M E, Chakravarthy A B, Shyr Y, Pietenpol J A. Identification of human triple-negative breast cancer subtypes and preclinical models for selection of targeted therapies," The Journal of Clinical Investigation. 2011; 121:2750-2767; Peddi P F, Ellis M J, Ma C. Molecular Basis of Triple Negative Breast Cancer and Implications for Therapy. International Journal of Breast Cancer. 2012, 2012:217185], and pre-clinical and clinical studies investigating benefits of MET or Src targeting have also been recently reported [Crown J, O'Shaughnessy J, Gullo G. Emerging targeted therapies in triple-negative breast cancer. Annals of Oncology. 2012; 23:56-65; Kim Y J, Choi J S, Seo J, Song J Y, Lee S E, Kwon M J, Kwon M J, Kundu J, Jung K, Oh E, Shin Y K, Choi Y L. MET is a potential target for use in combination therapy with EGFR inhibition in triple-negative/basal-like breast cancer. Int J Cancer. 2014, 15:2424-36]. Since MET activity was elevated in ADR or Cisplatin-resistant MDA-MB-468 cells, and Src activity was also elevated in ADR-resistant MDA-MB-468 and MDA-MB-231 cells (FIGS. 7A-7C and 9A-9B), would then be supportive of oncogenic roles of these kinases in drug-resistant TNBCs. Given that CFM-4.16 treatments caused diminished activities of MET in all the drug-resistant TNBC cells (FIGS. 7A-7C) while reducing Src in cisplatin-resistant TNBC cells only (FIGS. 8A-8D), would be consistent with previous investigations supporting utility of targeting of these oncogenic kinases in TNBCs. Moreover, pre-clinical studies in a wide variety of solid tumors have shown that dasatinib is primarily cytostatic, and this is consistent with the clinical experience, where dasatinib activity is associated with stable disease but complete responses are rarely observed [Montero J C, Seoane S, Ocana A, Pandiella A. Inhibition of SRC family kinases and receptor tyrosine kinases by dasatinib: possible combinations in solid tumors. Clin Cancer Res. 2011; 17:5546-52; Lue H, Cole B, Rao S, Podalak J, Gaest A, King C, Eide C, Wilmot B, Xue C, Spellman P, Heiser L, Tyner J, Thomas G. Src and STAT3 inhibitors synergize to promote tumor inhibition in renal cell carcinoma. Oncotarget. 2015; 6:44675-44687. doi: 10.18632/oncotarget.5971]. Since pre-treatment of drug-resistant TNBC cells with CFM-4.16 resulted in significantly enhanced efficacies of MET or Src inhibitors (FIG. 10), it would further argue for potential of CFM-4.16 scaffold to sensitize drug-resistant TNBCs to targeted therapies that are currently in the clinic (Src inhibitor Dasatinib) or under clinical development (MET inhibitor Tevatinib).

The current study further revealed that although drug-resistant TNBC cells have elevated expression of key regulators of stemness such as Klf4, Oct4, SOX2, cMyc and β-catenin (FIGS. 14A-14B), combination of CFM-4.16 and ADR cause diminished expression of Klf4, Oct4, and SOX2 in parental as well as ADR-resistant MDA-MB-231 cells. These findings would indicate that CFM-4.16 plus ADR are superior in targeting TNBC CSCs to prevent proliferation and differentiation of the small subset of stem-like populations. This possibility is further supported by the mammosphere studies where CFM-4.16 was effective in disrupting mammosphere structure of parental as well as drug-resistant TNBC cells. Collectively, the current in vitro studies demonstrate that although CFM-4.16 inhibits growth and survival of drug-resistant TNBC cells in part by stimulating apoptosis, its combination with ADR has unique ability to target pluripotent CSCs to suppress growth of parental and drug-resistant TNBC cells.

Given that a significant fraction of drug-like compounds that enter development programs often have poor aqueous solubility, and the fact that like CFM-4, CFM-4.16 also had poor aqueous solubility, prompted the generation and testing of its nanolipid formulation for oral bioavailability and absorption. The nanolipid formulation incorporating a combination of two high melting solid lipid carriers (Compritol & Geleol) and the co-surfactant Vitamin E TPGS (with Tween-80) to promote sustained release, and stability and permeability of CFM-4.16, respectively. To prevent lipolysis of formulation due to lipid digestibility in GI tract and minimize drug escape from lipid carriers, liquid lipid "Miglyol" was added in the formulation. A natural, biocompatible cationic polysaccharide chitosan was also used to improve drug availability in tumor and interaction of positively charged formulation with negatively charged tumor surface. Indeed, CFM-4.16 exhibited good lipid solubility (FIG. 16A), and CFM-4.16 NLF exhibited superior absorption as indicated by pharmacokinetic parameters Cmax and AUC values when compared to free compound.

Finally, the preclinical studies with TNBC cell-derived xenografts demonstrate therapeutic potential of CFM-4.16. Oral administration of CFM-4.16 NLF suppressed growth of xenografted TNBC tumors in nude mice with an efficacy that was comparable to that noted for intravenously administered ADR (DOX). Interestingly, a combination of CFM-4.16 NLF and ADR elicited a significantly superior suppression of xenograft growth when compared to that noted with each agent alone. The facts that elevated CARP-1 and apoptosis, and diminished Oct4, were noted in xenografts from animals treated CFM-4.16 NLF plus ADR but not in control, untreated animals (FIG. 16C), corroborate the current in vitro observations and highlight a unique property of CFM-4.16 to enhance ADR efficacy in part by targeting CSCs for suppressing TNBCs.

In conclusion, this study reported identification of a novel CFM analog that inhibits viabilities of parental and drug-resistant TNBC cells in vitro. In addition to inhibiting expression and/or activation of various growth and survival-promoting genes, CFM-4.16 inhibited expression of proteins associated with stem-like cells. CFM-4.16 in combination with TKIs (Dasatinib or Tivatinib) caused greater loss of viabilities of parental as well as ADR-resistant TNBC cells. Pre-treatments with CFM-4.16 increased ADR-dependent inhibition of cell viability of only the TNBC cells in vitro, while a combination of ADR and CFM-4.16 elicited superior inhibition of growth of TNBC cell-derived xenografts in vivo when compared with either agent alone.

Glossary of Claim Terms

About: This term is used herein to refer to approximately or nearly and in the context of a numerical value or range set forth means±15% of the numerical. In an embodiment, the term "about" can include traditional rounding according to significant figures of the numerical value. In addition, the phrase "about 'x' to 'y'" includes "about 'x' to about 'y'".

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range.

Administer: This term is used herein to refer to the process by which a composition comprising a CFM compound as an active agent, are delivered to a patient or individual for therapeutic purposes. The composition of the subject invention and methodology in use thereof can be administered a number of ways including, but not limited to, parenteral (such term referring to intravenous and intra-arterial as well as other appropriate parenteral routes), subcutaneous, peritoneal, inhalation, vaginal, rectal, nasal, or instillation into body compartments. The preferred administration method is orally due to the advantages described previously. The current invention resolves the drawback of a lack of bioavailability of orally-administered CFM, as previously discussed. Administration will often depend upon the amount of compound administered, the number of doses, and duration of treatment. In an embodiment, multiple doses of the agent are administered. The frequency of administration of the agent can vary depending on any of a variety of factors, such as tumor volume/progression, and the like. The duration of administration of the agent, e.g., the period of time over which the agent is administered, can vary, depending on any of a variety of factors, including patient response, etc. The amount of the agent contacted (e.g., administered) can vary according to factors such as the degree of susceptibility of the individual, the age, sex, and weight of the individual, idiosyncratic responses of the individual, the dosimetry, and the like. Detectably effective amounts of the agent of the present disclosure can also vary according to instrument and film-related factors. Optimization of such factors is well within the level of skill in the art, unless otherwise noted, such as with the unexpected results obtained by admixing CFM with DMA, oil, surfactant, etc. to allow CFM to actually be soluble and bioavailable for anti-cancer therapies.

Enhanced oral bioavailability: This term is used herein to refer to increased absorption of an agent when administered/ingested via the mouth (e.g., in a pill or capsule form), as compared to the conventional art.

Enhanced solubility: This term is used herein to refer to increased dissolution of an agent in a particular solvent, as compared to the conventional art.

Pharmaceutically acceptable excipient: This term is used herein to refer to an excipient, diluent, carrier, and/or adjuvant that are useful in preparing a pharmaceutical composition that are generally safe, non-toxic and neither biologically nor otherwise undesirable, and include an excipient, diluent, carrier, and adjuvant that are acceptable for veterinary use and/or human pharmaceutical use. "A pharmaceutically acceptable excipient" as used in the specification and claims includes one or more such excipients, diluents, carriers, and adjuvants.

Subject or patient: This term is used herein to refer to humans and mammals (e.g., mice, rats, pigs, cats, dogs, and horses). Typical hosts to which an agent(s) of the present disclosure may be administered will be mammals, particularly primates, especially humans. For veterinary applications, a wide variety of subjects will be suitable, e.g., livestock such as cattle, sheep, goats, cows, swine, and the like; poultry such as chickens, ducks, geese, turkeys, and the like; and domesticated animals particularly pets such as dogs and cats. For diagnostic or research applications, a wide variety of mammals will be suitable subjects, including rodents (e.g., mice, rats, hamsters), rabbits, primates, and swine such as inbred pigs and the like.

Therapeutically effective amount: This term is used herein to refer to concentrations or amounts of components such as agents which are effective for producing an intended result, including tumor regression. Compositions according to the present invention may be used to effect a favorable change in tumor volume, whether that change is an improvement, relieving to some extent one or more of the symptoms of the condition being treated, and/or that amount that will prevent, to some extent, one or more of the symptoms of the condition that the host being treated has or is at risk of developing, or a complete cure of the disease or condition treated.

Treat: This term is used herein to refer to acting upon a condition (e.g., tumor presence) with an agent (e.g., CFM compound) to affect the condition by improving or altering it. The improvement or alteration may include an improvement in symptoms or an alteration in the physiologic pathways associated with the condition. The aforementioned terms cover one or more treatments of a condition in a patient (e.g., a mammal, typically a human or non-human animal of veterinary interest), and includes: (a) reducing the risk of occurrence of the condition in a subject determined to be predisposed to the condition but not yet diagnosed, (b) impeding the development of the condition, and/or (c) relieving the condition, e.g., causing regression of the condition and/or relieving one or more condition symptoms (e.g., tumor regression). As used herein, the terms "prophylactically treat" or "prophylactically treating" refers completely or partially preventing (e.g., about 50% or more, about 60% or more, about 70% or more, about 80% or more, about 90% or more, about 95% or more, or about 99% or more) a condition or symptom thereof and/or may be therapeutic in terms of a partial or complete cure or alleviation for a condition and/or adverse effect attributable to the condition.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A solid self-micro/nano emulsifying formulation comprising a therapeutically-effective amount of a cell cycle and apoptosis regulatory protein-1 functional mimetic, wherein the solid self-micro/nano emulsifying formulation increases oral bioavailability of the cell cycle and apoptosis regulatory protein-1 functional mimetic upon oral ingestion and increases solubility of the cell cycle and apoptosis regulatory protein-1 functional mimetic in an organic solvent, wherein the cell cycle and apoptosis regulatory protein-1 functional mimetic is selected from the group consisting of CFM-4, CFM-5, CFM-4.1, CFM-4.16, CFM 4.17, CFM 4.2, CFM-4.3, CFM-4.4, CFM-4.5, and combinations thereof.

2. A formulation as in claim 1, further comprising a pharmaceutically acceptable lipidic excipient and a surfactant admixed with the cell cycle and apoptosis regulatory protein-1 functional mimetic.

3. A formulation as in claim 2, wherein the lipidic excipient is an oil.

4. A formulation as in claim 3, wherein the surfactant is present in an amount between about 0.1% and about 50% by weight and wherein the oil is present in an amount between about 20% and about 80% by weight.

5. A formulation as in claim 1, wherein the organic solvent is dimethyl acetamide in which the cell cycle and apoptosis regulatory protein-1 functional mimetic is solubilized in the formulation.

6. A formulation as in claim 1, wherein the therapeutically effective amount of the cell cycle and apoptosis regulatory protein-1 functional mimetic is about 40 mg/kg of body weight of a patient or subject to which the formulation is orally administered.

7. A method of treating cancer in a patient or subject, comprising orally administering a therapeutically effective amount of a solid self-micro/nano emulsifying formulation containing a cell cycle and apoptosis regulatory protein-1 functional mimetic, wherein the solid self-micro/nano emulsifying formulation increases oral bioavailability the cell cycle and apoptosis regulatory protein-1 functional mimetic upon oral ingestion and increases solubility of the cell cycle and apoptosis regulatory protein-1 functional mimetic in an organic solvent, wherein the cell cycle and apoptosis regulatory protein-1 functional mimetic is selected from the group consisting of CFM-4, CFM-5, CFM-4.1, CFM-4.16, CFM 4.17, CFM 4.2, CFM-4.3, CFM-4.4, CFM-4.5, and combinations thereof, wherein said cancer is selected from the group consisting of breast cancer, triple negative breast cancer, resistant lung cancer, and non-resistant lung cancer.

8. A method as in claim 7, wherein the formulation is administered orally approximately every other day.

9. A method as in claim 7, wherein the formulation further comprises a pharmaceutically acceptable lipidic excipient and a surfactant admixed with the cell cycle and apoptosis regulatory protein-1 functional mimetic.

10. A method as in claim 9, wherein the lipidic excipient is an oil.

11. A method as in claim 10, wherein the surfactant is present in an amount between about 0.1% and about 50% by weight and wherein the oil is present in an amount between about 20% and about 80% by weight.

12. A method as in claim 7, wherein the organic solvent is dimethyl acetamide in which the cell cycle and apoptosis regulatory protein-1 functional mimetic is solubilized in the formulation.

13. A method as in claim 7, wherein the therapeutically effective amount of the cell cycle and apoptosis regulatory protein-1 functional mimetic is about 40 mg/kg of body weight of a patient or subject to which the formulation is orally administered.

* * * * *